United States Patent
Kadobayashi et al.

(10) Patent No.: US 11,207,247 B2
(45) Date of Patent: Dec. 28, 2021

(54) LOW WATER-SENSITIVE DENTAL COMPOSITION

(71) Applicant: SHOFU INC., Kyoto (JP)

(72) Inventors: Yusei Kadobayashi, Kyoto (JP); Hiroshi Yaana, Kyoto (JP); Jun Uchida, Kyoto (JP); Yuji Sadakane, Kyoto (JP)

(73) Assignee: SHOFU INC., Kyoto (JP)

( * ) Notice: Subject to any disclaimer, the term of this patent is extended or adjusted under 35 U.S.C. 154(b) by 0 days.

(21) Appl. No.: 16/829,259

(22) Filed: Mar. 25, 2020

(65) Prior Publication Data

US 2021/0007938 A1    Jan. 14, 2021

(30) Foreign Application Priority Data

| Mar. 26, 2019 | (JP) | JP2019-057535 |
| Mar. 26, 2019 | (JP) | JP2019-057536 |
| Mar. 26, 2019 | (JP) | JP2019-057537 |
| Mar. 26, 2019 | (JP) | JP2019-057538 |
| Mar. 26, 2019 | (JP) | JP2019-057555 |
| Mar. 26, 2019 | (JP) | JP2019-057556 |
| Aug. 19, 2019 | (JP) | JP2019-150038 |
| Sep. 26, 2019 | (JP) | JP2019-175309 |
| Sep. 26, 2019 | (JP) | JP2019-175327 |
| Sep. 26, 2019 | (JP) | JP2019-175336 |
| Sep. 26, 2019 | (JP) | JP2019-175354 |
| Dec. 24, 2019 | (JP) | JP2019-232733 |

(51) Int. Cl.

| A61K 6/889 | (2020.01) |
| A61K 6/20 | (2020.01) |
| A61K 6/833 | (2020.01) |
| C08F 120/56 | (2006.01) |
| A61K 6/836 | (2020.01) |
| A61K 6/62 | (2020.01) |
| A61K 6/77 | (2020.01) |
| A61K 6/30 | (2020.01) |
| A61K 6/40 | (2020.01) |
| A61K 6/887 | (2020.01) |

(52) U.S. Cl.
CPC .............. A61K 6/889 (2020.01); A61K 6/20 (2020.01); A61K 6/30 (2020.01); A61K 6/40 (2020.01); A61K 6/62 (2020.01); A61K 6/77 (2020.01); A61K 6/833 (2020.01); A61K 6/836 (2020.01); A61K 6/887 (2020.01); C08F 120/56 (2013.01)

(58) Field of Classification Search
None
See application file for complete search history.

(56) References Cited

U.S. PATENT DOCUMENTS

| 2005/0020721 A1 | 1/2005 | Stannard et al. |
| 2009/0299006 A1 | 12/2009 | Shinno et al. |
| 2011/0098375 A1 | 4/2011 | Gyakushi et al. |
| 2016/0030298 A1 | 2/2016 | Kadobayashi et al. |
| 2017/0296442 A1 | 10/2017 | Renn et al. |
| 2018/0296445 A1* | 10/2018 | Amao ................ C08L 27/04 |
| 2018/0360696 A1 | 12/2018 | Nojiri et al. |
| 2020/0069531 A1* | 3/2020 | Shigenoi ............ A61K 6/20 |
| 2021/0007938 A1* | 1/2021 | Kadobayashi ........... A61K 6/30 |

FOREIGN PATENT DOCUMENTS

| JP | 6-345614 | 12/1994 |
| JP | 2006-512466 | 4/2006 |
| JP | 2008-201726 | 9/2008 |
| JP | 2014-55115 | 3/2014 |
| JP | 2015-168672 | 9/2015 |
| JP | 2016-30752 | 3/2016 |
| JP | 2017-105716 | 6/2017 |
| WO | 2007/135742 | 11/2007 |
| WO | 2010/010901 | 1/2010 |
| WO | WO-2018212061 A1 * | 11/2018 ............. B32B 27/30 |

OTHER PUBLICATIONS

STIC Structure search—16829259—624685—EISEARCH (Year: 2021).*
Extended European Search Report dated Oct. 6, 2020 in European Patent Application No. 20165741.8.

* cited by examiner

Primary Examiner — Peter A Salamon
(74) Attorney, Agent, or Firm — Wenderoth, Lind & Ponack, L.L.P.

(57) ABSTRACT

An object of the present disclosure is to provide a dental composition that can exhibit sufficient curability even in a state where moisture is excessive as in the oral environment. The dental composition of the present disclosure contains component (a): monomer containing (meth)acrylamide group represented by formula (1):

[Chemical Formula 1]

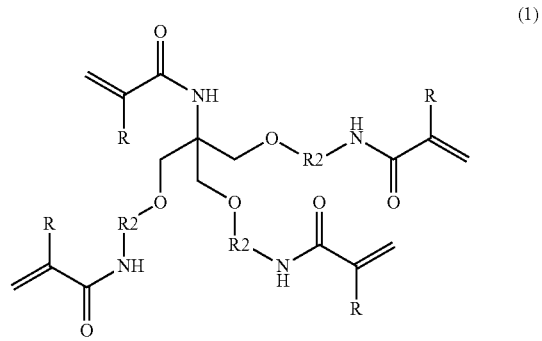

(1)

(In formula, R represents a hydrogen atom or a methyl group and Rs may be the same or different from each other. R2 is an alkyl group having 2 to 6 carbon atoms and R2s may be the same or different from each other.)

14 Claims, No Drawings

LOW WATER-SENSITIVE DENTAL COMPOSITION

CROSS-REFERENCE TO RELATED APPLICATIONS

This application is based on and claims the benefit of priorities from Japanese Patent Application Serial No. 2019-57535, Japanese Patent Application Serial No. 2019-57536, Japanese Patent Application Serial No. 2019-57537 and Japanese Patent Application Serial No. 2019-57538 (filed on Mar. 26, 2019), Japanese Patent Application Serial No. 2019-150038 (filed on Aug. 19, 2019), Japanese Patent Application Serial No. 2019-175309, Japanese Patent Application Serial No. 2019-175327, Japanese Patent Application Serial No. 2019-175336 and Japanese Patent Application Serial No. 2019-175354 (filed on Sep. 26, 2019), and, Japanese Patent Application Serial No. 2019-232733 (filed on Dec. 24, 2019), the contents of which are hereby incorporated by reference in their entirety.

BACKGROUND OF THE INVENTION

Field of the Invention

The present disclosure relates to a dental composition.

Description of the Related Art

Various dental compositions have been used in dental treatment.

Japanese unexamined patent application publication No. 2016-30752 A discloses a dental composition which is a dental composite material composition containing a filler, a monomer and a polymerization initiator. The dental composite material composition has been used as a dental filling restoring material, a crown prosthesis material such as an inlay, a crown and a bridge, and an abutment tooth building material.

Japanese unexamined patent application publication (Translation of PCT Application) No. 2006-512466 A discloses a dental composition which is a polymerizable composite material containing at least one polyfunctional monomer containing an acid, a non-reactive filler, a polymerization system, and water, and is a self-adhesive resin cement that does not require a primer. The resin cement has been used for imparting adhesive property to each adhered when a dental prosthesis restoration material made of ceramics, composite resin or metal material is adhered to the base of a biological hard tissue, especially an enamel or a dentin of natural tooth.

Japanese unexamined patent application publication No. H06-345614 A discloses a dental composition which is a denture base resin composition containing an acrylate monomer, an organic filler, and an α-aminoacetophenone photoinitiator. The denture base resin composition has been used for preparing temporary inlays, crowns, bridges, trays for individual tooth, and repairing a denture base.

PCT International Publication No. WO2007/135742 discloses a dental composition which is a tooth substance adhesive primer containing (a) a phosphonic acid group-containing polymerizable monomer, (b) a polyvalent carboxylic acid group-containing polymerizable monomer, (c) water, (d) a water-soluble organic compound and (e) a polymerization catalyst. The tooth substance adhesive primer has been used in the dental field to adhere to a biological hard tissue (an enamel or a dentin of natural tooth) or the like.

Japanese unexamined patent application publication No. 2015-168672 A and Japanese unexamined patent application publication No. 2014-55115 A disclose a dental composition which is a dental primer using a phosphoric acid-based monomer. The dental primer has been used for modifying the fractured surface of the tooth restoration in order to bond a composite resin.

Japanese unexamined patent application publication No. 2008-201726 A and PCT International Publication No. WO2010/010901 disclose a dental composition which is an adhesive composition in which a polymerizable monomer having an acidic group derived from phosphoric acid and a polyvalent metal ion are compounded. The adhesive composition has been used in the dental field to adhere a dental material such as a restoration material, a crown material, a prosthetic material, a preventive material, an abutment building material, and a root canal material to a ceramics, a resin, a composite resin, a glass ionomer cement, a biological hard tissue (an enamel or a dentin of natural tooth) and the like.

Japanese unexamined patent application publication No. 2017-105716 A discloses a self-adhesive dental composite resin having excellent adhesive property not only to a dentin not subjected to phosphoric acid etching treatment but also to a dentin subjected to phosphoric acid etching treatment. The composite resin has been used in a composite resin restoration in which a caries that has developed in a tooth is removed to form a cavity and then a resin-based filling restoring material is filled.

SUMMARY OF THE INVENTION

Technical Problem

In recent years, the usage range of dental compositions has been expanding. However, the conventional dental composition has a defect in that it has poor curability in an environment containing moisture, which is in a highly wet state such as in the oral cavity, or on an adherend that has absorbed water. Therefore, there is a demand for the development of a dental composition that can exhibit sufficient curability even in a state where moisture is excessive as in the oral environment.

As a result of intensive studies to achieve the above problem, the present inventors have solved this problem by providing a dental composition which contains a monomer containing a (meth)acrylamide group having a specific structure. The present disclosure is based on the above findings.

Solution to Problem

The dental composition of the present disclosure contains component (a): monomer containing (meth)acrylamide group represented by formula (1):

[Chemical Formula 1]

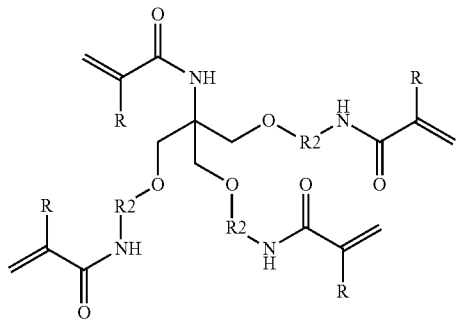

(1)

(In formula, R represents a hydrogen atom or a methyl group and Rs may be the same or different from each other. R2 is an alkyl group having 2 to 6 carbon atoms and R2s may be the same or different from each other).

Advantageous Effects of Invention

According to the present disclosure, it is possible to provide a dental composition that can exhibit sufficient curability even in a state where moisture is excessive, such as under the environment of the oral cavity.

DETAILED DESCRIPTION OF THE PREFERRED EMBODIMENTS

A dental composition of the present disclosure contains component (a): monomer containing (meth)acrylamide group represented by formula (1). The component (a) used in the dental composition of the present disclosure is an essential component for improving curability, particularly in the presence of water, and any monomer can be used without any limitation as long as such monomer has a (meth) acrylamide group represented by the following formula (1).

[Chemical Formula 2]

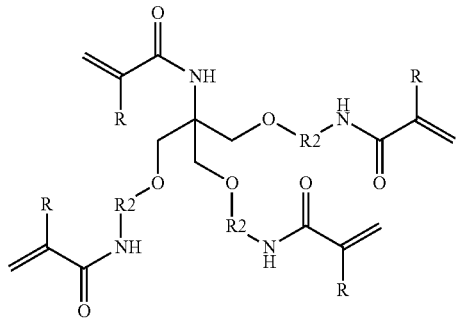

(1)

(In formula, R represents a hydrogen atom or a methyl group and Rs may be the same or different from each other. R2 is an alkyl group having 2 to 6 carbon atoms and R2s may be the same or different from each other.)

Specific examples of the component (a) represented by the formula (1) include those represented by following formulas (2) and (8).

[Chemical Formula 3]

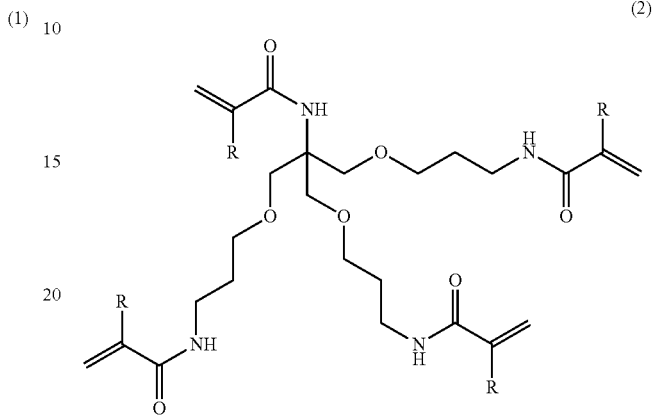

(2)

(In formula, R represents a hydrogen atom or a methyl group and Rs may be the same or different from each other.)

[Chemical Formula 4]

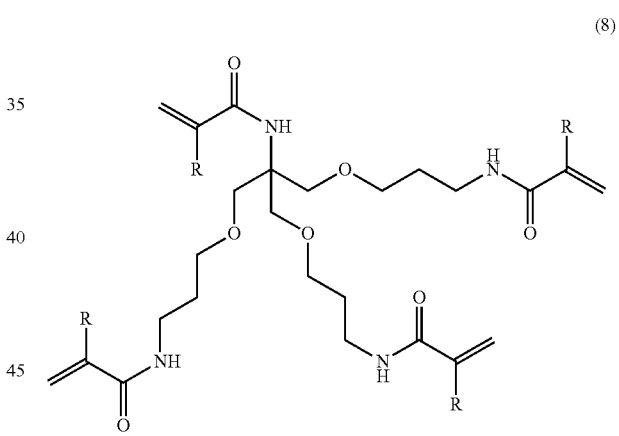

(8)

(In formula, R represents a hydrogen atom.)

In the dental composition of the present disclosure, the component (a) is preferably the one represented by the above formula (2), and more preferably the one represented by the above formula (8). The dental composition of the present disclosure preferably does not include bi- or less functional (meth)acrylamide group-containing monomer, more preferably does not include tri- or less functional (meth)acrylamide group-containing monomer, and most preferably does not include a monomer containing a (meth) acrylamide group and not represented by the above formula (1).

In the dental composition of the present disclosure, it is preferable that the any one or more of the following conditions (A) to (E) is satisfied.

Condition (A): component (c): monomer other than the component (a) is contained, and a ratio of the component (a) in the total amount of the component (a) and the component (c) is within a range of 0.1 to 20 wt. %.

Condition (B): component (h): radical-polymerizable monomer is contained, and 0.1 to 20 parts by weight of the component (a) is contained with respect to 100 parts by weight of the component (h).

Condition (C): component (0: polymerization catalyst is contained, and 0.1 to 20 parts by weight of the component (a) is contained with respect to 100 parts by weight of the total of the components of the dental composition excluding the component (a) and the component (f).

Condition (D): component (p): organic solvent, component (g): silane coupling agent, and component (q): acid anhydride and/or weakly acidic compound are contained.

Condition (E): the component (a) is contained within a range of 0.1 to 20 wt. %.

The dental composition of the present disclosure can be used in various applications, for example, a dental composite material composition, a resin cement, a denture restorative material, a tooth substance adhesive primer, a dental primer, a dental adhesive composition, a tooth substance adhesive composition, a dental adhesive resin cement, a self-adhesive dental composite resin and an adhesive composition.

[Dental Composite Material Composition]

For example, the dental composition of the present disclosure may be a dental composite material composition. The dental composite material composition is generally called as a dental composite resin and utilized for various uses such as direct restorative materials for tooth defective parts due to dental caries and the like, dental crown prosthesis restorative materials such as an inlay, a crown and a bridge, an abutment tooth building material for dental crown defective parts.

A composite material consisting of a dental composite material composition such as a dental composite resin is prepared by mixing a filler and a monomer in the form of a paste. The pasty composite material is provided to dentists and dental technicians, which are the user, in a state of be filled in a packaging container filled with the composite material. In the dental composite material composition, the composite material is generally prepared in the form of a paste by mixing a filler and a monomer in the appropriate amount, and then is filled in a packaging container. Depending on the intended use of the composite material, an opacifying agent or a pigment may be added. A composite material consisting of a dental composite material composition is often used to restore a restoration in the oral cavity, and is often used in an environment affected by water in the oral cavity.

In recent years, the usage range of composite materials consisting of a dental composite material composition such as a dental composite resin has been expanding. However, the conventional dental composite resin has a defect in that it has poor curability in an environment containing moisture, which is in a highly wet state such as in the oral cavity. Therefore, there is a demand for the development of a dental composite material, such as a dental composite resin, that can exhibit sufficient curability even in a state where moisture is excessive as in the oral environment.

The dental composition of the present disclosure in case of a dental composite material composition may be, for example, a dental composition containing component (a): monomer containing (meth)acrylamide group represented by formula (1),
component (b): filler,
component (c): monomer other than the component (a), and
component (d): polymerization initiator, and
wherein a ratio of the component (a) in the total amount of the component (a) and the component (c) is within a range of 0.1 to 20 wt. %.

That is, the dental composition of the present disclosure in case of a dental composite material composition is a dental composition containing a filler, a monomer, and a polymerization initiator, wherein the monomer contains a component (a): monomer containing (meth)acrylamide group represented by formula (1), and a ratio of the component (a): monomer containing (meth)acrylamide group represented by formula (1) in the monomer (total amount) is within a range of 0.1 to 20 wt. %. The ratio is preferably within a range of 1 to 15 wt. %, and more preferably within a range of 2 to 10 wt. %.

In this case, it is preferable to further contain component (e): fine particle filler.

The dental composition of the present disclosure can provide a dental composite material, such as a dental composite resin, that can exhibit sufficient curability even in a state where moisture is excessive as in the oral environment.

[Resin Cement]

For example, the dental composition of the present disclosure may be a resin cement. The resin cement is highly required as an adhesive for a dental prosthesis restorative material exhibiting the aesthetic property, and contains a filler consisting of an organic, an inorganic and/or an organic-inorganic composite material, and a polymerizable monomer or an oligomer. A filling ratio of the filler is approximately 50 wt. % or more in order to achieve a high material strength. In addition, it is possible to polymerize and set even in a portion where light does not reach, a dual-cure type has been mainly used, which has the chemical polymerization function in addition to the photopolymerization function.

For restoring a tooth which have underwent a relatively large damage due to dental caries or the like, a procedure is generally used, in which a crown, a bridge, an inlay, an onlay and the like which is made of ceramics, composite resins or metal materials is adhered with the resin cement. In this case, a pre-treatment agent, so called a primer, is used, in order to strengthen adhesive property of the resin cement to a dental hard tissue. Sufficient adhesive property and material strength thereof are required for such the resin cement. Otherwise, there is a possibility that the restoration may be dropped during a long period use under severe oral environment, and there is a risk that a clearance may be produced at an interface between the resin cement and the tooth substance, and bacteria may invade therefrom and adversely effect on dental pulp.

The dental hard tissue is composed of an enamel and a dentin, and adhesion of the resin cement to both of them is clinically required. The primer for pre-treating a tooth surface has been conventionally used prior to application of the resin cement for enhancing adhesive property. Such the primer demineralizes the tooth surface to make it rough, and facilitating infiltration of the resin cement into a fine rough surface. An adhesion mechanism that, thereafter, the resin cement is set by chemical polymerization or photopolymerization is considered.

On the other hand, as the conventional resin cement, a powder-liquid type has been used, but a resin cement which is used by mixing two pre-pasted compositions has been highly required in order to avoid a cumbersome procedure of mixing the powder and the liquid. Such the procedure of mixing the pastes reduces a mixing time and a difference between persons as compared with the procedure of mixing the powder and the liquid and, therefore, is a preferable type for clinicians. Moreover, in addition to by photopolymerization, the polymerization setting function by chemical polymerization, i.e. the dual cure polymerization setting function, is required for such the resin cement, so that it may be used for a high light-transmittable prosthesis restorative material such as a dental porcelain, in addition to a low light-transmittable prosthesis restorative material such as a dental alloy.

However, prior to adhesion with the resin cement, each adherend of a tooth substance, a ceramic, a composite resin and metal should be treated with an exclusive primer for each of various adherends in advance. Clinically, a simple adhesion procedure is desired, which does not require a primer treatment for such various adherends.

In recent years, the usage range of dental resin cements has been expanding. However, the conventional dental resin cement has a defect in that it has poor curability in an environment containing moisture, such as in the oral cavity, or on an adherend that has absorbed water and therefore sufficient adhesive property is not obtained. Therefore, there is a demand for the development of a dental resin cement having clinically acceptable adhesive property, without pretreatment with a primer, to various adherends having different properties such as a tooth substance of both an enamel and a dentin, a ceramics such as zirconia and alumina, a porcelain, metal and the like even on an adherend that has absorbed water and in a state where moisture is excessive as in the oral environment.

The dental composition of the present disclosure in case of a resin cement may be, for example, a dental composition containing component (a): monomer containing (meth)acrylamide group represented by formula (1),
component (b): filler,
component (f): polymerization catalyst,
component (g): silane coupling agent,
component (h): radical polymerizable monomer, and
component (i): acidic group-containing monomer, and
wherein 0.1 to 20 parts by weight of the component (a) is contained with respect to 100 parts by weight of the component (h).

That is, the dental composition of the present disclosure in case of a resin cement is a dental composition containing a filler, a polymerization catalyst, a silane coupling agent, a radical polymerizable monomer, and an acidic group-containing monomer, and 0.1 to 20 parts by weight of the component (a): monomer containing (meth)acrylamide group represented by formula (1) is contained with respect to 100 parts by weight of the radical polymerizable monomer.

The dental composition of the present disclosure can provide a dental resin cement having sufficient adhesive property, without using a primer specific to the adherend, to a tooth substance of an enamel and a dentin, a dental ceramic (porcelain), a composite resin and metal even on a test piece that has absorbed water and in a state where moisture is excessive as in the oral environment.

[Denture Restorative Material]

For example, the dental composition of the present disclosure may be a denture restorative material. The denture restorative material includes a dental powder-liquid type acrylic material in which a catalyst is compounded separately in a powder material of a (meth)acrylic polymer and a liquid material of a monomer, and the powder material and the liquid material is kneaded to thereby initiate polymerization, providing a cured product. The cured product of the denture restorative material such as the dental powder-liquid type acrylic material conventionally used, however, has been insufficient in bending strength of a polymer, and has not also been satisfactory in fillability in a restoration.

In case of filling a kneaded material of the denture restorative material such as the conventional dental powder-liquid type acrylic material in a restoration by use of a brush, the kneaded material of the denture restorative material is often released from the restoration and attached to the brush. Furthermore, a denture base mounted in an oral cavity absorbs moisture, and therefore, in case of repairing such a denture base, wettability between the denture restorative material and the denture base is insufficient to often cause peeling of the repaired portion.

A denture restorative material has been demanded in which, when a kneaded material of the denture restorative material is filled in a restoration by use of a brush, the kneaded product can be well released from the brush and easily filled in the restoration, and a cured product of the kneaded material of the denture restorative material can maintain an excellent bending property even in a state where moisture is excessive as in the oral environment and on an adherend that has absorbed water. Furthermore, a denture restorative material has been demanded in which, while an operation time required until the completion of filling in a restoration and repairing a dental crown after kneading of denture restorative material is secured, curing rapidly progresses after the completion of filling and repairing.

The dental composition of the present disclosure in case of a denture restorative material may be, for example, a dental composition containing component (a): monomer containing (meth)acrylamide group represented by formula (1),
component (c): monomer other than the component (a),
component (j): (meth) acrylic acid (co) polymer, and
component (f): polymerization catalyst, and
wherein a ratio of the component (a) in the total amount of the component (a) and the component (c) is within a range of 0.1 to 20 wt. %, and
wherein the component (f) contains at least one of a combination of a barbituric acid derivative and a halogen ion-forming compound and a combination of an organic peroxide and an amine compound.

That is, the dental composition of the present disclosure in case of a denture restorative material is a dental composition containing a monomer, a (meth) acrylic acid (co) polymer, and a polymerization catalyst, wherein the monomer includes component (a): monomer containing (meth) acrylamide group represented by formula (1), a ratio of the component (a): monomer containing (meth)acrylamide group represented by formula (1) in the total amount of the monomer is within a range of 0.1 to 20 wt. %, and the component (f) polymerization catalyst contains at least one of a combination of a barbituric acid derivative and a halogen ion-forming compound and a combination of an organic peroxide and an amine compound. The range is preferably within a range of 1 to 15 wt. %, and more preferably within a range of 2 to 10 wt. %.

In this case, it is preferable that the component (f) contains a combination of 1-cyclohexyl-5-propylbarbituric acid or 1-cyclohexyl-5-ethylbarbituric acid and trioctylmethylammonium chloride.

In this case, it is preferable that the component (f) further contains an organometal compound.

In this case, it is preferable that the dental composition is a powder-liquid type in which a powder material and a liquid material is kneaded to be used and the liquid material contains the component (a), the component (c), and trioctylmethylammonium chloride, and the powder material contains the component (j), and 1-cyclohexyl-5-propylbarbituric acid.

In this case, it is preferable that the powder material further contains component (b): filler.

The dental composition of the present disclosure can be well released from a brush, and easily filled in a restoration. In addition, the dental composition of the present disclosure can provide a kneaded product of a denture restorative material which can secure a time for appropriately conducting a dental treatment, can maintain an excellent bending property even in a state where moisture is excessive as in the oral environment and on an adherend that has absorbed water, and can be excellent in curability after curing and therefore can allow final finish such as polishing to be easily performed.

While a preparation and a repair of a temporary inlay, a crown and a bridge, which is a working in an oral cavity, is a working in the wet state, the dental composition of the present disclosure can provide a denture restorative material which exhibits excellent curability and is hardly deteriorated in terms of physical properties even in a prosthetic device prepared under such environment. Further, the dental composition of the present disclosure can provide a denture restorative material in which discoloration does not occur and reduction in bending strength and compression strength is reduced.

[Tooth Substance Adhesive Primer]

For example, the dental composition of the present disclosure may be a tooth substance adhesive primer. Since composite resins have remarkably improved in long-term durability and mechanical characteristics and also have characteristics such as fluorine sustained-release and X-ray contrast radiographic properties, composite resins have recently been used for functional and esthetic recovery of tooth substances when deficiency in the tooth substances is caused by the onset of dental caries or when there is a breakage or detachment of a dental crown restoration. Application of these composite resins has expanded to tooth face coating materials, fissure sealants, orthodontic bonding materials, and resin core materials. However, since these composite resins themselves do not have adhesive property not only to a tooth substance, but also to ceramics and metals, it is essential to use various adhesive materials in combination. It is required for the adhesive material to have excellent adhesive property to the tooth substances, particularly both an enamel containing an inorganic component such as hydroxyapatite as a main component and a dentin containing an organic component such as collagen as a main component.

In recent year, there have been a lot of proposals regarding sufficiently curing an adhesive layer by using a primer and a bonding material in combination to thereby improve dental adhesion.

However, low curability due to constituent components of the primer composition cannot be basically improved. Therefore, it is recognized that adhesive property to both of an enamel and a dentin as well as durability on adhesion are insufficient.

Since moisture-proofing is important in applying a tooth substance adhesive primer, a risk of an adhesive failure caused by the influence of moisture has been concerned in a clinical case where it is hard to achieve moisture-proofing.

There is a demand for the development of a tooth substance adhesive primer that exhibits adhesive property that firmly adheres to an enamel and a dentin and adhesive durability that can withstand even in a severe oral environment by exhibiting sufficient curability even in a state where moisture is excessive, without losing an excellent storage stability in which deterioration and change in quality are less likely to be caused by hydrolysis of constituent components due to the environmental temperature or acidity of the solution and one-pack type packaging is also possible.

The dental composition of the present disclosure in case of a tooth substance adhesive primer may be, for example, a dental composition containing component (a): monomer containing (meth)acrylamide group represented by formula (1),
component (k): acid group-containing monomer,
component (l): water,
component (m): water-soluble organic solvent, and
component (f): polymerization catalyst, and
wherein 0.1 to 20 parts by weight of the component (a) is contained with respect to 100 parts by weight of the total of the components of the dental composition excluding the component (a) and the component (f). The range is preferably within a range of 1 to 15 parts by weight, and more preferably within a range of 2 to 10 parts by weight.

That is, the dental composition of the present disclosure in case of a tooth substance adhesive primer is a dental composition containing an acid group-containing monomer, water, a water-soluble organic solvent, a polymerization catalyst and component (a): monomer containing (meth)acrylamide group represented by formula (1), wherein a ratio of the component (a): monomer containing (meth)acrylamide group represented by formula (1) with respect to 100 parts by weight of the total of the components of the dental composition excluding the component (a) and the component (f) is within a range of 0.1 to 20 parts by weight.

In this case, it is preferable that the component (k) contains component (n) inorganic acid group-containing monomer and component (o) organic acid group-containing monomer, and the component (n) contains phosphorus and/or sulfur.

In this case, it is preferable that the component (k) contains component (n) inorganic acid group-containing monomer and component (o) organic acid group-containing monomer, and the component (o) is a carboxylic acid group-containing monomer.

The dental composition of the present disclosure can provide a tooth substance adhesive primer that exhibits adhesive property that firmly adheres to an enamel and a dentin and adhesive durability that can withstand even in a severe oral environment by improving curability in a state where water is excessive, without losing an excellent storage stability in which deterioration and change in quality are less likely to by hydrolysis of constituent components due to the environmental temperature or acidity of the solution and one-pack type packaging is also possible.

[Dental Primer]

For example, the dental composition of the present disclosure may be a dental primer. In recent years, a dental crown restoration technique has been frequently used. In this technique, a tooth restoration which is prepared by cutting and machining an inorganic sintered body by using CAD/CAM technique is mounted in an oral cavity.

An inorganic sintered body is supplied in the form of moldings such as a block and a disk, and a tooth restoration such as a crown, an inlay and an onlay is prepared by cutting and machining the moldings by using CAD/CAM. The cut tooth restoration is adhered to a missing tooth in an oral cavity to recover the function of an oral cavity.

In addition, when the tooth restoration which restores in an oral cavity is damaged, re-restoration by a newly prepared tooth restoration or repair with composites using adhesive materials on a fracture surface may be performed.

In this repair, it is required to bond composite resin to a fracture surface of the tooth restoration. Therefore, a dental primer which reforms a fracture surface of the tooth restoration has been required.

Conventionally, the tooth restoration prepared by cutting and machining an inorganic sintered body is bonded to a repair site in an oral cavity by using a cement and/or an adhesive material after reforming the surface with a dental primer containing a silane coupling agent. However, in order to activate a silane coupling agent and to efficiently reform the surface of the tooth restoration, in the primer containing the silane coupling agent, it has been required to mix with an acidic water solution before use. The reason is that because a silane coupling agent cannot exist at a stable condition under the coexistence with the acidic component, preservation stability and shelf life stability worsen, and, as a result, the adhesive ability of the tooth restoration decreases. Therefore, it has been necessary that a silane coupling agent and an acidic component are contained in separate packing forms respectively. In addition, the dental primer containing a silane coupling agent has a problem with preservation stability and shelf life stability such as the decreasing of the adhesive ability of the tooth restoration over time, even in the condition that acidic component is not contained. In addition, since moisture-proofing is important in applying a dental primer, a risk of an adhesive failure caused by the influence of moisture has been concerned in a clinical case where it is hard to achieve moisture-proofing. Therefore, a dental primer exhibiting sufficient curability even on an adherend that has absorbed water and in a state where moisture is excessive, and having excellent preservation stability and shelf life stability, having excellent operability because the mixing with an acidic component is unnecessary before the use, and being able to modify the surface of the tooth restoration is required.

The dental composition of the present disclosure in case of a dental primer may be, for example, a dental composition containing component (a): monomer containing (meth)acrylamide group represented by formula (1),
component (p): organic solvent,
component (g): silane coupling agent, and
component (q): acid anhydride and/or weakly acidic compound.

That is, the dental composition of the present disclosure in case of a dental primer is a dental composition which is a dental primer for modifying a surface of a tooth restoration and contains an organic solvent, a silane coupling agent, an acid anhydride and/or a weakly acidic compound, and component (a): monomer containing (meth)acrylamide group represented by formula (1).

In the present specification, the term "weakly acidic compound" means an acidic compound having pH of 2 or more.

In this case, it is preferable that the component (a) is contained within a range of 0.1 to 20 wt. %. The range is more preferably within a range of 1 to 15 wt. %, and most preferably within a range of 2 to 10 wt. %.

In this case, it is preferable that the component (q) contains an anhydride of a carboxylic acid, a sulfonic acid, a nitric acid and/or a phosphoric acid.

In this case, it is preferable that the component (q) only contains an anhydride of a carboxylic acid.

In this case, it is preferable that component (l): water is not contained.

In this case, it is preferable that a strongly acidic compound is not contained. In the present specification, the term "strongly acidic compound" means an acidic compound having pH of less than 2.

In this case, a set comprising a dental primer and an adhesive material is provided. In this case, it is preferable that the adhesive material comprises a polymerizable monomer and a polymerization catalyst. It is preferable that the adhesive material comprises a filler. When the adhesive material comprises a filler, it is generally called as resin cement.

In this case, a set comprising a dental primer and a tooth restoration is provided. It is preferable that the tooth restoration comprises a polymerizable monomer, a polymerization catalyst and a filler.

In this case, it is preferable that a polymerizable monomer, a polymerization catalyst and/or a filler are contained in only one of the adhesive material or the tooth restoration.

In this case, it is preferable that a polymerization catalyst is not contained. The reason is that it is important in this case to modify the surface of an adhesive body and an adherend.

In this case, it is preferable that the dental primer modifying a surface of a tooth restoration prepared by cutting and machining an inorganic sintered body consists of the component (p): organic solvent, the component (g): silane coupling agent, the component (q): acid anhydride and/or weakly acidic compound and the component (a): monomer containing (meth)acrylamide group represented by formula (1).

The dental primer using the dental composition of the present disclosure may reform the surface of the tooth restoration and the tooth restoration which is reformed with the dental primer using the dental composition of the present disclosure may adhere to a composite resin via an adhesive material containing a polymerizable monomer. In particular, the tooth restoration modified with the dental primer using the dental composition of the present disclosure exhibits sufficient curability even on an adherend that has absorbed water and in a state where moisture is excessive, is excellent in adhesive durability, and can maintain the adhesion for a long term under the oral cavity environment. Furthermore, the dental primer using the dental composition of the present disclosure may extend a shelf life.

In recent years, CAD/CAM technique is introduced in the dental field, and a tooth restoration is prepared by cutting and machining a block and a disk which are an inorganic sintered body, and a restoration technique in which this tooth restoration is applied into an oral cavity has been used in a clinical. A surface of the tooth restoration cannot be reformed enough by the dental primer containing a silane coupling agent and having been used conventionally. Therefore, sufficient adhesive property of the tooth restoration is not obtained even if combined with a dental adhesive resin cement. However, by using the dental primer using the dental composition of the present disclosure, sufficient curability is exhibited even on an adherend that has absorbed water and in a state where moisture is excessive, and adhesive property and adhesive durability of the tooth restoration are increased.

Specifically, it becomes possible to exhibit sufficient curability even on an adherend that has absorbed water and in a state where moisture is excessive, and adhere in excellent adhesive durability by performing adhesion work in accordance with a technique type of an adhesive resin cement after application of the dental primer using the dental composition of the present disclosure to an inner surface of the tooth restoration which is prepared by cutting and machining an inorganic sintered body.

Further, on the cutting surface of the tooth restoration consisting of the cured composite resin, which is also the tooth restoration, an inorganic filler in the composite resin is exposed to the surface. Therefore, the same effect as that of the tooth restoration consisting of an inorganic sintered body may be obtained by the same handling as the tooth restoration consisting of the inorganic sintered body. Specifically, it becomes possible to exhibit sufficient curability even on an adherend that has absorbed water and in a state where moisture is excessive, and adhere excellent in adhesive durability by the work of repairing in accordance with technique types of an adhesive material and a composite resin after application of the dental primer using the dental composition of the present disclosure to a cutting surface of the composite resin.

In addition to these adhesive effects, the dental primer using the dental composition of the present disclosure has a long-term shelf life and is excellent in adhesive stability. The dental primer using the dental composition of the present disclosure has the same effect on porcelain.

[Dental Adhesive Composition]

For example, the dental composition of the present disclosure may be a dental adhesive composition. Recently, since composite resins have remarkably improved in long-term durability and mechanical characteristics and also have characteristics such as fluorine sustained-release and X-ray contrast radiographic properties, composite resins have recently been used for functional and esthetic recovery of tooth substances when deficiency in the tooth substances is caused by the onset of dental caries or when there is a breakage or detachment of a dental crown restoration. Application of these composite resins has expanded to tooth face coating materials, fissure sealants, orthodontic bonding materials, and resin core materials. However, since these composite resins themselves do not have adhesive property not only to a tooth substance, but also to ceramics and metals, it is essential to use various adhesive materials in combination. It is required for the adhesive material to have excellent adhesive property to the tooth substances, particularly both an enamel containing an inorganic component such as hydroxyapatite as a main component and a dentin containing an organic component such as collagen as a main component. In recently, there has been a problem in firmly adhesiveness to ceramics, metals, resins, composite resins, and glass ionomer cement.

In a conventional adhesive material, after subjecting tooth substance surfaces to a tooth surface treatment using a strong etching material such as phosphoric acid, the bonding material is applied to bond tooth substances with a composite resin.

The bonding method using the acid etching material exhibited sufficient adhesive property to an enamel as a result of formation of a roughened surface through decalcification of the acid etching material, and macroscopic mechanical fitting based on sufficient penetration and curing of the bonding material. In contrast, since a spongy collagen fiber is exposed to dentin as a result of decalcification of the acid etching material, the bonding material did not sufficiently penetrate into a collagen fiber and it was difficult to obtain sufficient adhesive property to dentin. However, various methods have also been developed to improve adhesion to dentin.

However, due to the poor physical properties of an adhesive material, it was not possible to obtain further substantial strength.

In recent years, the usage range of dental composite materials such as a dental composite resin has been expanding. However, the conventional dental adhesive composition has a defect in that it has poor curability in an environment containing moisture such as in the oral cavity. Therefore, there is a demand for the development of a dental adhesive composition that can exhibit sufficient curability even in the presence of water and exhibit adhesiveness that firmly adheres to an enamel and a dentin.

The dental composition of the present disclosure in case of a dental adhesive composition may be, for example, a dental composition containing component (a): monomer containing (meth)acrylamide group represented by formula (1), component (c): monomer other than the component (a), and component (f): polymerization catalyst, and wherein the component (a) is contained within a range of 0.1 to 20 wt. %.

That is, the dental composition of the present disclosure in case of a dental adhesive composition is a dental composition which is a dental adhesive composition using a primer compounded with an adhesive component and contains component (a): monomer containing (meth)acrylamide group represented by formula (1), a monomer, and a polymerization catalyst, wherein the component (a) is contained within a range of 0.1 to 20 wt. %. The ratio is preferably within a range of 0.1 to 15 wt. %, and more preferably within a range of 2 to 10 wt. %. When the ratio exceeds 20 wt. %, the polymerization of other monomers is prevented, which may adversely affect the adhesive property. On the other hand, when the ratio is less than 0.1 wt. %, no effect is confirmed in the adhesive property to the tooth substance.

In this case, it is preferable that component (r): hydrophilic monomer and component (s): hydrophobic monomer are further contained.

In this case, it is preferable that water and/or an organic solvent is not contained.

The dental composition of the present disclosure can provide a dental adhesive composition that can exhibit sufficient curability even in the presence of water and exhibit adhesive property that firmly adheres to an enamel and a dentin.

[Tooth Substance Adhesive Composition]

For example, the dental composition of the present disclosure may be a tooth substance adhesive composition. Recently, since composite resins have remarkably improved in long-term durability and mechanical characteristics and also have characteristics such as fluorine sustained-release and X-ray contrast radiographic properties, composite resins have recently been used for functional and esthetic recovery of tooth substances when deficiency in the tooth substances is caused by the onset of dental caries or when there is a breakage or detachment of a dental crown restoration. Application of these composite resins has expanded to tooth face coating materials, fissure sealants, orthodontic bonding materials, and resin core materials. However, since these composite resins themselves do not have adhesive property not only to a tooth substance, but also to ceramics and metals, it is essential to use various adhesive materials in combination. It is required for the adhesive material to have excellent adhesive property to the tooth substances, particularly both an enamel containing an inorganic component such as hydroxyapatite as a main component and a dentin containing an organic component such as collagen as a main component.

In a conventional adhesive material, after subjecting tooth substance surfaces to a tooth surface treatment using a strong etching material such as phosphoric acid, the bonding material is applied to bond tooth substances with a composite resin. However, a method for the tooth surface treatment using an acid etching material had a drawback such as complicated operation steps in which the acid applied on the tooth surface must be sufficiently removed by washing with water and the tooth surface dried.

The bonding method using the acid etching material showed sufficient adhesive property to an enamel as a result of formation of a roughened surface through decalcification of the acid etching material, and macroscopic mechanical fitting based on sufficient penetration and curing of the bonding material. In contrast, since a spongy collagen fiber is exposed to a dentin as a result of decalcification of the acid etching material, the bonding material did not sufficiently penetrate into a collagen fiber and it was difficult to obtain sufficient adhesive property.

In recent years, the usage range of dental composite materials such as a dental composite resin has been expanding. However, the conventional adhesive composition has a defect in that it has poor curability on a biological hard tissue having a high water content such as a tooth substance of a natural tooth such as an enamel or a dentin and therefore sufficient adhesive property to a biological hard tissue having a high water content is not obtained. Therefore, there is a demand for the development of a tooth substance adhesive composition that can exhibit adhesive property that firmly adheres to a tooth substance having a high water content, especially a dentin.

The dental composition of the present disclosure in case of a tooth substance adhesive composition may be, for example, a dental composition containing component (a): monomer containing (meth)acrylamide group represented by formula (1), component (i): acidic group-containing monomer, component (t): monomer other than the component (a) and the component (i), component (l): water and/or component (p): organic solvent, and component (f): polymerization catalyst, and wherein the component (a) is contained within a range of 0.1 to 20 wt. %.

That is, the dental composition of the present disclosure in case of a tooth substance adhesive composition is a dental composition containing component (a): monomer containing (meth)acrylamide group represented by formula (1), an acidic group-containing monomer, a monomer, water and/or an organic solvent, and polymerization catalyst, wherein the component (a) is contained within a range of 0.1 to 20 wt. %. The ratio is preferably within a range of 1 to 15 wt. %, and more preferably within a range of 2 to 10 wt. %. When the ratio exceeds 20 wt. %, the polymerization of other monomers is prevented, which may adversely affect the adhesive property. On the other hand, when the ratio is less than 0.1 wt. %, no effect is confirmed in the adhesive property to the tooth substance.

In this case, it is preferable that the component (t) contains component (r): hydrophilic monomer and component (s): hydrophobic monomer.

The dental composition of the present disclosure can provide a tooth substance adhesive composition that can exhibit adhesive property that firmly adheres even to a tooth substance having a high water content, under an environment containing moisture such as in the oral cavity, and on an adherend that has absorbed water.

[Dental Adhesive Resin Cement]

For example, the dental composition of the present disclosure may be a dental adhesive resin cement. The resin cement is highly required as an adhesive for a dental prosthesis restorative material exhibiting the aesthetic property, and the composition contains a filler consisting of an organic, inorganic and/or organic-inorganic composite material, and a polymerizable monomer or oligomer. A filling ratio of the filler is 50 wt. % or more in order to achieve a high material strength. In addition, it is possible to polymerize and set even in a portion where light does not reach, a dual-cure type has been mainly used, which has the chemical polymerization function in addition to the photopolymerization function.

For restoring tooth which have underwent a relatively large damage due to dental caries or the like, a procedure is generally used, in which a crown, a bridge, an inlay, an onlay and the like which is made of ceramics, composite resins or metal materials is adhered with the resin cement. In such the case, a pre-treatment agent, so called a primer, is used, in order to strengthen adhesive property of the resin cement to a dental hard tissue. Sufficient adhesive property and material strength thereof are required for such the resin cement. Otherwise, there is a possibility that the restoration may be dropped during a long period use under severe oral environment, and there is a risk that a clearance may be produced at an interface between the resin cement and the tooth substance, and bacteria may invade therefrom and adversely effect on dental pulp.

The dental hard tissue is composed of an enamel and a dentin, and adhesion of the resin cement to both of them is clinically required. The primer for pre-treating a tooth surface has been conventionally used prior to application of the resin cement for enhancing adhesive property. Such the primer demineralizes the tooth surface to make it rough, and facilitating infiltration of the resin cement into a fine rough surface. An adhesion mechanism that, thereafter, the resin cement is set by chemical polymerization or photopolymerization is considered.

On the other hand, as the conventional resin cement, a powder-liquid type has been used, but a resin cement which is used by mixing two pre-pasted compositions has been highly required in order to avoid a cumbersome procedure of mixing the powder and the liquid. Such the procedure of mixing the pastes reduces a mixing time and a difference between persons as compared with the procedure of mixing the powder and the liquid and, therefore, is a preferable type for clinicians. Moreover, in addition to by photopolymerization, the polymerization setting function by chemical polymerization, i.e. the dual cure polymerization setting function, is required for such the resin cement, so that it may be used for a high light-transmittable prosthesis restorative material such as a dental porcelain, in addition to a low light-transmittable prosthesis restorative material such as a dental alloy.

However, prior to adhesion with the resin cement, each adherend of a tooth substance, a ceramic, a composite resin and metal should be treated with an exclusive primer for each of various adherends in advance. Clinically, a simple adhesion procedure is desired, which does not require a primer treatment for such various adherends.

Further, in recent years, the usage range of dental composite materials such as a dental composite resin has been expanding. However, the conventional dental resin cement has a defect in that it has poor curability on a biological hard tissue having a high water content such as a tooth substance of a natural tooth such as an enamel or a dentin, in an environment containing moisture, such as in the oral cavity, or on an adherend that has absorbed water and therefore sufficient adhesive property is not obtained. Therefore, there is a demand for the development of a dental adhesive resin cement that can exhibit adhesive property that firmly adheres even to a tooth substance having a high water content, under an environment containing moisture such as in the oral cavity, and on an adherend that has absorbed water.

The dental composition of the present disclosure in case of a dental adhesive resin cement may be, for example, a dental composition containing component (a): monomer containing (meth)acrylamide group represented by formula (1),
component (b): filler,
component (i): acidic group-containing monomer,
component (u): sulfur atom-containing monomer,
component (g): silane coupling agent,
component (d): polymerization initiator, and
component (v): monomer other than the component (a), the component (i) and the component (u), and
wherein the component (a) is contained within a range of 0.1 to 20 wt. %.

That is, the dental composition of the present disclosure in case of a dental adhesive resin cement contains a monomer, a filler, component (a): monomer containing (meth)acrylamide group represented by formula (1), an acidic group-containing monomer, a sulfur atom-containing monomer, a silane coupling agent, and polymerization initiator, wherein the component (a) is contained within a range of 0.1 to 20 wt. %. The ratio is preferably within a range of 1 to 15 wt. %, and more preferably within a range of 2 to 10 wt. %. When the ratio exceeds 20 wt. %, the polymerization of other monomers is prevented, which may adversely affect the adhesive property. On the other hand, when the ratio is less than 0.1 wt. %, no effect is confirmed in the adhesive property to the tooth substance.

The dental composition of the present disclosure can provide a dental adhesive resin cement that can exhibit adhesive property that firmly adheres even to a tooth substance having a high water content, under an environment containing moisture such as in the oral cavity, and on an adherend that has absorbed water.

[Self-Adhesive Dental Composite Resin]

For example, the dental composition of the present disclosure may be a self-adhesive dental composite resin. In dental clinics, a composite resin restoration in which a caries caused in a tooth is removed to form a cavity to be thereafter filled with a resin-based filling restoring material is widely used. The composite resin restoration is characterized by reproducing an aesthetic state similar to that of the natural tooth and allowing a treatment to be completed with only one dental visit to reduce a burden on the patient.

The resin-based filling/restoring material itself does not have an adhesive property to tooth. Therefore, in a restoration using this material, it is essential to applicate a dental adhesion system. The dental adhesion system acts on the enamel and the dentin of the tooth to be interposed between the resin-based filling/restoring material and the tooth to stably bond the material and the tooth to each other. Two types of dental adhesion systems are currently available in the market: one (a total-etching type dental adhesion system) involves an etching process in which a phosphoric acid is used as a pre-treatment for the tooth, and the other (a self-etching type dental adhesion system) involves a self-etching process for the tooth in which a tooth substance primer containing a polymerizable monomer having an acidic group is used and no water washing is required.

In recent years, the usage range of dental composite materials such as a dental composite resin has been expanding. However, the conventional dental composite resin has a defect in that it has poor curability on a biological hard tissue having a high water content such as a tooth substance of a natural tooth such as an enamel or a dentin and therefore sufficient self-adhesive property to a biological hard tissue having a high water content is not obtained. Therefore, there is a demand for the development of a dental composite resin that can exhibit self-adhesive property that firmly adheres to a tooth substance having a high water content, especially a dentin.

The dental composition of the present disclosure in case of a self-adhesive dental composite resin may be, for example, a dental composition containing component (a): monomer containing (meth)acrylamide group represented by formula (1), component (i): acidic group-containing monomer,
component (w): photopolymerization catalyst, and
component (b): filler, and
wherein the component (a) is contained within a range of 0.1 to 20 wt. %.

That is, the dental composition of the present disclosure in case of a self-adhesive dental composite resin contains component (a): monomer containing (meth)acrylamide group represented by formula (1), an acidic group-containing monomer, a photopolymerization catalyst, and a filler and wherein the component (a) is contained within a range of 0.1 to 20 wt. %. The ratio is preferably within a range of 1 to 15 wt. %, and more preferably within a range of 2 to 10 wt. %. When the ratio exceeds 20 wt. %, the polymerization of other monomers is prevented, which may adversely affect the adhesive property. On the other hand, when the ratio is less than 0.1 wt. %, no effect is confirmed in the adhesive property to the tooth substance.

In this case, it is preferable that component (r): hydrophilic monomer is further contained.

In this case, it is preferable that component (s): hydrophobic monomer is further contained.

The dental composition of the present disclosure can provide a self-adhesive dental composite resin that exhibit a self-adhesive property firmly adheres to a tooth substance having a high water content, especially a dentin without excessive drying.

[Adhesive Composition]

For example, the dental composition of the present disclosure may be an adhesive composition. Since composite resins have remarkably improved in long-term durability and mechanical characteristics and also have characteristics such as fluorine sustained-release and X-ray contrast radiographic properties, the composite resins have recently been used for functional and esthetic recovery of tooth substances when deficiency in the tooth substances is caused by the onset of dental caries or when there is a breakage or detachment of a dental crown restoration. Application of these composite resins has expanded to tooth face coating materials, fissure sealants, orthodontic bonding materials, and resin core materials. However, since these composite resins themselves do not have adhesive property not only to a tooth substance, but also to ceramics, it is essential to use various adhesive materials in combination. In recently, there has been a problem in firmly adhesiveness to ceramics, resins, composite resins, and glass ionomer cement and adhesive durability.

In recent years, the usage range of dental composite materials such as a dental composite resin has been expanding. However, the conventional adhesive composition has a defect in that it has poor curability in an environment containing moisture, such as in the oral cavity, or on an adherend that has absorbed water and therefore sufficient adhesive property is not obtained. Therefore, there is a demand for the development of an adhesive composition that can exhibit sufficient curability even in a state where moisture is excessive such as in the oral cavity or on an adherend that has absorbed water, firmly adhesiveness, and adhesive durability that can withstand even in a severe oral environment.

The dental composition of the present disclosure in case of an adhesive composition may be, for example, a dental composition containing component (a): monomer containing (meth)acrylamide group represented by formula (1),
component (r): hydrophilic monomer,
component (s): hydrophobic monomer,
component (f): polymerization catalyst,
component (q): acid anhydride and/or weakly acidic compound, and
component (g): silane coupling agent, and
wherein the component (a) is contained within a range of 0.1 to 20 wt. %.

That is, the dental composition of the present disclosure in case of an adhesive composition contains component (a): monomer containing (meth)acrylamide group represented by formula (1), a hydrophilic monomer, a hydrophobic monomer, a polymerization catalyst, an acid anhydride and/or a weakly acidic compound, and a silane coupling agent, and wherein the component (a) is contained within a range of 0.1 to 20 wt. %. The ratio is preferably within a range of 1 to 15 wt. %, and more preferably within a range of 2 to 10 wt. %. When the ratio exceeds 20 wt. %, the polymerization of other monomers is prevented, which may adversely affect the adhesive property. On the other hand, when the ratio is less than 0.1 wt. %, no effect is confirmed in the adhesive property to the tooth substance.

In this case, it is preferable that component (l): water and/or component (p): organic solvent are not contained.

The dental composition of the present disclosure can provide an adhesive composition that can exhibit sufficient curability even in an environment containing moisture, such as in the oral cavity and on an adherend that has absorbed water, firmly adhesiveness, and adhesive durability that can withstand even in a severe oral environment.

Hereinafter, each components in the dental composition of the present disclosure is described in detail.

The component (b): filler used in the dental composition of the present disclosure in case of the dental composite material composition is not particularly limited, and a filler known in the art such as an inorganic filler and/or an organic filler and/or an organic-inorganic composite filler, for example, may be used without any limitation. The grain shape of the filler may be any shape such as a sphere, a massive, a needle, a plate, a fracture, a scale, but is not specifically limited. In order to achieve more stability of a paste, the filler preferably has a spherical shape. The degree of circularity indicating the spherical shape of the filler is preferably within a range of 0.7 to 1.0, more preferably within a range of 0.9 to 1.0, further preferably within a range of 0.95 to 1.00.

With respect to the calculation method of the degree of circularity, the degree of circularity can be determined by processing an image taken by an optical microscope or a scanning electron microscope (hereinafter, referred to as SEM) by use of an image analysis apparatus. The number of samples to be image-processed is 50 or more, and the degree of circularity is calculated from the area of the filler and the boundary length of the filler. The degree of circularity $e=(4 \times \pi \times S)/(L^2)$ is calculated with boundary lengths (L) and area (S) of the fillers, which are obtained by analyzing the image.

Specific examples of the inorganic filler include quartz, amorphous silica, aluminum silicate, aluminum oxide, titanium oxide, zirconium oxide, various glasses (including a glass by a melting method, a synthetic glass by a sol-gel method, and a glass produced by a gas phase reaction), calcium carbonate, talc, kaolin, clay, mica, aluminum sulfate, calcium sulfate, barium sulfate, calcium phosphate, hydroxyapatite, silicon nitride, aluminum nitride, titanium nitride, silicon carbide, boron carbide, calcium hydroxide, strontium hydroxide and zeolite. Among them, an aluminosilicate glass, borosilicate, aluminoborate and boroaluminosilicate glasses, and the like including sodium, strontium, barium, a heavy metal such as lanthanum, and/or fluorine are preferable. The average particle diameter of such an inorganic filler is not particularly limited, and is preferably within a range of 0.5 to 10 μm, more preferably within a range of 0.7 to 5 μm.

An ultrafine particle inorganic filler such as Aerosil produced by a gas phase method or a silica-zirconia oxide particle produced in a solution of a sol-gel reaction or the like can be used as component (e): fine particle filler. A cohesive inorganic filler in which such ultrafine particles aggregate, or the like is also used without any problem. In kneading of a composite material, when the cohesive inorganic filler is crushed so as to have an average particle diameter of 1 nm to 300 nm, it is classified into the ultrafine particle inorganic filler, and when the cohesive inorganic filler is not crushed so as to have an average particle diameter of 1 nm to 300 nm, it is classified into the inorganic filler.

The average particle diameter of an ultrafine particulate inorganic filler is from 1 nm to 300 nm. The ultrafine particle inorganic filler is, but not limited, preferably colloidal silica (product name: Aerosil R972, Aerosil 200, Aerosil 380 or Aerosil 50 manufactured by Nippon Aerosil Co., Ltd., 5 to 50 nm).

For example, a fluoroaluminosilicate glass filler which is a known inorganic filler may be prepared by the known glass preparing method, and is preferably prepared by a fusion method or a sol-gel method.

The fusion method may include, for example, melting a glass raw material selected from the group consisting of silica, alumina, aluminum hydroxide, aluminum silicate, mullite, calcium silicate, strontium silicate, sodium silicate, sodium carbonate, calcium fluoride, aluminum fluoride, strontium silicate, aluminum phosphate, sodium phosphate and the like, at a high temperature of not lower than 1000° C., followed by cooling and crushing to prepare the glass filler.

Following composition is preferable as the composition of a fluoroaluminosilicate glass that may be used in the resin cement of the present disclosure

TABLE 1

| | | |
|---|---|---|
| Calcium oxide | (CaO) | 0 to 40 mol % |
| Silica | (SiO$_2$) | 15 to 70 mol % |
| Almina | (Al$_2$O$_3$) | 10 to 50 mol % |
| Sodium oxide | (Na$_2$O) | 0 to 7 mol % |
| Phosphorus pentoxide | (P$_2$O$_5$) | 0 to 20 mol % |
| Strontium oxide | (SrO) | 0 to 40 mol % |
| Zinc oxide | (ZnO) | 0 to 20 mol % |

An amount of fluorine contained in such the glass is preferably 5 to 60 mol %.

Although calcium oxide is contained in above composition, any alkaline earth metal oxide may be used. At least a part of the alkaline earth metal may be substituted with a lanthanide metal such as lanthanum, gadolinium, ytterbium and the like. Moreover, a part or all of alumina in such the glass may be substituted with III-group metals other than aluminum. In a similar manner, a part of silica in the glass may be substituted with zirconium oxide or titanium oxide. When the glass contains strontium, lanthanum, gadolinium, ytterbium or zirconium, it becomes X-ray opaque.

In addition, the sol-gel method may include, for example, reacting a first solution containing a soluble aluminum compound and a soluble silicon compound with a second solution containing a soluble compound of II-group metals to obtain a gel, and drying the gel by heat drying or freeze drying and collecting it. When this method is used, use of an additive conventionally used for production of glass such as a flux can be avoided, and a relatively low temperature can be used. From this reason, a glass having higher transparency than that of the conventional glass can be obtained.

Moreover, a glass containing a divalent or trivalent metal ion may be obtained by adding other compounds such as an alcohol solution of organic metal salts or inorganic salts in a sol state.

Moreover, an acidic or basic solvent may be added to this sol-gel reaction mixture in order to promote a gelation speed. This method affords a homogeneous fire-resistant glass at a relatively low temperature.

This sol-gel method is particularly suitable for preparation of a glass into which gadolinium is introduced or a glass consisting of the following five components:
XnOm—CaO—Al$_2$O$_3$—SiO$_2$—F (wherein, XnOm is an oxide of the X-ray opaque materials, for example, Gd$_2$O$_3$).

Such a five component glass is difficult to prepare. However, the sol-gel method allows for easy preparing of such the glass. A source of CaO may be replaced by aluminium sec-butoxide in isobutyl alcohol and ethanol, a source of SiO$_2$ may be replaced by tetraethyl silicate, an source of F may be replaced by 40% hydrofluoric acid, and a source of Gd$_2$O$_3$ may be replaced by ethanol-soluble Gd(NO$_3$)$_3$ or a methanol solution thereof.

Further, calcium oxide may be replaced by Ca(NO$_3$)$_2$ anhydride dissolved in ethanol at 50° C. These solutions are mixed at 50° C. by stirring. The mixture may be then refluxed at 70° C. After drying, the obtained material is ground while it is soft and then the ground material is dried at a temperature between 400 to 500° C. Then, this material is further pulverized into a required size.

The organic filler can be obtained by polymerizing a monomer having a polymerizable group, and the type thereof is not particularly limited. Specific examples of the organic filler include unsaturated aromatics such as polym- ethyl methacrylate, styrene, α-methylstyrene, halogenated styrene and divinylbenzene; unsaturated esters such as vinyl acetate and vinyl propionate; unsaturated nitriles such as acrylonitrile and the like; (co)polymer prepared by (co) polymerizing monomers having a polymerizable group such as butadiene and isoprene alone or in plural. The later-mentioned monomer having a polymerizable group, already known in the dental field, is particularly preferable. The method for preparing the organic filler is not particularly limited, and any method such as emulsion polymerization, suspension polymerization or dispersion polymerization of the monomer having a polymerizable group, or a method for pulverizing a polymer bulk previously produced can also be conducted.

An organic-inorganic composite filler in which an organic polymer contains an inorganic particle can also be used. The inorganic particles to be contained in the organic polymer are not specifically limited, and those known in the art may be used. Examples of the inorganic particles include particles of the inorganic fillers discussed above. The method for preparing the organic-inorganic composite filler is not particularly limited, and any method can also be adopted. Examples include a method including subjecting the surface of the inorganic particle to microencapsulation or grafting by an organic substance, a method including introducing a polymerizable functional group or a polymerizable initiation group to the surface of the inorganic particle and then subjecting the resultant to radical polymerization, and a method including pulverizing a polymer bulk including the inorganic particle, previously produced. Such inorganic, organic and organic-inorganic composite fillers can be each used singly or in combinations of several types.

Preferably, the average particle diameter of the organic filler and the organic-inorganic composite filler is within a range of 1 to 100 μm. More preferably, the average particle diameter thereof is within a range of 3 to 50 μm and, yet more preferably, is within a range of 5 to 30 μm. Such inorganic, organic and organic-inorganic composite fillers can be each used singly or in combinations of several types.

After the surfaces of the particles of the filler, such as the inorganic, organic, or organic-inorganic composite filler, are treated by a method known in the art, the filler can be used for the dental composition as the dental composite material composition. For example, the surface treatment may be performed using a surfactant, a fatty acid, an organic acid, an inorganic acid, a silane coupling agent, a titanate coupling agent, polysiloxane, or the like. These surface treatment methods are preferable because the wettability between the resin component and the surface of the filler is improved and the dental composition as the dental composite material composition is imparted with superior properties. The surface treatment method may be selected as appropriate according to the required properties. The filler surface is subjected to a surface treatment by a special surface treatment agent and/or a special surface treatment method for the purpose of multi-functionalizing the filler, without any limitation.

A silanated filler provided by a silanation step in which a filler is treated with a component (g): silane coupling agent is preferably used. Further, the silanated filler is preferably provided through a silanated filler preserving step in which a silanated filler is preserved for a predetermined period.

As the silane coupling agent, there can be preferably used, not particularly limited, methyltrimethoxysilane, methyltriethoxysilane, methyltrichlorosilane, dimethyldichlorosilane, trimethylchlorosilane, hexamethyldisilazane, vinyltrimethoxysilane, vinyltriethoxysilane, vinyltrichlorosilane, vinyltriacetoxysilane, vinyltris(β-methoxyethoxy) silane, γ-methacryloyloxypropyltrimethoxysilane, γ-methacryloxypropyltris (β-methoxyethoxy)silane, γ-chloropropyltrimethoxysilane, γ-chloropropylmethyldimethoxysilane, γ-glycidoxypropyltrimethoxysilane, γ-glycidoxypropylmethyldiethoxysilane, β-(3,4-epoxycyclohexyl)ethyltrimethoxysilane, N-phenyl-γ-aminopropyltrimethoxysilane and hexamethyldisilazane. Particularly preferably, methyltrichlorosilane, dimethyldichlorosilane and hexamethyldisilazane are used.

An organic solvent is preferably a volatile water-soluble organic solvent. As the volatile water-soluble organic solvent, there can be exemplified methanol, ethanol, n-propanol, isopropyl alcohol, acetone, methyl ethyl ketone and the like. As required, these organic solvents can be used in a plural kinds being mixed together. By taking toxicity to living body into consideration, it is desired to use ethanol, isopropyl alcohol and acetone.

A proportion of the component (b) filler in a dental composition in case of the dental composite material composition may be optionally selected depending upon a material property required for a composite material. An filling amount of low-viscous materials such as sealants, bonding materials, primers, tooth surface treating agents, opacifying agents and cements generally used in the dental field should be set at a relatively small level since higher fluidity required as material property is required for these materials. Therefore, the content is preferably within a range of 5.0 to 80.0 parts by weight, more preferably within a range of 30.0 to 70.0 parts by weight relative to the whole component of a dental composition as the dental composite material composition. In addition, a filling amount of high-viscous materials such as a composite resin and a veneer crown resin should be set at a relatively high level since, as the required material property, such the shapability is required that does not cause deformation after shape adjustment. Accordingly, the content is preferably within a range of 50.0 to 98.0 parts by weight, more preferably within a range of 75.0 to 98.0 parts by weight relative to the whole component of a dental composition as the dental composite material composition.

The component (c): monomer other than the component (a) used in case that the dental composition of the present disclosure is the dental composite material composition is not limited, but examples thereof include known monofunctional and/or multifunctional polymerizable monomer(s) commonly used for a dental composite material. Preferable monomers include monomers having an acryloyl and/or methacryloyl group. Next, the names of specific monomer are described.

Examples of the (meth)acrylic acid group-containing monomer include: monofunctional monomers (uncrosslinkable monomers): (meth)acrylates such as methyl (meth)acrylate, ethyl (meth)acrylate, butyl (meth)acrylate, hexyl (meth)acrylate, tetrahydrofurfuryl (meth)acrylate, 2-hydroxyethyl (meth)acrylate, glycidyl (meth)acrylate, lauryl (meth)acrylate, cyclohexyl (meth)acrylate, benzyl (meth)acrylate, allyl (meth)acrylate, 2-ethoxyethyl (meth)acrylate, methoxypolyethylene glycol (meth)acrylate, glycerol (meth)acrylate and isobonyl (meth)acrylate; silane compounds such as γ-(meth)acryloyloxypropyltrimethoxysilane and γ-(meth)acryloyloxypropyltriethoxysilane; and nitrogen-containing compounds such as 2-(N,N-dimethylamino)ethyl (meth)acrylate, N-methylol (meth)acrylamide and diacetone (meth)acrylamide, aromatic bifunctional monomers (crosslinkable monomers): 2,2-bis(4-(meth)acryloyloxyphenyl) propane, 2,2-bis(4-(3-(meth)acryloyloxy-2-hydroxypropoxy)phenyl)propane, 2,2-bis(4-(meth) acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2(4-(meth)acryloyloxyethoxyphenyl)-2(4-(meth)acryloyloxydiethoxyphenyl)propane, 2(4-(meth)acryloyloxydiethoxyphenyl)-2(4-(meth)acryloyloxytriethoxyphenyl)propane, 2(4-(meth)acryloyloxydipropoxyphenyl)-2(4-(meth)acryloyloxytriethoxyphenyl)propane, 2,2-bis(4-(meth)acryloyloxydipropoxyphenyl)propane and 2,2-bis(4-(meth)acryloyloxyisopropoxyphenyl)propane, aliphatic bifunctional monomers (crosslinkable monomers): 2-hydroxy-3-acryloyloxypropyl methacrylate, hydroxypivalic acid neopentyl glycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth)acrylate, propylene glycol di(meth)acrylate, 1,3-butanediol di(meth)acrylate, 1,4-butanediol di(meth)acrylate, 1,6-hexanediol di(meth)acrylate and glycerin di(meth)acrylate, trifunctional monomers (crosslinkable monomers): trimethylolpropane tri(meth)acrylate, trimethylolethane tri(meth)acrylate, trimethylolmethane tri(meth)acrylate and pentaerythritol tri(meth)acrylate, and tetrafunctional monomers (crosslinkable monomers): such as pentaerythritol tetra(meth)acrylate and ditrimethylolporpane tetra (meth)acrylate.

Examples of a urethane-based monomer include di(meth)acrylates having a bifunctional or tri- or higher functional urethane bond, derived from an adduct of a hydroxyl group-containing monomer such as 2-hydroxyethyl (meth)acrylate, 2-hydroxypropyl (meth)acrylate or 3-chloro-2-hydroxypropyl (meth)acrylate and a diisocyanate compound such as methylcyclohexane diisocyanate, methylenebis(4-cyclohexylisocyanate), hexamethylene diisocyanate, trimethylhexamethylene diisocyanate, isophorone diisocyanate, diisocyanate methyl methylbenzene or 4,4-diphenylmethane diisocyanate.

A monomer other than the above described the (meth)acrylate-based monomer, for example, a monomer, an oligomer or a polymer having at least one polymerizable group in the molecule may be used for the component (c): monomer other than the component (a) used in case that the dental composition of the present disclosure is the dental composite material composition, in accordance with purpose. The component (c): monomer other than the component (a) may have a substituent such as an acidic group and a fluoro group in the molecule. The component (c): monomer other than the component (a) may be a single component, or may be a mixture of a plurality of monomers. When the viscosity of the monomer is extremely high at room temperature or the monomer is a solid, the monomer is preferably combined with a monomer low in viscosity and used as a polymerizable monomer mixture. In such a combination, the monomer may be used in combinations of two, or three or more.

The component (c): monomer other than the component (a) may include only monofunctional monomers, and may additionally include polyfunctional monomers. Preferable monomers include an aromatic compound of a bifunctional monomer and an aliphatic compound of a bifunctional polymerizable monomer. More preferable monomers include 2,2-bis(4-(3-methacryloyloxy-2-hydroxypropoxy)phenyl)propane (Bis-GMA) and triethylene glycol dimethacrylate (TEGDMA).

In case that the dental composition is the dental composite material composition, the component (c): monomer other than the component (a) may contain component (i): acidic group-containing monomer containing an acid group such as phosphoric acid group, carboxylic acid group, phosphonic acid, sulfonic acid group or the like in the molecule as a part or the whole of the monomer in order to impart adhesive property to tooth substance or base metals to the dental composition as the dental composite material composition. Further, in order to improve the adhesive property for a noble metal, the component (c): monomer other than the component (a) may include component (u): sulfur atom-containing monomer containing a sulfur atom in the molecule.

It is preferable that the content of the monomer containing an acid group such as a phosphoric acid group, a carboxylic acid group, a phosphonic acid, a sulfonic acid group or the like in the molecule or the monomer containing sulfur atom in the molecule is preferably 0.5 to 20 wt. % based on 100% of the whole monomer.

Specific examples of the above described monomer include carboxylic acid group-containing monomer: (meth)acrylic acid, 1,4-di(meth)acryloyloxyethylpyromellitic acid, 6-(meth)acryloyloxynaphthalene-1,2,6-tricarboxylic acid, N-(meth)acryloyl-p-aminobenzoic acid, N-(meth)acryloyl-5-aminosalicylic acid, 4-(meth)acryloyloxyethyltrimellitic acid and anhydride thereof, 4-(meth)acryloyloxybutyltrimellitic acid and anhydride thereof, 2-(meth)acryloyloxybenzoic acid, β-(meth)acryloyloxyethyl hydrogen succinate, β-(meth)acryloyloxyethyl hydrogen maleate, 11-(meth)acryloyloxy-1,1-undecanedicarboxylic acid and p-vinylbenzoic acid, phosphoric acid group-containing monomer: 2-(meth)acryloyloxyethyl dihydrogen phosphate, 3-(meth)acryloyloxypropyl dihydrogen phosphate, 10-(meth)acryloyloxydecyl dihydrogen phosphate, bis(2-(meth)acryloyloxyethyl) hydrogen phosphate and 2-(meth)acryloyloxyethylphenyl hydrogen phosphate, sulfonic acid group-containing monomer: 2-(meth)acrylamide-2-methylpropanesulfonic acid, 4-(meth)acryloyloxybenzenesulfonic acid and 3-(meth)acryloyloxypropanesulfonic acid, and component (u): sulfur atom-containing monomer: (meth)acrylate having a triazinethiol group, (meth)acrylate having a mercapto group, (meth)acrylate having a polysulfide group, (meth)acrylate having a thiophosphoric acid group, (meth)acrylate having a disulfide cyclic group, (meth)acrylate having a mercaptodithiazol group, (meth)acrylate having a thiouracil group and (meth)acrylate having a thiirane group.

These monomers may be used singly or as a mixture of two or more.

In order to obtain high physical properties in the dental composition as the dental composite material composition of the present disclosure, it is preferable that the component (i): acidic group-containing monomer is not contained.

The dental composition as the dental composite material composition may contain component (r): hydrophilic monomer. The component (r): hydrophilic monomer has the effect of enhancing adhesive property by improving permeability and wettability to an interface to be adhered by compounding in the dental composition as the dental composite material composition. In the case the dental composition is the dental composite material composition, as the hydrophilic monomer, a monofunctional or polyfunctional monomer which exhibits hydrophilicity can be used without any limitation, regardless of the kind of a radical polymerizable unsaturated group, as long as the monomer does not correspond to the component (a). Examples of the radical polymerizable unsaturated group of the hydrophilic monomer include (meth)acryloyl group, styryl group, vinyl group, and allyl group. It is particularly preferred to use a hydrophilic monomer having a (meth)acryloyl group as an unsaturated group. The hydrophilic monomer which exhibits hydrophilicity can also have another functional group such as acidic group including carboxyl group, phosphoric acid group, phosphonic acid group and sulfonic acid group and the like, alkyl group, halogen, amino group, glycidyl group and hydroxyl group in the molecule.

Regarding the "hydrophilic monomer" as used herein, a monomer having solubility in 100 parts by weight of water at 23° C. of 10 parts by weight or more is defined as a hydrophilic monomer. That is, 10 g of a monomer is added to 100 g of water kept at 23° C. in a sample bottle, and the mixture is stirred for 10 minutes to thereafter be left to stand. After the lapse of 10 minutes, the mixture in the sample bottle is observed. If the mixture is dissolved uniformly transparently or translucently, the monomer is determined as a hydrophilic monomer.

Specific examples of the hydrophilic monomer in which a radical polymerizable unsaturated group is a (meth)acryloyl group among the hydrophilic monomer include, but are not limited to, 2-hydroxyethyl (meth)acrylate, 2-hydroxypropyl (meth)acrylate, 3-hydroxypropyl (meth)acrylate, 1,2-dihydroxypropyl (meth)acrylate, 1,3-dihydroxypropyl (meth)acrylate, 2,3-dihydroxypropyl (meth)acrylate, 2-hydroxypropyl-1,3-di(meth)acrylate, 3-hydroxypropyl-1,2-di(meth)acrylate, pentaerythritol di(meth)acrylate, 2-trimethylammonium ethyl(meth)acrylchloride, (meth)acrylamide, 2-hydroxyethyl(meth)acrylamide, and polyethylene glycol di(meth)acrylate (those having 9 or more oxyethylene groups), but are not limited to. These Hydrophilic monomer may be the used alone or in combination of two or more thereof.

Among these hydrophilic monomers, those which resolve in an amount of 20 parts by weight or more in 100 parts by weight of water at 23° C. are preferable, and those which resolve in an amount of 40 parts by weight or more in 100 parts by weight of water at 23° C. are more preferable. Specific examples thereof include 2-hydroxyethyl (meth)acrylate, polyethylene glycol di(meth)acrylate (having 9 oxyethylene groups), polyethylene glycol di(meth)acrylate (number of oxyethylene groups 14), polyethylene glycol di(meth)acrylate (having 23 oxyethylene groups), and the like.

The amount of the hydrophilic monomer compounded in a dental composition as a dental composite material composition is preferably 10 to 90 parts by weight, more preferably 20 to 60 parts by weight based on 100 parts by weight of the total weight of the component (r): hydrophilic monomer and the component (s): hydrophobic monomer contained in the dental composition as the dental composite material composition. When the content deviates from the above range, wettability to the surface of the adherend to be adhered deteriorates and polymerizability is deteriorated, and thus adhesive property deteriorate.

The dental composition as the dental composite material composition may contain component (s): hydrophobic monomer. As the component (s): hydrophobic monomer, a monofunctional or polyfunctional monomer which exhibits hydrophobicity can be used without any limitation, regardless of the kind of a radical polymerizable unsaturated group, as long as the monomer does not correspond to the component (a). Examples of the radical polymerizable unsaturated group of the hydrophobic monomer include (meth)acryloyl group, (meth)acrylamide group, styryl group, vinyl group, and allyl group. It is particularly preferred to use a hydrophobic monomer having a (meth) acryloyl group or (meth)acrylamide group as an unsaturated group. The hydrophobic monomer which exhibits hydrophobicity can also have another functional group such as acidic group including carboxyl group, phosphoric acid group, phosphonic acid group and sulfonic acid group and the like, alkyl group, halogen, amino group, glycidyl group and hydroxyl group in the molecule.

Regarding the "hydrophobic monomer" as used herein, a monomer having solubility in 100 parts by weight of water at 23° C. of less than 10 parts by weight is defined as a hydrophobic monomer. That is, 10 g of a monomer is added to 100 g of water kept at 23° C. in a sample bottle, and the mixture is stirred for 10 minutes to thereafter be left to stand. After the lapse of 10 minutes, the mixture in the sample bottle is observed. If the mixture is separated into phases in the sample bottle, the polymerizable monomer is defined as a hydrophobic monomer.

Specific examples of the hydrophobic monomer in which a radical polymerizable unsaturated group is a (meth)acryloyl group among the hydrophobic monomer include monofunctional group-containing hydrophobic monomer, for example, (meth)acrylate esters such as methyl (meth)acrylate, ethyl (meth)acrylate, butyl (meth)acrylate, hexyl (meth)acrylate, tetrahydrofurfuryl (meth)acrylate, glycidyl (meth)acrylate, lauryl (meth)acrylate, cyclohexyl (meth)acrylate, benzyl (meth)acrylate, allyl (meth)acrylate, 2-ethoxyethyl (meth)acrylate, methoxypolyethylene glycol (meth)acrylate, and isobonyl (meth)acrylate; silane compounds such as γ-(meth)acryloyloxypropyltrimethoxysilane and γ-(meth) acryloyloxypropyltriethoxysilane; and nitrogen-containing compounds such as 2-(N,N-dimethylamino)ethyl (meth) acrylate.

Examples of the aromatic difunctional group-containing hydrophobic polymerizable monomer include 2,2-bis(4-(meth)acryloyloxyphenyl)propane, 2,2-bis(4-(3-(meth)acryloyloxy-2-hydroxypropoxy)phenyl) propane, 2,2-bis(4-(meth)acryloyloxyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxyethoxyphenyl)-2-(4-(meth)acryloyloxydiethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propan e, 2,2-bis(4-(meth)acryloyloxydipropoxyphenyl)propane, and 2,2-bis(4-(meth)acryloyloxyisopropoxyphenyl)propane.

Examples of the aliphatic difunctional group-containing hydrophobic polymerizable monomer include ethylene glycol di(meth)acrylate, diethylene glycol di(meth)acrylate, triethylene glycol di(meth)acrylate, butylene glycol di(meth)acrylate, neopentyl glycol di(meth)acrylate, propylene glycol-di(meth)acrylate, 1,3-butanediol di(meth)acrylate, 1,4-butanediol di(meth)acrylate, 1,6-hexanediol di(meth) acrylate, and di-2-(meth)acryloyloxyethyl-2,2,4-trimethylhexamethylenedicarbamate.

Examples of the aliphatic trifunctional group-containing hydrophobic polymerizable monomer include trimethylolpropane tri(meth)acrylate, trimethylolethane tri(meth)acrylate, and trimethylolpropane tri(meth)acrylate.

Examples of the aliphatic tetrafunctional group-containing hydrophobic polymerizable monomer include pentaerythritol tetra(meth)acrylate and pentaerythritol tetraacrylate.

Specific examples of the urethane-based hydrophobic polymerizable monomer include di(meth)acrylates, which has a di- or tri-functional, or higher polyfunctional polymerizable group and also have an urethane bond, derived from adducts of polymerizable monomers having a hydroxyl group such as 2-hydroxyethyl (meth)acrylate, 2-hydroxypropyl (meth)acrylate and 3-chloro-2-hydroxypropyl (meth) acrylate, and diisocyanate compounds such as methylcyclohexane diisocyanate, methylenebis(4-cyclohexyl isocyanate), hexamethylene diisocyanate, trimethylhexamethylene diisocyanate, isophorone diisocyanate, diisocyanatemethylmethylbenzene and 4,4-diphenylmethane diisocyanate. As long as it has a (meth)acrylate group, not only a monomer having a short main chain, but also an oligomer, a prepolymer and a polymer, each having a long main chain, can be used without any limitation.

These hydrophobic monomers are not limited thereto and can also be used alone or in combination.

Among these hydrophobic monomers, those having solubility in 100 parts by weight of water at 23° C. of less than 5 parts by weight is preferred, and those having solubility in 100 parts by weight of water at 23° C. of less than 1 part by weight is more preferred. Specifically 2,2-bis(4-(3-methacryloyloxy-2-hydroxypropoxy)phenyl)propane (Bis-GMA), 2,2-bis(4-methacryloyloxyethoxyphenyl)propane (D-2.6E), di(methacryloyloxy)-2,2,4-trimethylhexamethylenediurethane (UDMA), triethylene glycol dimethacrylate (TEGDMA), neopentyl glycol dimethacrylate, and trimethylolpropane trimethacrylate are preferably used.

The content of the hydrophobic monomer compounded in a dental composition as a dental composite material composition is preferably 10 to 90 parts by weight, more preferably 40 to 80 parts by weight based on 100 parts by weight of the total weight of component (r): hydrophilic monomer and component (s): hydrophobic monomer contained in the dental composition as the dental composite material composition. When the content deviates from the above range, wettability to the surface of the adherend to be bonded deteriorates and polymerizability is deteriorated, and thus adhesive property deteriorate.

A proportion of these monomers in the dental composition as the dental composite material may be optionally selected depending upon a material property required for a composite material. A filling amount of low-viscous materials such as sealants, bonding materials, primers, tooth surface treating agents, opacifying agents and cements generally used in the dental field should be set at a relatively high level since higher fluidity required as material property is required for these materials. Accordingly, the content is preferably 20 parts by weight or more, more preferably within a range of 20.0 to 95.0 parts by weight, more preferably within a range of 30.0 to 70.0 parts by weight relative to the whole component of the dental composition as the dental composite material composition. In addition, a filling amount of high-viscous materials such as a composite resin and a veneer crown resin should be set at a relatively low level since, as the required material property, such the shapability is required that does not cause deformation after shape adjustment. Accordingly, the amount is preferably 2 parts by weight or more, more preferably within a range of 50.0 to 98.0 parts by weight, further preferably within a range of 75.0 to 98.0 parts by weight relative to the whole component of the dental composition as the dental composite material composition.

A known radical generator may be used as the component (d): polymerization initiator used in case that the dental composition of the present disclosure is the dental composite material composition. Polymerization initiators are generally classified into chemical polymerization initiators that initiates polymerization by mixing the same with the monomers upon use, thermal polymerization initiators that initiates polymerization by heating or warming the composition, and photopolymerization initiator that initiates polymerization by light irradiation.

Among polymerization initiators used in case that the dental composition of the present disclosure is the dental composite material composition, examples of chemical polymerization initiators may include redox type polymerization initiator systems comprising an organic peroxide/an amine compound or an organic peroxide/an amine compound/a sulfinic acid salt, or an organic peroxide/an amine compound/a borate compound, and organometal type initiator systems that initiate polymerization by reacting with oxygen or water.

Examples of the aforementioned organic peroxides may include benzoylperoxide, parachlorobenzoylperoxide, 2,4-dichlorobenzoyl peroxide, acetyl peroxide, lauroyl peroxide, tertiary-butyl peroxide, cumene hydroperoxide, 2,5-dimethylhexane, 2,5-dihydroperoxy, methyl ethyl ketone peroxide, and tertiary-butyl peroxide benzoate, but are not limited to. The organic peroxides can be used alone, or in a combination of a few of them.

Examples of the aforementioned amine compounds may include a secondary or tertiary amine in which an amine group is bound to an aryl group, and particular examples thereof are p-N,N'-dimethyltoluidine, N,N'-dimethylaniline, N'-β-hydroxyethylaniline, N,N'-di(β-hydroxyethyl)aniline, p-N,N'-di(β-hydroxyethyl)toruidine, N-methylaniline, and p-N-methyltoluidine, but are not limited to. The amine compounds may be used alone, or in combination of a few of them.

Examples of the aforementioned sulfuric acid salts may include sodium benzenesulfinate, lithium benzenesulfinate, and sodium p-toluenesulfinate, but are not limited to. The sulfuric acid salts may be used alone, or in combination of a few of them.

Examples of the aforementioned borate compound include a sodium salt, a lithium salt, a potassium salt, a magnesium salt, a tetrabutyl ammonium salt and a tetramethyl ammonium salt of trialkylphenylboron and trialkyl (p-fluorophenyl)boron (wherein the alkyl group is n-butyl group, n-octyl group, n-dodecyl group or the like), but are not limited to. The borate compounds may be used alone, or in a combination of few of them.

Examples of the aforementioned organometal type polymerizable initiators may include organic boron compounds such as triphenylborane, tributylborane, and a partial oxide of tributylborane, but are not limited to. The organometal type polymerizable initiators may be used alone, or in a combination of few of them.

Among polymerization initiators used in case that the dental composition of the present disclosure is the dental composite material composition, azo compounds such as azobisisobutyronitrile, methyl azobisisobutyrate and azobiscyano valeric acid may be used as a thermal polymerization initiator.

The photopolymerization initiator used in case that the dental composition of the present disclosure is the dental composite material composition may be a photosensitizer. The photosensitizer may be used alone or in combination with a photopolymerization promotor. Examples of the aforementioned photosensitizers may include α-diketones such as benzyl, camphorquinone, α-naphthyl, acetonaphtone, p,p'-dimethoxybenzyl, p,p'-dichlorobenzylacetyl, pentadione, 1,2-phenanthrenquinone, 1,4-phenanthrenquinone, 3,4-phenanthrenquinone, 9,10-phenanthrenquinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphineoxides such as 2,4,6-trimethylbenzoyl diphenylphosphineoxide and bis(2,6-dimethoxybenzoyl)-2,4,4-trimethylpentylphosphineoxide; α-aminoacetophenones such as 2-benzyl-dimethylamino-1-(4-morpholinophenyl)-butanone-1,2-benzyl-diethyl-amino-1-(4-morpholinophenyl)propanone-1; ketals such as benzyldimethylketal, benzyldiethylketal and benzyl(2-methoxyethylketal); titanocenes such as bis (cyclopentadienyl)-bis[2,6-difluoro-3-(1-pyrolyl)phenyl] titanium, bis(cyclopentadienyl)-bis(pentanefluorophenyl) titanium and bis(cyclopentadienyl)-bis(2,3,5,6-tetrafluoro-4-disiloxyphenyl)-titanium.

Examples of the aforementioned photopolymerization promotors may include tetriary amines such as N,N-dimethylaniline, N,N-diethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoic acid ethyl ester, p-demtethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 4-dimethylaminopyridine, N,N-dimethyl-α-naphthylamie, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino) diethanol; secondary amines such as N-phenylglycine; barbituric acids such as 5-butylbarbituric acid and 1-benzyl-5-phenylbarbituric acid; tin compounds such as dibutyltin diacetate, dibutyltin dilaurate, dioctyltin dilaurate, dioctyltin diperacetate, dioctyltin bis(mercaptoacetic acid isooctyl ester) salt and tetramethyl-1,3-diacetoxydistannoxane; aldehyde compounds such as laurylaldehyde and terephthalaldehyde; sulfur-containing compounds such as dodecylmercaptan, 2-mercaptobenzooxazole, 1-decanethiol and thiosalicylic acid.

The dental composition as the dental composite material composition may further contain an oxycarboxylic acid such as citric acid, maleic acid, tartaric acid, glycolic acid, gluconic acid, α-oxyisobutyric acid, 2-hydroxypropioic acid, 3-hydroxybutanoic acid, 4-hydroxybutanoic acid, and dimethylolpropioic acid to improve the photopolymerization promoting ability.

These polymerization initiators used in case that the dental composition of the present disclosure is the dental composite material composition may be used alone or as a mixture of two or more thereof. In addition, these polymerization initiators may be used in combination irrespective of the polymerization form and the kind of polymerization initiators. The content of a polymerization initiator to be added may be appropriately determined depending upon the use. In general, the content may be selected from a range of 0.1 to 10 parts by weight based on whole monomer.

The polymerization initiator in case that the dental composition of the present disclosure is the dental composite material composition is preferably a photopolymerization initiator. The dental composite material compositions containing a photopolymerization initiator is relatively easy to be polymerized without substantial air bubble entrainment. The photopolymerization initiator is preferably a combination of an α-diketone and a tertiary amine and more preferably a combination of camphorquinone with an aromatic amine having an amino group directly bound to the benzene ring such as ethyl p-N,N-dimethylaminobenzoate or with an aliphatic amine having a double bond in the molecule such as N,N-dimethylaminoethyl methacrylate. In the dental composition as the dental composite material composition, depending upon the use, coumarin-based, cyanine-based and thiazine-based sensitizing dyes; photo acid generators which are irradiated with light to generate Brønsted acid or Lewis acids, such as a halomethyl group substituted-s-triazine derivative, diphenyliodonium salt compound, etc.; quaternary ammonium halides; and transition metal compounds can be appropriately used.

The dental composition as the dental composite material composition may be colored with a coloring pigment in accordance with a product property. The coloring pigments are classified into inorganic pigments and organic pigments. Examples of inorganic pigments may include chromates such as chrome yellow, zinc yellow and barium yellow; ferrocyanides such as prussian blue; sulfides such as vermilion, cadmium yellow, zinc sulfide, antimony white and cadmium red; sulfates such as barium sulfate, zinc sulfate and strontium sulfate; oxides such as zinc white, titanium white, blood red, black iron oxide and chromium oxide; hydroxides such as aluminum hydroxide; silicates such as calcium silicate and ultramarine; and carbons such as carbon block and graphite. Examples of organic pigments may include nitoroso pigments such as Naphthol Green B and Naphthol Green Y; nitoro pigments such as Naphthol S and Lithol Fast Yellow 2G; insoluble azo pigments such as Permanent Red 4R, Brilliant Fast Scarlet, Hanza Yellow and Benzidine Yellow; poorly-soluble azo pigments such as Lithol Red, Lake Red C and Lake Red D; soluble azo pigments such as Brilliant Caramine 6B, Permanent Red F5R, Pigment, Scarlet 3B and Bordeaux 10; phthalocyanine pigments such as Phthalocyanine Blue, Phthalocyanine Green and Sky Blue; basic dye pigments such as Rhodamine Lake, Malachite Green Lake and Methyl Violet Lake; and acidic dye pigments such as Peacock Blue Lake, Eosin Lake and Quinoline Yellow Lake. These pigments may be used alone or in combination of two or more thereof. In a preferred embodiment of the present disclosure, the coloring pigment is preferably an inorganic pigment, preferably titanium white, blood red, black iron oxide or yellow iron oxide.

Preferably, the dental composition as the dental composite material composition may contain an ultraviolet absorber such as 2-hydroxy-4-methylbenzophenone, a polymerization inhibitor such as hydroquinone, hydroquinone monomethyl ether, 2,5-ditert-butyl-4-methylphenol or butylated hydroxytoluene (BHT), a discoloration inhibitor, an antibacterial agent, a coloring pigment, or other conventionally known additive. The dental composition as the dental composite material composition may be packed in a single package, or divided into two packs or the other type packages. The package of the dental composition as the dental composite material composition may be determined depending upon the kind of polymerization initiator or the use.

The dental composition as the dental composite material composition may be prepared by mixing the above described component (a), component (b), component (c) and component (d).

The dental composition as the dental composite material composition may prepare a composite material by a process that comprises, for example, at least a mixed monomer preparing step, a mixed monomer preserving step, a composite material preparing step, a composite material preserving step, a composite material filling step, and a small quantity preserving container preserving step.

As the component (h): radical polymerizable monomer used in case that the dental composition of the present disclosure is the dental resin cement (hereinafter, referred to as "resin cement"), all of radical polymerizable monomers that do not correspond to the component (i): acidic group-containing monomer and do not correspond to the component (a) may be used, and examples include (meth)acrylic acid ester derivatives, alkylene glycol di(meth)acrylates, alkyl di(meth)acrylates, epoxy di(meth)acrylates, bisphenol A-alkyl di(meth)acrylates, urethane di(meth)acrylates, urethane tri(meth)acrylates, urethane tetra(meth)acrylates, hydroxyalkyl(meth)acrylates, (meth)acrylates having a silicon group, (meth)acrylates having a —SH or —S—S— group, and styrene derivatives. Specifically, example includes methyl(meth)acrylate, ethyl(meth)acrylate, ethyleneglycol di(meth)acrylate, triethyleneglycol di(meth)acrylate, di-2-methacryloyloxyethyl-2,2,4-trimethylhexamethylene dicarbamate, 2,2'-bis[4-(3-(meth)acryloyloxy-2-hydroxypropoxy)phenyl]propane, di(meth)acryloxyisophorone dicarbamate, 2-hydroxyethyl(meth)acrylate, 6-hydroxyhexyl (meth)acrylate, 2-hydroxypropyl (meth)acrylate, glycerol di(meth)acrylate, and γ-methacryloxypropyltrimethoxysilane, etc. A particularly suitable radical polymerizable monomer includes ethyleneglycol di(meth)acrylate, triethyleneglycol di(meth)acrylate, hexamethyleneglycol di(meth)acrylate, 1,6-hexane di(meth)acrylate, di(meth)acryloxyethyl-2,2,4-trimethylhexamethylene diurethane, di(meth)acryloxyisophorone diurethane, 2,2'-bis[4-(3-(meth)-acryloyloxy-2-hydroxypropoxy)phenyl]propane, 2-hydroxyethyl(meth)acrylate, 2-hydroxypropyl(meth)acrylate, glycerol di(meth)acrylate, etc. Among them, ethyleneglycol di(meth)acrylate, triethyleneglycol di(meth)acrylate, di-2-methacryloyloxyethyl-2,2,4-trimethylhexamethylene dicarbamate, 2,2,-bis[4-(3-(meth)acryloyloxy-2-hydroxypropoxy)phenyl]propane and 2-hydroxyethyl(meth)acrylate are particularly suitable. These radical polymerizable monomers may be used alone or by mixing two or more of them.

The content of the component (h): radical polymerizable monomer in case that the dental composition of the present disclosure is the dental resin cement is usually 13.0 to 45.0 wt. %, preferably 15.0 to 40.0 wt. %, more preferably 20.0 to 35.0 wt. %, based on a whole amount other than the component (a). When the content is less than 13.0 wt. %, then a viscosity of the paste becomes too high, whereas when it is greater than 45.0 wt. %, then a viscosity of the paste becomes too low and, as the result, the paste property suitable for use as the resin cement cannot be obtained.

In case the dental composition is the dental resin cement, as the component (i): acidic group-containing monomer, any polymerizable monomer can be used without any limitation, as long as the monomer has an acidic group and does not correspond to the component (a). Specific examples of the acidic group of the component (i): acidic group-containing monomer are not limited to, but include a phosphoryl group, a pyrophosphoryl group, a phosphonyl group, a carboxylic acid group, a sulfonyl group, and a thiophosphonyl group. In addition, any acidic group-containing monomers may be used regardless of the number or the type of radical polymerizable unsaturated groups (monofunctional group or multifunctional groups) of the component (i): acidic group-containing monomer. Specific examples of the unsaturated group of the component (i): acidic group-containing monomer are not limited to, but include an acryloyl group, a methacryloyl group, a styryl group, a vinyl group, and an aryl group. It is preferable that an acidic group-containing polymerizable monomer has an acryloyl group and/or a methacryloyl group among these unsaturated groups.

These component (i): acidic group-containing monomer may contain together other functional group such as an alkyl group, halogen, an amino group, a glycidyl group, and a hydroxy group in a molecule. In addition, not only a monomer with a short main chain but also be an oligomer, a prepolymer, or the like with a long main chain may be used as the component (i): acidic group-containing monomer without any limitation. Further, derivatives of the component (i): acidic group-containing monomer such as a metallic salt, an ammonium salt, and an acid chloride obtained by partially neutralizing the acidic group of the component (i): acidic group-containing monomer may also be used to the extent that the adhesion to various adherends is not adversely affected.

Specific examples of component (i): acidic group-containing monomer that can be used in case that the dental composition of the present disclosure is the dental resin cement include the following. In the present specification, the term "(meth)acrylate" or "(meth)acryloyl" inclusively refers to both of an acryloyl and a methacryloyl.

Specific examples of an acidic group-containing monomer which has a phosphoryl group are not limited to, but include (meth)acryloyloxymethyl dihydrogen phosphate, 2-(meth)acryloyloxyethyl dihydrogen phosphate, 3-(meth) acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth) acryloyloxyundecyl dihydrogen phosphate, 12-(meth) acryloyloxydodecyl dihydrogen phosphate, 16-(meth) acryloyloxyhexadecyl dihydrogen phosphate, 20-(meth) acryloyloxyeicosyl dihydrogen phosphate, di(meth) acryloyloxyethyl hydrogensphosphate, dimeth acryloyloxybutyl hydrogen phosphate, di(meta) acryloyloxyhexyl hydrogen phosphate, di(meth) acryloyloxyoctyl hydrogen phosphate, di(meth) acryloyloxynonyl hydrogen phosphate, di(meth) acryloyloxydecyl hydrogen phosphate, 1,3-di (meth) acryloyloxypropyl-2-dihydrogenphosphate, 2-(meth) acryloyloxyethylphenyl hydrogen phosphate, 2-(meth) acryloyloxyethyl 2'-bromoethyl hydrogen phosphate and (meth) acryloyloxyethylphenyl phosphonate.

Specific examples of an acidic group-containing monomer which has a pyrophosphoryl group are not limited to, but include, bis [2-(meth) acryloyloxyethyl]pyrophosphate, bis [3-(meth) acryloyloxypropyl] pyrophosphate, bis [4-(meth) acryloyloxybutyl] pyrophosphate, bis [5-(meth) acryloyloxypentyl] pyrophosphate, bis [6-(meth) acryloyloxyhexyl] pyrophosphate, bis [7-(meth) acryloyloxyheptyl] pyrophosphate, bis [8-(meth) acryloyloxyoctyl] pyrophosphate, bis [9-(meth) acryloyloxynonyl] pyrophosphate, bis [10-(meth) acryloyloxydecyl] pyrophosphate, bis [12-(meth) acryloyloxydodecyl] pyrophosphate, tetra [2-(meth) acryloyloxyethyl]pyrophosphate, and tris [2-(meth) acryloyloxyethyl]pyrophosphate.

Specific examples of an acidic group-containing monomer which has a carboxyl group are not limited to, but include (meth) acrylic acid, 2-chloro (meth) acrylic acid, 3-chloro(meth)acrylic acid, 2-cyano (meth) acrylic acid, aconitic acid, mesaconic acid, maleic acid, maleic anhydride, itaconic acid, itaconic anhydride, fumaric acid, glutaconic acid, citraconic acid, utraconic acid, 1,4-di(meth) acryloyloxyethylpyromellitic acid, 6-(meth) acryloyloxynaphthalene-1,2,6-tricarboxylic acid, 1-buten-1,2,4-tricarboxylic acid, 3-buten-1,2,3-tricarboxylic acid, N-(meth) acryloyl-p-aminobenzoic acid, N-(meth) acryloyl-5-aminosalicylic acid, 4-(meth) acryloyloxyethyltrimellitic acid and anhydride thereof, 4-(meth) acryloyloxybutyltrimellitic acid and anhydride thereof, 2-(meth) acryloyloxybenzoic acid, β-(meth) acryloyloxyethyl hydrogen succinate, β-(meth) acryloyloxyethyl hydrogen maleate, 11-(meth) acryloyloxy-1,1-undecanedicarboxylic acid, p-vinylbenzoic acid, 4-(meth) acryloyloxyethoxycarbonylphthalic acid, 4-(meth) acryloyloxybutyloxycarbonylphthalic acid, 4-(meth) acryloyloxyhexyloxycarbonylphthalic acid, 4-(meth) acryloyloxyoctyloxycarbonylphthalic acid, 4-(meth) acryloyloxydecyloxycarbonylphthalic acid and anhydride thereof, 5-(meth) acryloylaminopentylcarboxylic acid, 6-(meth) acryloyloxy-1,1-hexanedicarboxylic acid, 7-(meth) acryloyloxy-1,1-heptanedicarboxylic acid, 8-(meth) acryloyloxy-1,1-octanedicarboxylic acid, 10-(meth) acryloyloxy-1,1-decanedicarboxylic acid, and 11-(meth) acryloyloxy-1,1-undecanedicarboxylic acid.

Specific examples of an acidic group-containing monomer has a phosphonyl group are not limited to, but include 5-(meth) acryloyloxypentyl-3-phosphonopropionate, 6-(meth) acryloyloxyhexyl-3-phosphonopropionate, 10-(meth) acryloyloxydecyl-3-phosphonopropionate, 6-(meth) acryloyloxyhexyl-3-phosphonoacetate, and 10-(meth) acryloyloxydecyl-3-phosphonoacetate.

Specific examples of an acidic group-containing monomer which has a sulfonate group are not limited to, but include 2-(meth) acrylamido-2-methylpropanesulfonic acid, styrenesulfonic acid, 2-sulfoethyl (meth) acrylate, 4-(meth) acryloyloxy benzenesulfonic acid, and 3-(meth) acryloyloxy propanesulfonic acid.

These acid group-containing monomers can be used alone, or in a combination thereof.

As the component (i): acidic group-containing monomer which can used in case that the dental composition of the present disclosure is the dental resin cement, it is preferable to use a polymerizable monomer having a phosphonic acid group and/or a phosphoric acid ester group. Examples of a polymerizable monomer having a phosphonic acid group and/or a phosphoric acid ester group include a polymerizable monomer represented by the general formula [I]:

[Chemical formula 5]

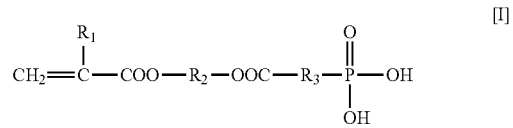

(wherein $R_1$ is a hydrogen atom or a methyl group, $R_2$ is an alkylene group having the carbon atom number of 5 to 10, and $R_3$ is an alkylene group having the carbon atom number of 1 to 6).

As specific compounds represented by the above general formula [I], for example, following compounds are exemplified.

[Chemical formula 6]

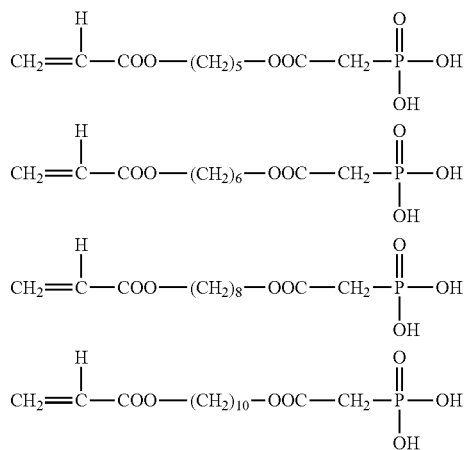

[Chemical formula 7]

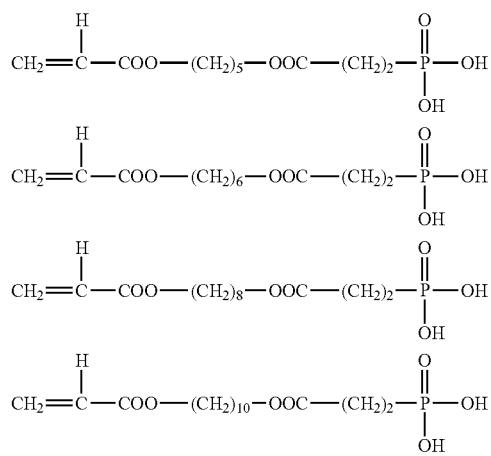

[Chemical formula 8]

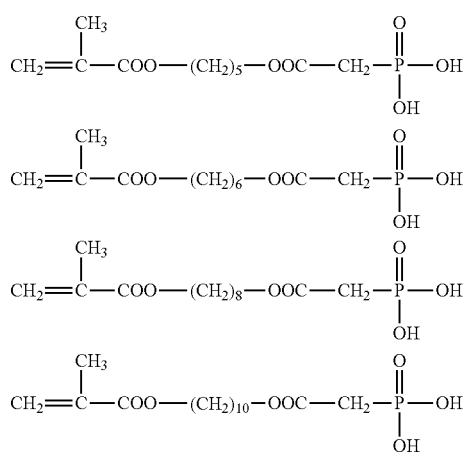

[Chemical formula 9]

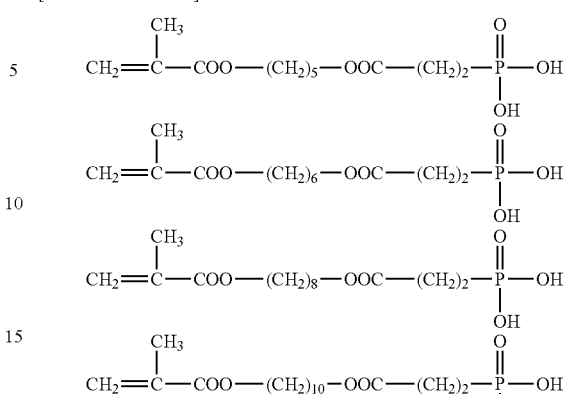

Moreover, as the component (i): acidic group-containing monomer used in case that the dental composition of the present disclosure is the dental resin cement, in addition to the compound [I], a polymerizable monomer having a phosphoric acid ester group such as 2-(methacryloxy)ethyl phosphate, bis[2-(methacryloxy)ethyl] phosphate and the like is also effective.

As the component (i): acidic group-containing monomer which can used in case that the dental composition of the present disclosure is the dental resin cement, it is particularly preferable to use a polymerizable monomer having a dibasic acid carboxyl group. Examples of a polymerizable monomer having a dibasic acid carboxyl group include 1,4-di(meth)acryloxyethylpyromellitic acid, 4-(meth)acryloxybutyltrimellitic acid, 4-(meth)acryloxyhexyltrimellitic acid, 4-(meth)acryloxydecyltrimellitic acid, 4-acryloxybutyltrimellitic acid, and 11-(meth)acryloxy-1,1-undecanedicarboxylic acid, etc., and 4-(meth)acryloxyethyltrimellitic acid and 4-(meth)acryloxyethyltrimellitic acid anhydride are particularly preferable.

These acid group-containing polymerizable monomers can be used alone, or in a combination thereof.

In case that the dental composition of the present disclosure is the dental resin cement, it is preferable to contain a polymerizable monomer having a phosphonic acid group and/or a phosphoric acid ester group and a polymerizable monomer having a dibasic acid carboxyl group, as the component (i): acidic group-containing monomer.

In case that the dental composition of the present disclosure is the dental resin cement, the content of the component (i): acidic group-containing monomer is usually 0.1 to 20% wt. %, preferably 0.4 to 12 wt. %, and more preferably 0.6 to 7 wt. % based on a total amount other than the component (a). When the content is less than 0.1 wt. %, adhesive property to all of adherends may be lowered, whereas when it is greater than 20.0 wt. %, then adhesive property to dentin may be lowered and/or a solubility of the polymerizable monomer may be lowered.

The component (g): silane coupling agent used in case that the dental composition of the present disclosure is the dental resin cement is not particularly limited, but specifically, the same one as the case that the dental composition is the dental composite material composition is preferably used, and particularly preferably, methyltrichlorosilane, dimethyldichlorosilane, γ-methacryloyloxypropyltrimethoxysilane, and hexamethyldisilazane are used. In case that the dental composition of the present disclosure is the dental resin cement, the content of the component (g): silane coupling agent is 0.1 to 15 wt. %, preferably 1 to 8 wt. % based on a total amount other than the component (a).

The component (b): filler used in case that the dental composition of the present disclosure is the resin cement is not particularly limited, and a filler known in the art such as an inorganic filler and/or an organic filler and/or an organic-inorganic composite filler, for example, may be used without any limitation. Other constitution of component (b): filler can be the same constitution as the case that the dental composition is the dental composite material composition, except for the constitution described below. In this case, the shape and the circularity of the filler, and the inorganic filler can be the same as those in case that the dental composition is the dental composite material composition.

In case that the dental composition is the dental resin cement, component (b): filler having an average particle diameter of 0.1 to 10 μm can be used. It is preferably 0.1 to 5 μm.

In this case, the organic filler and the organic-inorganic composite filler can have the same constitution as that in case that the dental composition is the dental composite material composition.

After the surfaces of the particles of the filler, such as the inorganic, organic, or organic-inorganic composite filler, are treated by a method known in the art, the filler can be used for the dental composition as the dental resin cement.

The surface treatment agent and the surface treatment method that can be used for the surface treatment can be the same as in case that the dental composition is the dental composite material composition.

The filler surface is subjected to a surface treatment by a special surface treatment agent and/or a special surface treatment method for the purpose of multi-functionalizing the filler, without any limitation.

In order to improve affinity of the filler for the resin components such as the polymerizable monomer, it is desirable to treat the filler with silane by the conventional method. The silane coupling agent (g) to be used can be the same as the case that the dental composition is the dental composite material composition.

In case that the dental composition of the present disclosure is the dental resin cement, the content of the component (b): filler is usually 54.725 to 80.0 wt. %, preferably 57.0 to 77.0 wt. % based on a total amount other than the component (a). When it is less than 54.725 wt. %, filler settlement or so-called a floating liquid phenomenon may be caused, whereas when it is greater than 80.0 wt. %, fluidity of the paste may be significantly reduced to deteriorate cement functions.

The component (f): polymerization catalyst used in case that that the dental composition of the present disclosure is the dental resin cement consists of component (x): polymerization accelerator and component (d): polymerization initiator and the polymerization initiator includes a chemical polymerization initiator and a photopolymerizationinitiator.

Among them, the component (x): polymerization accelerator may include, for example, an alkali or alkaline earth metal salt of barbituric acid and an aromatic secondary or tertiary amine and the like.

Examples of the alkali or alkaline earth metal salt of barbituric acid include a sodium salt of 5-n-butylbarbituric acid, a calcium salt of 5-n-butylbarbituric acid, a sodium salt of 1-benzyl-5-phenylbarbituric acid, a calcium salt of 1-benzyl-5-phenylbarbituric acid, a sodium salt of 1,3,5-trimethylbarbituric acid, a calcium salt of 1,3,5-trimethylbarbituric acid and the like.

In case that the dental composition of the present disclosure is the dental resin cement, an amount of the alkali or alkaline earth metal salt of barbituric acid as the component (x): polymerization accelerator is usually 0.025 to 3.0 wt. %, preferably 0.1 to 2.0 wt. %, more preferably 0.7 to 1.5 wt. % based on a total amount other than the component (a). When it is less than 0.025 wt. %, then the curing may become insufficient, whereas when it is greater than 3.0 wt. %, then a suitable manipulating time may not be obtained since the curing rapidly proceeds.

Examples of the aromatic secondary or tertiary amine as the component (x): polymerization accelerator in case that the dental composition of the present disclosure is the dental resin cement include N-dimethylaniline, N-dimethyl-p-toluidine, N,N-di (2-hydroxyethyl)-p-toluidine, and N-methyl-p-toluidine and the like.

In case that the dental composition of the present disclosure is the dental resin cement, the content of the aromatic secondary or tertiary amine as the component (x): polymerization accelerator is usually 0.025 to 1.0 wt. %, preferably 0.1 to 0.8 wt. %, and more preferably 0.1 to 0.5 wt. % based on a total amount other than the component (a). When it is less than 0.025 wt. %, there is a case the curing becomes insufficient, whereas when it is greater than 1.0 wt. %, there is a case a suitable manipulating time cannot be obtained since the curing rapidly proceeds.

Examples of the chemical polymerization initiator of the component (d): polymerization initiator in case that the dental composition of the present disclosure is the dental resin cement include an organic peroxide such as benzoyl peroxide, 4,4'-dichlorobenzoyl peroxide, 2,4-dichlorobenzoyl peroxide, dilauryl peroxide, methyl ethyl ketone peroxide, t-butylperoxymaleic acid, peroxysuccinic acid, but t-butylperoxymaleic acid, peroxysuccinic acid and 4,4'-dichlorobenzoyl peroxide are particularly preferable.

Examples of the photopolymerization initiator of the component (d): polymerization initiator in case that the dental composition of the present disclosure is the dental resin cement include an ultraviolet light sensitizer, a visible light sensitizer and the like such as benzoin methyl ether, benzoin ethyl ether, benzoin isopropyl ether, benzoin, benzophenone, thioxanthon, 2-chlorthioxanthon, 2-hydroxy-3-(3,4-dimethyl-9H-thioxanthen-2-yloxy-N,N,N-trimethyl-1-propane aluminum chloride, 9,10-anthraquinone, camphorquinone, benzyl, 4,4'-dicyclobenzyl, diacetyl, bis (acyl)phosphine oxides, and mono(acyl)phosphine oxides.

In case that the dental composition of the present disclosure is the dental resin cement, the content of the component (d): polymerization initiator is usually 0.05 to 2.0 wt. %, and preferably 0.1 to 1.5 wt. %, more preferably 0.1 to 1.0 wt. % based on a total amount other than the component (a). When it is less than 0.05 wt. %, then the curing becomes insufficient, whereas when it is greater than 2.0 wt. %, then a suitable manipulating time cannot be obtained since the curing rapidly proceeds.

The dental composition as the dental resin cement is used by mixing the first paste and the second paste, and is cured preferably for 100 to 600 seconds after mixing two pastes. When the curing time is less than 100 seconds, then a time necessary for manipulating cannot be obtained, whereas when it is greater than 600 seconds, then it greatly gives a burden to a patient.

The dental composition as the dental resin cement may contain hydroquinone, hydroquinone monomethyl ether, hydroxymethoxybenzophenone, butylated hydroxytoluene and the like, as a shelf life stabilizer.

In case that the dental composition as the dental resin cement contains a shelf life stabilizer, the content of the shelf life stabilizer is usually 0.02 to 0.2 wt. %, and preferably 0.03 to 0.06 wt. % based on a total amount other than the component (a). When it is less than 0.02 wt. %, a shelf life of the paste may become insufficient, whereas when it is greater than 0.2 wt. %, sufficient curing of the resin cement may not be obtained.

The dental composition as the dental resin cement may be a two paste-type and consists of a first paste and a second paste. The effect of the resin cement can be exhibited by mixing both of them upon use. A mixing ratio of the first paste and the second paste is, in terms of a weight ratio, usually 1:7 to 7:1, preferably 1:4 to 4:1, more preferably 1:2 to 2:1, and most preferably 1:1.

In case that the component (f): polymerization catalyst consists of the component (x): polymerization accelerator and the component (d): polymerization initiator in the dental composition as the dental resin cement, since the setting is initiated by mixing such the component (x): polymerization accelerator and the component (d): polymerization initiator, they have to be a separated two paste form until it is used.

Accordingly, when the above component is contained either or both of the first or/and second pastes, the above amount of components which corresponds to the mixing ratio of the first and second pastes, may be contained in the paste.

Therefore, in one embodiment, the present disclosure provides a dental composition as a dental resin cement, wherein the first paste contains component (b): filler, component (g): silane coupling agent and (x): polymerization accelerator, the second paste contains component (i): acidic group-containing monomer, component (b): filler and component (d): polymerization initiator, component (h): radical polymerizable monomer and component (a): monomer containing (meth)acrylamide group represented by formula (1) are contained in both or one of the first paste and the second paste.

The component (c): monomer other than the component (a) used in case that the dental composition of the present disclosure is the denture restorative material is not particularly limited as long as it is a monomer having a polymerizable group. Specifically, known monofunctional and/or polyfunctional monomers generally used for dental materials can be used. The monomer is preferably a (meth)acrylic acid group-containing monomer having an acryloyl group and/or a methacryloyl group.

Such a monomer can have the same constitution as the case that the dental composition is the dental composite material composition, except for the constitution described below. In this case, monofunctional monomer (non-crosslinkable monomer), aromatic bifunctional monomer (crosslinkable monomer), aliphatic bifunctional monomer (crosslinkable monomer), trifunctional monomer (crosslinkable monomer), tetrafunctional monomer (crosslinkable monomer) and the urethane-based monomer may have the same constitution as the case that the dental composition is the dental composite material composition.

The (meth)acrylic acid group-containing monomer used in the case that the dental composition is the denture restorative material may be a single component or may be a kneaded product of a plurality of (meth)acrylic acid group-containing monomers. A preferable (meth)acrylic acid group-containing monomer can include a crosslinkable monomer. A more preferable (meth)acrylic acid group-containing polymerizable monomer includes methyl (meth)acrylate (MMA) and both or any one of 1,6-hexanediol di(meth)acrylate (HDDMA) and triethylene glycol dimethacrylate (TEGDMA).

A monomer other than the above described the (meth)acrylate-based monomer, for example, a monomer, an oligomer or a polymer having at least one polymerizable group in the molecule may be used for the component (c): monomer other than the component (a), in accordance with purpose. The monomer other than the (meth)acrylate-based monomers may have a substituent such as an acidic group and a fluoro group in one molecule. In case that the dental composition is the denture restorative, the component (c): monomer other than the component (a) may be a single component, or may be a mixture of a plurality of monomers. When the viscosity of the monomer is extremely high at room temperature or the monomer is a solid, the monomer is preferably combined with a monomer low in viscosity and used as a polymerizable monomer mixture. In such a combination, the monomer may be used in combinations of two, or three or more.

The component (c): monomer other than the component (a) may include only monofunctional monomers, and may additionally include polyfunctional monomers. A preferable monomer includes an aromatic compound of a bifunctional monomer and an aliphatic compound of a bifunctional polymerizable monomer. A more preferable monomer includes 2,2-bis(4-(3-methacryloyloxy-2-hydroxypropoxy)phenyl)propane (Bis-GMA) and triethylene glycol dimethacrylate (TEGDMA).

The component (c): monomer other than the component (a) may include a monomer containing an acid group such as a phosphoric acid group, a carboxylic acid group, a phosphonic acid, a sulfonic acid group or the like in the molecule as a part of the monomer. The component (c): monomer other than the component (a) may include a component (u): sulfur atom-containing monomer containing a sulfur atom in the molecule.

It is preferable that the content of the monomer containing an acid group such as a phosphoric acid group, a carboxylic acid group, a phosphonic acid, a sulfonic acid group or the like in the molecule or the component (u): sulfur atom-containing monomer containing a sulfur atom in the molecule is preferably 0.5 to 20 wt. % based on 100 wt. % of the component (c): monomer other than the component (a).

Such a monomer can have the same constitution as the case that the dental composition is the dental composite material composition.

In addition, it is preferable that the component (c): monomer other than the component (a) contains a (meth)acrylic acid group-containing monomer and/or component (r): hydrophilic monomer. The hydrophilic monomer has at least one hydroxyl group and at least one polymerizable unsaturated group in one molecule, is not particularly limited, and can be appropriately selected from known compounds depending on the intended use. The term "hydrophilic monomer" means a solubility in water of 50 [g/100 g-$H_2O$] or more at 20° C., and it is preferable that the hydrophilic monomer is preferably compatible with water in any proportion at 20° C.

The hydrophilic monomer can be compounded to result in an enhancement in wettability to a denture base that is mounted in an oral cavity and absorbs water, in the case of repair of the denture base.

Specific examples of the hydrophilic monomer include 2-hydroxyethyl (meth)acrylate, 3-hydroxypropyl (meth)acrylate, 2-hydroxypropyl (meth)acrylate, 4-hydroxybutyl (meth)acrylate, N-2-hydroxyethyl (meth)acrylamide, N,N-bis(2-hydroxyethyl) (meth)acrylamide, 2,3-dihydroxypropyl (meth)acrylate, 2,3-dihydroxybutyl (meth)acrylate, 2,4-dihydroxybutyl (meth)acrylate, 2-hydroxymethyl-3-hydroxypropyl(meth)acrylate, 2,3,4-trihydroxybutyl(meth)acrylate, 2,2-bis(hydroxymethyl)-3-hydroxypropyl (meth)acrylate, 2,3,4,5-tetrahydroxypentyl (meth)acrylate, diethylene glycol mono(meth)acrylate, triethylene glycol mono(meth)acrylate, tetraethylene glycol mono(meth)acrylate, pentaethylene glycol mono(meth)acrylate and N-methylol(meth)acrylamide. Among them, 2-hydroxyethyl (meth)acrylate is most preferable.

The hydrophilic monomer can be compounded singly or can be used as a kneaded product of a plurality thereof.

The component (j): (meth) acrylic acid (co) polymer used in case that the dental composition of the present disclosure is the denture restorative material is a polymer or copolymer using the (meth)acrylic acid-containing monomer described in the section of the component (c): monomer other than the component (a) above. Among them, a polymer or copolymer of methyl (meth)acrylate and/or ethyl (meth)acrylate is preferable, and a copolymer of methyl methacrylate and ethyl methacrylate is particularly preferable. The acrylic acid (co)polymer can be used singly or in combinations of a plurality thereof, without any problem. The content of the (meth) acrylic acid (co) polymer is preferably 150 to 200 parts by weight based on 100 parts by weight of whole monomer. Further, the range is 0.5 to 5 parts by weight, further preferably 1 to 3 parts by weight.

The average molecular weight is 500 or more. The average molecular weight is preferably 10,000 to 1,000,000, particularly preferably 100,000 to 500,000. The particle size is preferably 20 to 200 μm. The particle size and the shape are not particularly limited, and a powder shape is preferable.

The component (f): polymerization catalyst used in the case that the dental composition is the denture restorative material contains at least one of a combination of a barbituric acid derivative and a halogen ion-forming compound and a combination of an organic peroxide and an amine compound.

Specific examples of the barbituric acids include barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethyl-barbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-1-ethylbarbituric acid, 1-benzyl-5-phenylbarbituric acid, 5-methyl barbituric acid, 5-propyl barbituric acid, 1,5-diethyl barbituric acid, 1-ethyl-5-methyl barbituric acid, 1-ethyl-5-isobutyl barbituric acid, 1,3-diethyl-5-butyl barbituric acid, 1-cyclohexyl-5-methyl barbituric acid, 1-cyclohexyl-5-ethyl barbituric acid, 1-cyclohexyl-5-propyl barbituric acid, 1-cyclohexyl-5-octyl barbituric acid, 1-cyclohexyl-5-hexyl barbituric acid, 5-butyl-1-cyclohexyl barbituric acid, 1-benzyl-5-phenyl barbituric acid and thiobarbituric acids, and salts thereof (alkali metal or alkali earth metals are particularly preferred). Examples of the salts thereof include sodium 5-butylbarbiturate, sodium 1,3,5-trimethylbarbiturate, and sodium 1-cyclohexyl-5-ethylbarbiturate.

Specific examples of particularly suitable barbituric acid derivative include, for example, 5-butyl barbituric acid, 1,3,5-trimethyl barbituric acid, 1-cyclohexyl-5-ethyl barbituric acid, 1-cyclohexyl-5-propyl barbituric acid, 1-benzyl-5-phenyl barbituric acid and sodium salts of these barbituric acids.

The content of barbituric acid derivative to be compounded is preferably 0.1 to 10 parts by weight based on 100 parts by weight of whole monomer. Further, it is preferably compounded in an amount of 0.5 to 5 parts by weight, further preferably 1 to 3 parts by weight. If the content to be compounded is less than 0.1 parts by weight, a case may occur in which reactivity is poor and curability cannot be achieved. If the content to be compounded is more than 10 parts by weight, the content of heat generation in a polymerization reaction may be remarkably large regardless of a certain curing time.

Specific examples of the halogen ion-forming compound include dilauryl dimethylammonium chloride, lauryldimethyl benzylammonium chloride, benzyl trimethylammonium chloride, diisobutylamine hydrochloride, tetra-n-butylammonium chloride, triethylamine hydrochloride, trimethylamine hydrochloride, dimethylamine hydrochloride, diethylamine hydrochloride, methylamine hydrochloride, ethylamine hydrochloride, isobutylamine hydrochloride, triethanolamine hydrochloride, β-phenylethylamine hydrochloride, acetylcholine chloride, 2-chlorotrimethylamine hydrochloride, (2-chloroethyl) triethylammonium chloride, tetra-decyldimethyl benzylammonium chloride, tetraethyl ammonium chloride, tetramethyl ammonium chloride, trioctylmethyl ammonium chloride, benzyldimethylcetyl ammonium chloride, benzyldimethyl stearylammonium chloride, dilauryldimethylammonium bromide, tetrabutylammonium bromide and benzyltriethylammonium bromide, and these may be used alone or in admixture of two or more.

The content of the halogen ion-forming compound is preferably 0.1 to 10 parts by weight based on 100 parts by weight of whole monomer. The content to be compounded is further preferably 0.5 to 5 parts by weight, still further preferably 1 to 3 parts by weight. If the content to be compounded is less than 0.1 parts by weight, reactivity is poor and a denture restorative material excellent in curing characteristics cannot be obtained. If the content to be compounded is more than 10 parts by weight, the amount of heat generation in a polymerization reaction may be remarkably large regardless of a certain curing time.

A preferred combination of the barbituric acid derivative and the halogen ion-forming compound is, for example, a combination of 1-cyclohexyl-5-propylbarbituric acid and trioctylmethylammonium chloride.

In this case, the organic peroxide can have the same constitution as the case that the dental composition is the dental composite material composition.

In this case, the amine compound can be the same as that in the case that the dental composition is the dental composite material composition.

In this case, the sulfuric acid salts can be the same as that in the case that the dental composition is the dental composite material composition.

The content of the component (f): polymerization catalyst in case of the combination of the barbituric acid derivative and the halogen ion-forming compound is preferably 0.01 to 10 parts by weight, more preferably 0.1 to 5 parts by weight based on 100 parts by weight of whole monomer.

The component (f): polymerization catalyst used in the case that the dental composition is the denture restorative material may contain an organometal compound. Specific examples of the organometal compound include copper(II)

acetylacetonate, acetylacetone copper, copper 4-cyclohexylbutyrate, cupric acetate, copper oleate, copper gluconate, acetylacetone manganese, manganese naphthenate, manganese octylate, acetylacetone cobalt(III), cobalt naphthenate, acetylacetone lithium, lithium acetate, acetylacetone zinc, zinc naphthenate, acetylacetone nickel, nickel acetate, acetylacetone aluminum, acetylacetone calcium, acetylacetone chromium(III), acetylacetone iron(III), sodium naphthenate and rare earth octoate, and these may be used singly. Specific examples includes a uniformly kneaded of two or more. Particularly preferred are copper (II) acetylacenate, acetylacetone copper and copper 4-cyclohexylbutyrate.

The content of such an organometal compound to be compounded is 0.001 to 1 part by weight, preferably 0.001 to 0.2 parts by weight based on 100 parts by weight of whole monomer. When the content to be compounded is less than 0.001 parts by weight, a case may occur in which reactivity is poor and curability cannot be achieved. When the content to be compounded is more than 1 part by weight, discoloration unique to the organometal compound is remarkable, and if the content to be compounded is more than 1 parts by weight, a case may occur in which such discoloration is observed. For example, when the organometal compound is acetylacetone copper, a blue color is displayed, and when the organometal compound is acetylacetone iron(III), a red-brown color is displayed.

For example, the dental composition as the denture restorative material may be a powder-liquid type denture restorative material in which a powder material and a liquid material is kneaded to use. In this case, the liquid material may contain component (a): monomer containing (meth) acrylamide group represented by formula (1), component (c): monomer other than the component (a) and trioctylmethylammonium chloride, and the powder material may contain component (j): (meth) acrylic acid (co) polymer and 1-cyclohexyl-5-propylbarbituric acid.

The dental composition as the denture restorative material may contain component (p): organic solvent. As the component (p): organic solvent, a known organic solvent can be used, and can be compounded to thereby serve to reduce the viscosity of the kneaded product of the dental composition as the denture restorative material, resulting in an enhancement in wettability to a denture base that is mounted in an oral cavity and absorbs water, in the case of repair of the denture base. As a specific component (p): organic solvent, methanol, ethanol, isopropanol, butanol, acetone, ethyl acetate, isopropyl ether or the like can be utilized. Methanol, ethanol or acetone is preferable, and ethanol is most preferable. The component (p): organic solvent can be included to thereby facilitate kneading with the powder material, exerting the effect of enhancing wettability to a wet base resin and wettability to a tooth substance. An excellent storage stability is also achieved.

The content of the component (p): organic solvent to be compounded can be 0.5 to 20 parts by weight based on 100 parts by weight of whole monomer. The amount is preferably 1 to 5 parts by weight. If the content of the component (p): organic solvent to be compounded is less than 0.5 parts by weight, the effect of reducing the viscosity of the liquid material and the effect of enhancing wettability are not largely exerted. On the other hand, if the content of the component (p): organic solvent to be compounded is more than 20 parts by weight, deterioration in physical properties is caused.

The dental composition as the denture restorative material may further contain component (b): filler. In the case of the powder-liquid type denture restorative material, the component (b): filler is contained in the powder material.

The component (b): filler is not particularly limited, and a known filler can be used. By compounding the filler, wear resistance and bending property ca be enhanced. Other constitution of component (b): filler can be the same constitution as the case that the dental composition is the dental composite material composition, except for the constitution described below. In this case, the shape and the circularity of the filler, and the inorganic filler can have the same constitution as the case that the dental composition is the dental composite material composition.

In this case, the ultrafine particulate inorganic filler, organic filler and the organic-inorganic composite filler can have the same constitution as that in case that the dental composition is the dental composite material composition.

The filler such as the inorganic, organic and organic-inorganic composite fillers can be used with the particle surface thereof being subjected to a surface treatment by a known method.

The surface treatment agent and the surface treatment method that can be used for the surface treatment can be the same as the case that the dental composition is the dental composite material composition.

The filler surface may be subjected to a surface treatment by a special surface treatment agent and/or a special surface treatment method for the purpose of multi-functionalizing the filler, without any limitation.

The content of the filler is preferably 0.1 to 100 parts by weight based on 100 parts by weight of whole monomer. Further preferably, the content is 1 to 10 parts by weight.

The component (k): acid group-containing monomer used in case that the dental composition of the present disclosure is the tooth substance adhesive primer is roughly divided into the component (n) inorganic acid group-containing monomer and the component (o) organic acid group-containing monomer.

As the component (n) inorganic acid group-containing monomer, any monomer can be used without any limitation, as long as the monomer does not correspond to the component (a) and has an inorganic acid group. Specifically known inorganic acid group-containing monomer(s) commonly used for a dental material can be used. Specific examples of the inorganic acid group of the inorganic acid group-containing monomer are not limited to, but include a phosphoryl group, a pyrophosphoryl group, a phosphonyl group, and a thiophosphoryl group.

In case that the dental composition of the present disclosure is the tooth substance adhesive primer, it is preferable that the component (n) inorganic acid group-containing monomer contains phosphorus and/or sulfur.

Specific examples of the unsaturated group of the inorganic acid group-containing monomer are not limited to, but include a (meth) acryloyl group, a styryl group, a vinyl group, and an aryl group. It is preferable that an inorganic acid group-containing monomer has a (meth) acryloyl group among these unsaturated groups.

Further, these inorganic acid group-containing monomers may contain together other functional group such as an alkyl group, halogen, an amino group, a glycidyl group, and a hydroxy group in a molecule.

The polymer of an inorganic acid group-containing monomer in which a portion or the entirety of the acidic group forms a salt with an alkaline metal can be used and specific examples of an inorganic acid group-containing monomer having a (meth) acryloyl group as an unsaturated group are listed below.

Specific examples of an inorganic acidic group-containing monomer which has a phosphoryl group are not limited to, but include (meth)acryloyloxymethyl dihydrogen phosphate, 2-(meth)acryloyloxyethyl dihydrogen phosphate, 3-(meth)acryloyloxypropyl dihydrogen phosphate, 4-(meth) acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, di(meth) acryloyloxyethyl hydrogensphosphate, dimeth acryloyloxybutyl hydrogen phosphate, di(meta) acryloyloxyhexyl hydrogen phosphate, di(meth) acryloyloxyoctyl hydrogen phosphate, di(meth) acryloyloxynonyl hydrogen phosphate, di(meth) acryloyloxydecyl hydrogen phosphate, 1,3-di(meth) acryloyloxypropyl-2-dihydrogenphosphate, 2-(meth) acryloyloxyethylphenyl hydrogen phosphate, 2-(meth) acryloyloxyethyl 2'-bromoethyl hydrogen phosphate and (meth) acryloyloxyethylphenyl phosphonate.

Specific examples of an inorganic acidic group-containing monomer which has a pyrophosphoryl group are not limited to, but include, bis [2-(meth) acryloyloxyethyl] pyrophosphate, bis [3-(meth) acryloyloxypropyl] pyrophosphate, bis [4-(meth) acryloyloxybutyl] pyrophosphate, bis [5-(meth) acryloyloxypentyl] pyrophosphate, bis [6-(meth) acryloyloxyhexyl] pyrophosphate, bis [7-(meth) acryloyloxyheptyl]pyrophosphate, bis [8-(meth) acryloyloxyoctyl] pyrophosphate, bis [9-(meth) acryloyloxynonyl] pyrophosphate, bis [10-(meth) acryloyloxydecyl] pyrophosphate, bis [12-(meth) acryloyloxydodecyl] pyrophosphate, and tris [2-(meth) acryloyloxyethyl]pyrophosphate.

Specific examples of an inorganic acidic group-containing monomer which has a thiophosphoryl group are not limited to, but include, 2-(meth) acryloyloxyethyl dihydrogendithiophosphate, 3-(meth) acryloyloxypropyl dihydrogendithiophosphate, 4-(meth) acryloyloxybutyl dihydrogendithiophosphate, 5-(meth) acryloyloxypentyl dihydrogendithiophosphate, 6-(meth) acryloyloxyhexyl dihydrogendithiophosphate, 7-(meth) acryloyloxyheptyl dihydrogendithiophosphate, 8-(meth) acryloyloxyoctyl dihydrogendithiophosphate, 9-(meth) acryloyloxynonyl dihydrogendithiophosphate, 10-(meth) acryloyloxydecyl dihydrogendithiophosphate.

In case that the dental composition is the tooth substance adhesive primer, it is particularly preferable that the component (n) inorganic acid group-containing monomer is an inorganic acid group-containing monomer having a phosphonic acid group. The inorganic acid group-containing monomer having a phosphonic acid group (phosphonic acid group-containing monomer) means a monomer having at least one (—PO(OH)$_2$) bonded directly to a carbon atom, or a phosphonic acid monoester group (—PO(OH)(OR)) and at least one polymerizable unsaturated group in the molecule.

It is possible to use those having any functional group in the molecule without any limitation as long as these conditions are satisfied. In the phosphonic acid group-containing monomer, the number of phosphonic acid groups or phosphonic acid monoester groups, and the kind and number of radical polymerizable unsaturated groups such as (meth) acryloyl groups, styryl groups, vinyl groups, and allyl groups in the molecule are not particularly limited.

The dental composition as the tooth substance adhesive primer can exhibit excellent dental adhesive performance to, especially an enamel by containing the phosphonic acid group-containing monomer. The phosphonic acid group-containing monomer is scarcely hydrolyzed in the molecule even under the acidic atmosphere in the presence of water and is excellent in storage stability since a phosphonic acid group is not bonded with an oxygen atom through an ester bond. Therefore, the packaging form may be not only a two-pack type packaging form divided into two sections, but also a one-pack type packaging form.

It is preferable to use, among these phosphonic acid group-containing monomers, a phosphonic acid group-containing monomer represented by the general formula (I):

[Chemical formula 10]

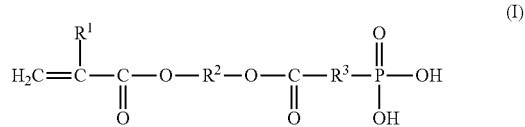

(I)

wherein $R^1$ represents a hydrogen atom or a methyl group, $R^2$ represents an alkylene group having 5 to 10 carbon atoms, and R represents an alkylene group having 1 to 6 carbon atoms, which has excellent dental adhesion and storage stability.

Specific examples of the phosphonic acid group-containing monomer represented by formula (I) include, but are not limited to, the following compounds.

[Chemical formula 11]

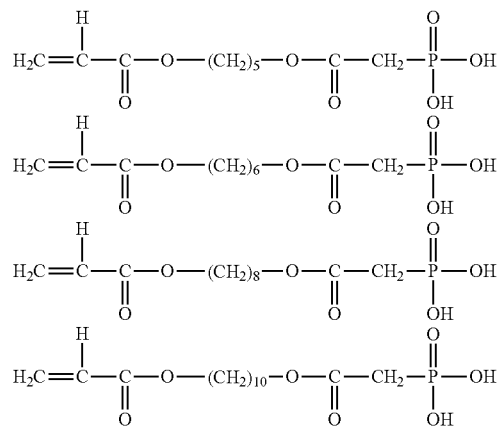

[Chemical formula 12]

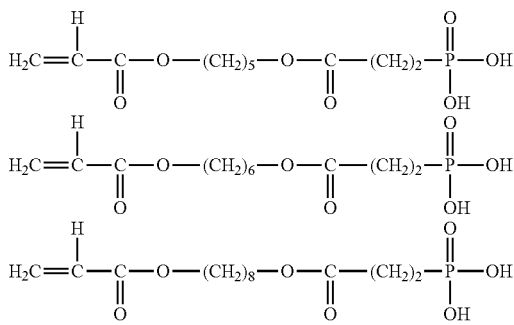

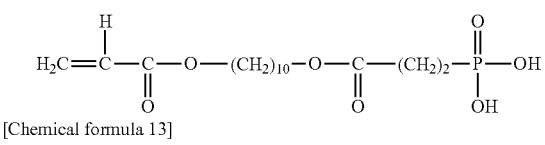

[Chemical formula 13]

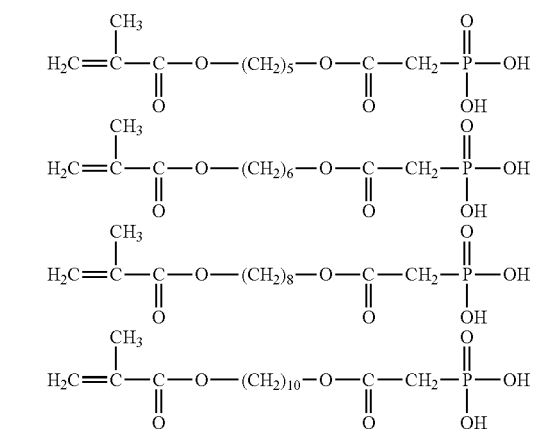

[Chemical formula 14]

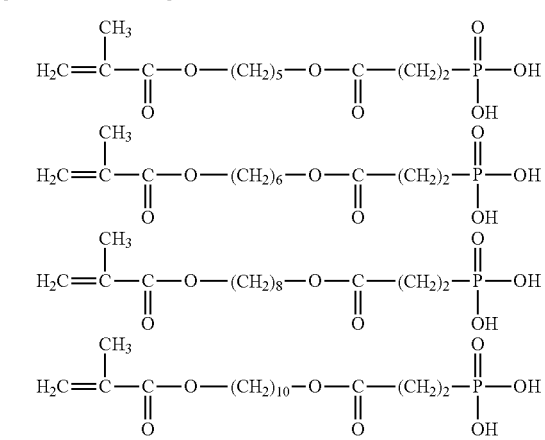

It is more preferable to use, among phosphonic acid group-containing monomers, 6-(meth)acryloyloxyhexyl phosphonoacetate, 6-(meth)acryloyloxyhexyl-3-phosphonopropionate, 10-(meth)acryloyloxydecyl-3-phosphonoacetate, 10-(meth)acryloyloxydecyl phosphonopropionate, and 5-(meth)acryloyloxypentyl-3-phosphonopropionate.

These inorganic acid group-containing monomers can also be used alone or in combination.

The content of the component (n) inorganic acid group-containing monomer can be appropriately selected according to the application or purpose and usage of the dental composition as the tooth substance adhesive primer, and is preferably within a range of 0.1 to 40.0 parts by weight based on 100 parts by weight of the total of the components of the dental composition as the tooth substance adhesive primer excluding the component (a) and the component (f).

When the content of these inorganic acid group-containing monomers is more than 40.0 parts by weight, since curability due to polymerizability deteriorates, an adverse influence is exerted on adhesive characteristics. In contrast, when the content of these inorganic acid group-containing monomers is less than 0.1 parts by weight, the effect is not recognized in adhesive property to enamel.

Although examples of the inorganic acid group-containing monomer are shown in the above, the inorganic acid group-containing monomer is not limited thereto and can also be used alone or in combination. In addition, not only a monomer with a short main chain but also be an oligomer, a prepolymer, a polymer or the like with a long main chain may be used as the inorganic acid group-containing monomer without any limitation.

Further, derivatives of the inorganic acid group-containing monomer such as a metallic salt, an ammonium salt, and an acid chloride obtained by partially neutralizing the acidic group of the inorganic acid group-containing monomer may also be used to the extent that the adhesive property to various adherends is not adversely affected.

The component (o): organic acid group-containing monomer used in case that the dental composition of the present disclosure is the tooth substance adhesive primer is not particularly limited as long as the monomer does not correspond to the component (a) and has an organic acid group. Specifically, known organic acid group-containing monomer(s) commonly used for a dental material can be used. Specific examples of the organic acid group contained in the organic acid group-containing monomer include a carboxyl group, a sulfonic acid group, a sulfinic acid group, a phenol group, an enol group, a thiophenol group, an oxime group, an aromatic sulfamide group, and a primary nitro group, secondary amide groups, and hydroxyl groups, but are not limited to.

In this case, it is preferable that the component (o): organic acid group-containing monomer is a carboxylic acid group-containing monomer.

Specific examples of the unsaturated group of the organic acid group-containing monomer are not limited to, but include a (meth) acryloyl group, a styryl group, a vinyl group, and an aryl group. It is preferable that an organic acid group-containing monomer has a (meth) acryloyl group among these unsaturated groups.

Further, these organic acid group-containing monomers may contain together other functional group such as an alkyl group, halogen, an amino group, a glycidyl group, and a hydroxy group in a molecule.

The polymer of an organic acid group-containing monomer in which a portion or the entirety of the acidic group forms a salt with an alkaline metal can be used and specific examples of an organic acid group-containing monomer having a (meth) acryloyl group as an unsaturated group are listed below.

Examples of the acidic group-containing monomer having a monocarboxylic acid group include, but are not limited to, (meth)acrylic acid, 2-chloro(meth)acrylic acid, 3-chloro (meth)acrylic acid, 2-cyano(meth)acrylic acid, N-(meth) acryloyl-p-aminobenzoic acid, N-(meth)acryloyl-5-aminosalicylic acid, 2-(meth)acryloyloxybenzoic acid, p-vinylbenzoic acid, and 5-(meth)acryloylaminopentylcarboxylic acid.

Specific examples of an acidic group-containing monomer having a sulfonate group are not limited to, but include 2-(meth) acrylamido-2-methylpropanesulfonic acid, styrenesulfonic acid, 2-sulfoethyl (meth) acrylate, 4-(meth) acryloyloxy benzenesulfonic acid, and 3-(meth) acryloyloxy propanesulfonic acid.

In case that the dental composition of the present disclosure is the tooth substance adhesive primer, it is particularly preferable that the component (o): organic acid group-containing monomer is a polycarboxylic acid group-containing monomer. The polycarboxylic acid group-containing monomer means a monomer having two or more carboxylic acid groups, or a group capable of easily reacting with water to form two or more carboxylic acid groups and at least one polymerizable unsaturated group in the molecule.

It is possible to use those having any functional group in the molecule without any limitation as long as these conditions are satisfied. In the polycarboxylic acid group-containing monomer, the kind and number of radical polymerizable unsaturated groups such as (meth)acryloyl groups, styryl groups, vinyl groups, and allyl groups in the molecule are not particularly limited. The dental composition as the tooth substance adhesive primer can exhibit excellent tooth substance adhesive performance to dentin by containing the polycarboxylic acid group-containing monomer.

Specific examples of the polycarboxylic acid group-containing monomer include, but are not limited to, aconitic acid, mesaconic acid, maleic acid, maleic anhydride, itaconic acid, itaconic anhydride, fumaric acid, glutaconic acid, citraconic acid, utraconic acid, 1,4-di(meth)acryloyloxyethylpyromellitic acid, 6-(meth)acryloyloxynaphthalene-1,2,6-tricarboxylic acid, 1-butene 1,2,4-tricarboxylic acid, 3-butene 1,2,3-tricarboxylic acid, 4-(meth)acryloyloxyethyltrimellitic acid and an anhydride thereof, 4-(meth)acryloyloxybutyltrimellitic acid and an anhydride thereof, β-(meth)acryloyloxyethyl hydrogen succinate, β-(meth)acryloyloxyethyl hydrogen maleate, 11-(meth)acryloyloxy-1,1-undecanedicarboxylic acid, 4-(meth)acryloyloxyethoxycarbonylphthalic acid, 4-(meth)acryloyloxybutyloxycarbonylphthalic acid, 4-(meth)acryloyloxyhexyloxycarbonylphthalic acid, 4-(meth)acryloyloxyoctyloxycarbonylphthalic acid, 4-(meth)acryloyloxydecyloxycarbonylphthalic acid and acid anhydride thereof, 6-(meth)acryloyloxy-1,1-hexanedicarboxylic acid, 8-(meth)acryloyloxy-1,1-octanedicarboxylic acid, 10-(meth)acryloyloxy-1,1-decanedicarboxylic acid, and 11-(meth) acryloyloxy-1,1-undecanedicarboxylic acid. These polycarboxylic acid group-containing monomers can also be used alone or in combination. It is more preferred to use, among these polycarboxylic acid group-containing monomers, 4-methacryloyloxyethyltrimellitic acid and an anhydride thereof, and 4-acryloyloxyethyltrimellitic acid and an anhydride thereof.

The content of the component (o): organic acid group-containing monomer can be appropriately selected according to the application or purpose usage of the dental composition as the tooth substance adhesive primer, and is preferably within a range of 0.1 to 40.0 parts by weight based on 100 parts by weight of the total of the components of the dental composition as the tooth substance adhesive primer excluding the component (a) and the component (f).

When the content of these organic acid group-containing monomers is more than 40.0 parts by weight, since curability due to polymerizability deteriorates, an adverse influence is exerted on adhesive characteristics. In contrast, when the content of these organic acid group-containing monomers is less than 0.1 parts by weight, the effect is not recognized in adhesion to dentin.

Although examples of the organic acid group-containing monomer are shown in the above, the organic acid group-containing monomer is not limited thereto and can also be used alone or in combination. In addition, not only a monomer with a short main chain but also be an oligomer, a prepolymer, a polymer or the like with a long main chain may be used as the organic acid group-containing monomer without any limitation.

Further, derivatives of the organic acid group-containing monomer such as a metallic salt, an ammonium salt, and an acid chloride obtained by partially neutralizing the acidic group of the organic acid group-containing monomer may also be used to the extent that the adhesion to various adherends is not adversely affected.

The content of the component (k): acid group-containing monomer in case that the dental composition is the tooth substance adhesive primer can be appropriately selected according to the application or purpose and usage of the dental composition as the tooth substance adhesive primer, and is preferably within a range of 0.2 to 80.0 parts by weight based on 100 parts by weight of the total of the components of the dental composition as the tooth substance adhesive primer excluding the component (a) and the component (f).

In order to further enhancing adhesive property to tooth substances or imparting adhesive property to various adherends containing noble metal in case that the dental composition is the tooth substance adhesive primer, the dental composition may contain component (u): sulfur atom-containing monomer containing a sulfur atom in the molecule and a silane compound alone, or in combination.

It is also effective to use component (u): sulfur atom-containing containing a sulfur atom in the molecule so as to impart adhesive property to noble metal to the dental composition as the tooth substance adhesive primer. The monomer containing a sulfur atom in the molecule can be used regardless of the kind and number of unsaturated groups as well as the presence or absence of another functional group.

The component (u): sulfur atom-containing monomer used in case that the dental composition is the tooth substance adhesive primer can be the same as the component (u): sulfur atom-containing monomer in case that the dental composition is the dental composite material composition.

It is also effective to use an organosilane compound having at least one polymerizable unsaturated group in the molecule so as to impart adhesive property to a ceramic or composite resin to the dental composition as the tooth substance adhesive primer. Any organosilane compound having a polymerizable unsaturated group in a molecule may be used regardless of the type and the number of unsaturated groups, the presence or absence of other functional groups. Specific examples of organosilane compounds having a polymerizable unsaturated group include, but are not limited to, vinyltrimethoxysilane, vinyltriethoxysilane, vinyltrichlorosilane, vinyl(6-methoxyethoxy)silane, γ-methacryloxypropyl trimethoxysilane or the like. These organosilane compounds can also be used alone or in combination.

The component (l): water contained as an essential component in case that the dental composition of the present disclosure is the tooth substance adhesive primer has a function of activating an acidic group of the component (k): acid group-containing monomer such as the component (n): inorganic acid group-containing monomer and component (o): organic acid group-containing monomer contained in the dental composition as the tooth substance adhesive primer thereby promoting a decalcification action to tooth substances and promoting penetration into tooth substances. Therefore, water can be used without any limitation as long as it does not contain impurities which exert an adverse influence on storage stability, biocompatibility, polymerizability and tooth substance adhesive property. It is preferred to use distilled water or ion-exchange water.

The content of water can be appropriately selected according to the application or purpose and usage of the dental composition as the tooth substance adhesive primer, and is preferably within a range of 0.1 to 80.0 parts by weight based on 100 parts by weight of the total of the components of the dental composition as the tooth substance adhesive primer excluding the component (a) and the component (f). When the content of water is more than 80.0 parts by weight, it is impossible to maintain the composition at a homogeneous state and separation arises, and thus an adverse influence is exerted on storage stability. In contrast, when the content of water is less than 0.1 parts by weight, it is impossible to obtain sufficient adhesion to various adherends including tooth substances.

The component (m): water-soluble organic solvent which is contained as an essential component in case that the dental composition of the present disclosure is the tooth substance adhesive primer plays a role, which is similar to that of a dissolution accelerator, of compatibilizing various polymerizable monomers including the component (n): inorganic acid group-containing monomer and the component (o): organic acid group-containing monomer, water, a polymerization catalyst and another component, which are contained in the dental composition as the tooth substance adhesive primer, in an optional ratio, and also has a function of promoting penetration of the dental composition as the tooth substance adhesive primer into tooth substances. Also the water-soluble organic solvent can decrease liquid viscosity of the dental composition as the tooth substance adhesive primer thereby improving operability such as dropping from a container or applying to a site to be adhered.

Specific examples of the water-soluble organic solvent include, but are not limited to, alcohols such as methanol, ethanol, 1-propanol, 2-propanol, and 1-butanol; ether compounds such as triethylene glycol monomethyl ether, triethylene glycol monoethyl ether, dipropylene glycol monomethyl ether, tetrahydrofuran, and dimethoxyethane; and ketone compounds such as acetone and methyl ethyl ketone. These water-soluble organic solvents can also be used alone or in combination. Among these water-soluble organic solvents, methanol, ethanol, 1-propanol, 2-propanol and acetone are preferred since they are excellent in compatibility with water, and acetone and ethanol are more preferred.

The content of the organic solvent can be appropriately selected according to the application or purpose and usage of the dental composition as the tooth substance adhesive primer, and is preferably within a range of 0.1 to 80.0 parts by weight based on 100 parts by weight of the total of the components of the dental composition as the tooth substance adhesive primer excluding the component (a) and the component (f). When the content of the organic solvent is more than 80.0 parts by weight, adhesive property to tooth substances deteriorates. In contrast, when the content of the organic solvent is less than 0.1 parts by weight, it is impossible to maintain the composition at a homogeneous state and separation arises, and thus an adverse influence is exerted on storage stability.

The component (f): polymerization catalyst contained as an essential component in the dental composition of the present disclosure as the tooth substance adhesive primer is not particularly limited and a known radical generator can be used without any limitation. The polymerization catalyst is roughly classified into a catalyst capable of initiating polymerization by mixing immediately before use (chemical polymerization catalyst), a catalyst capable of initiating polymerization by heating or warming (thermal polymerization catalyst), and a catalyst capable of initiating polymerization by light irradiation (component (w): photopolymerization catalyst) and all of these catalysts can also be used alone or in combination.

Examples of the above described chemical polymerization catalyst include a redox-type polymerization initiator system comprising an organic peroxide/an amine compound, an organic peroxide/an amine compound/a sulfinate, an organic peroxide/an amine compound/a borate compound, and a polymerization catalyst system such as organic boron compounds, perborates, permanganates, and persulfates which initiate polymerization by reacting with oxygen or water. Further, sulfinates, borate compounds and barbituric acids can initiate polymerization in the presence of water or a polymerizable monomer having an acidic group.

In this case, the organic peroxide can be the same as that in the case that the dental composition is the dental composite material composition.

In this case, the amine compound can be the same as that in the case that the dental composition is the dental composite material composition.

In this case, the sulfuric acid salts can be the same as that in the case that the dental composition is the dental composite material composition.

In this case, the borate compound can be the same as that in the case that the dental composition is the dental composite material composition.

Specific examples of the barbituric acids include, but are not limited to, barbituric acid, 1,3-dimethylbarbituric acid, 1,3-diphenylbarbituric acid, 1,5-dimethylbarbituric acid, 5-butylbarbituric acid, 5-ethylbarbituric acid, 5-isopropylbarbituric acid, 5-cyclohexylbarbituric acid, 1,3,5-trimethylbarbituric acid, 1,3-dimethyl-5-ethylbarbituric acid, 1,3-dimethyl-n-butylbarbituric acid, 1,3-dimethyl-5-isobutylbarbituric acid, 1,3-dimethyl-barbituric acid, 1,3-dimethyl-5-cyclopentylbarbituric acid, 1,3-dimethyl-5-cyclohexylbarbituric acid, 1,3-dimethyl-5-phenylbarbituric acid, 1-cyclohexyl-5-ethylbarbituric acid, 1-benzyl-5-phenylbarbituric acid and thiobarbituric acids, and salts thereof (alkali metal or alkali earth metals are particularly preferred). Examples of the salts thereof include, but are not limited to, sodium 5-butylbarbiturate, sodium 1,3,5-trimethylbarbiturate, calcium 1,3,5-trimethylbarbiturate, and sodium 1-cyclohexyl-5-ethylbarbiturate. These barbiturates can also be used alone or in combination.

When the dental composition as the tooth substance adhesive primer is used alone, these chemical polymerization catalysts must be separately contained in at least two packaging-forms. When the dental composition as the tooth substance adhesive primer is used together with another composition, both the dental composition as the tooth substance adhesive primer and another composition can contain the chemical polymerization catalyst so as to initiate chemical polymerization by bringing the dental composition as the tooth substance adhesive primer into contact with another composition.

Among these chemical polymerization catalysts, sulfinates, barbiturates and organic peroxide-tertiary amine are preferably used alone or in combination, and organic peroxide-tertiary amine, organic peroxide-tertiary amine-barbiturates and organic peroxide-tertiary amine-sulfinates are more preferably used.

The content of the chemical polymerization catalyst is preferably within a range of 0 to 15.0 parts by weight, and more preferably from 0.1 to 10.0 parts by weight, based on 100 parts by weight of the total of the components of the dental composition as the tooth substance adhesive primer excluding the component (a) and the component (f).

Examples of the component (w): photopolymerization catalyst include those composed of only a photosensitizer and those composed of a combination of a photosensitizer and a photopolymerization accelerator.

The photosensitizer is roughly classified into those in which polymerization is initiated by ultraviolet rays and those in which polymerization is initiated by visible rays.

Specific examples of the photosensitizer which can be used as the component (w): photopolymerization catalyst include, but are not limited to, α-diketones such as benzyl, camphorquinone, α-naphthyl, acetonaphthene, p,p'-dimethoxybenzyl, p,p'-dichlorobenzylacetyl, pentanedion, 1,2-phenanthrenequinone, 1,4-phenanthrenequinone, 3,4-phenanthrenequinone, 9,10-phenanthrenequinone, and naphthoquinone; benzoin alkyl ethers such as benzoin, benzoin methyl ether and benzoin ethyl ether; thioxanthones such as thioxanthone, 2-chlorothioxanthbne, 2-methylthioxanthone, 2-isopropylthioxanthone, 2-methoxythioxanthone, 2-hydroxythioxanthone, 2,4-diethylthioxanthone, and 2,4-diisopropylthioxanthone; benzophenones such as benzophenone, acetoinbenzophenone, p-chlorobenzophenone, and p-methoxybenzophenone; acylphosphine oxides such as 2,4,6-trimethylbenzoyldiphenylphosphine oxide and bis(2,6-dimethoxybenzoyl)-2,4,4-trimethylpentylphosphine oxide; α-aminoacetophenones such as 2-benzyl-dimethyl-amino-1-(4-morpholinophenyl)-butanone-1, and 2-benzyl-diethylamino-1-(4-morpholinophenyl)-propanone-1; ketals such as benzyl dimethyl ketal, benzyl diethyl ketal and benzyl(2-methoxyethyl ketal); and titanocenes such as bis(cyclopentadienyl)-bis[2,6-difluoro-3-(1-pyrrolyl)phenyl]-titanium, bis(cyclopentadienyl)-bis(pentanefluorophenyl)-titanium, and bis(cyclopentadienyl)-bis(2,3,5,6-tetrafluoro-4-disiloxyphenyl)-titanium. These photosensitizers can also be used alone or in combination.

Specific examples of the photopolymerization accelerator which can be used as the component (w): photopolymerization catalyst include, but are not limited to, tertiary amines such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N,N-dimethylaniline, m-chloro-N,N-dimethylaniline, p-dimethylaminobenzaldehyde, p-dimethylaminoacetophenone, p-dimethylaminobenzoic acid, ethyl p-dimethylaminobenzoate, p-dimethylaminobenzoic acid amino ester, methyl N,N-dimethylanthranate, N,N-dihydroxyethylaniline, N,N-dihydroxyethyl-p-toluidine, p-dimethylaminophenyl alcohol, p-dimethylaminostyrene, N,N-dimethyl-3,5-xylidin, 4-dimethylaminopyridine, N,N-dimethyl-α-naphthylamine, N,N-dimethyl-8-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate, and 2,2'-(n-butylimino) dimethanol; secondary amines such as N-phenylglycine; barbiturates such as 5-butylbarbituric acid, 1-benzyl-5-phenylbarbitur acid, 1,3,5-trimethylbarbituric acid, sodium 1,3,5-trimethylbarbiturate, and calcium 1,3,5-trimethylbarbiturate; tin compounds such as dibutyltin diacetate, dibutyltin dilaurate, dioctyltin dilaurate, dioctyltin diperacetate, dioctyltin bis(mercaptoacetic acid isooctyl ester) salt, and tetramethyl-1,3-diacetoxydistannoxane; aldehyde compounds such as laurylaldehyde and terephthalaldehyde; and sulfur-containing compounds such as dodecylmercaptan, 2-mercaptobenzooxazole, 1-decanethiol, and thiosalicylic acid. These photopolymerization accelerators can also be used alone or in combination.

It is effective to add, in addition to the above photopolymerization accelerator, citric acid, malic acid, tartaric acid, glycolic acid, gluconic acid, and oxycarboxylic acids such as α-oxyisobutyric acid, 2-hydroxypropanoic acid, 3-hydroxypropanoic acid, 3-hydroxybutanoic acid, 4-hydroxybutanoic acid and dimethylolpropionic acid so as to improve photopolymerization acceleration ability.

When the component (w): photopolymerization catalyst is used, one packaging form or a packaging form divided into two sections may be used without any limitation. Among these photopolymerization catalysts, a combination of α-diketone and a tertiary amine or α-diketone and tin compounds is preferred. More preferred is a combination of camphorquinone and an aromatic tertiary amine in which an amino group is directly bonded to the benzene ring such as ethyl p-N,N-dimethylaminobenzoate or an aliphatic tertiary amine having a double bond in the molecule such as N,N-dimethylaminoethyl methacrylate, or a combination of camphorquinone and tin compounds such as dibutyltin dilaurate and dioctyltin dilaurate. The content of the component (w): photopolymerization catalyst is preferably within a range of 0.1 to 15.0 parts by weight, more preferably from 0.1 to 10.0 parts by weight, and most preferably from 0.1 to 8.0 parts by weight, based on 100 parts by weight of the total of the components of the dental composition as the tooth substance adhesive primer excluding the component (a) and the component (f).

As the thermal polymerization catalyst capable of initiating polymerization by heating or warming other than the above organic peroxide, azo compounds such as azobisisobutyronitrile, methyl azobisisobutyrate and azobiscyanovaleric acid are preferably used, but are not limited to. These thermal polymerization catalysts can also be used alone or in combination.

According to the application, coumarin-based, cyanine-based and thiazine-based sensitizing dyes; photo acid generators which are irradiated with light to generate Brønsted acid or Lewis acids, such as a halomethyl group substituted-s-triazine derivative, diphenyliodonium salt compound, etc.; quaternary ammonium halides; and transition metal compounds can be appropriately used.

The dental composition as the tooth substance adhesive primer may contain the component (s): hydrophobic monomer. As the component (s): hydrophobic monomer, a monofunctional or polyfunctional monomer which exhibits hydrophobicity can be used without any limitation, regardless of the kind of a radical polymerizable unsaturated group, as long as the monomer does not correspond the component (a) the component (k). Other constitution of the hydrophobic monomer can be the same as the case that the dental composition is the dental composite material composition, except for the constitution described below. In this case, hydrophobic monomer having monofunctional group, hydrophobic monomer having aromatic bifunctional group, hydrophobic monomer having aliphatic bifunctional group, hydrophobic monomer having aliphatic trifunctional group, hydrophobic monomer having aliphatic tetrafunctional group, and the urethane-based hydrophobic monomer may have the same constitution as the case that the dental composition is the dental composite material composition.

The content of the hydrophobic monomer compounded in the dental composition as the tooth substance adhesive primer is preferably within a range of 1.0 to 50.0 parts by weight, and more preferably from 1.0 to 30.0 parts by weight, based on 100 parts by weight of the total of the components of the dental composition as the tooth substance adhesive primer excluding the component (f): polymerization catalyst and the component (a). When the content deviates from the above range, wettability to the surface of the adherend to be adhered deteriorates and curability due to polymerizability deteriorates, and thus adhesive characteristics deteriorate.

A preferred aspect of the dental composition as the tooth substance adhesive primer is that it does not contain the component (r): hydrophilic monomer which is easily compatible with water. The hydrophilic monomer has the effect of compatibilizing a hydrophobic component contained in the dental composition with a hydrophilic component in an optional ratio, and enhancing adhesive property by improving permeability and wettability to an interface to be adhered. However, since the dental composition as the tooth substance adhesive primer is present under an acidic atmosphere, deterioration and change in quality of the hydrophilic monomer are caused by hydrolysis, and thus adhesive property may deteriorate. Furthermore, the hydrophilic monomer originally has poor curability and causes hydrolysis in case of cured since it has high affinity with water, and thus a problem is recognized in durability on adhesion.

Regarding the "hydrophilic monomer" as used herein, a monomer having solubility in 100 parts by weight of water at 23° C. of 10 parts by weight or more is defined as a hydrophilic monomer. That is, when 10 g of a monomer is added in 100 g of water maintained at 23° C. in a sample bottle, followed by stirring with mixing for 10 minutes and further standing, if the mixture is compatible in a transparent or semitransparent state in the sample bottle, the monomer is defined as a hydrophilic monomer.

Such a hydrophilic monomer can have the same constitution as the case that the dental composition is a dental composite material composition, except for the constitution described below. In this case, a hydrophilic monomer having a (meth)acryloyl group as a radical polymerizable unsaturated group can have the same constitution as the case that the dental composition is the dental composite material composition, and the hydrophilic monomer which is preferably not contained can have the same constitution as the preferred hydrophilic monomer in case that the dental composition is the dental composite material composition.

The dental composition as the tooth substance adhesive primer can contain the component (b): filler for the purpose of improving operability by thickening the dental composition as the tooth substance adhesive primer or improving adhesive property by imparting a mechanical strength to a bond interface layer. The filler is not particularly limited and fillers known as a dental filler can be used. Examples of the filler include inorganic filler and/or organic filler and/or organic-inorganic composite filler, and these fillers can be used alone or in combination.

The shape of these fillers may be any shape such as a spherical shape, needle shape, tabular shape, ground shape or scaly shape and is not particularly limited. Furthermore, the diameter of these filler is not particularly limited, and is preferably within a range of 0.001 to 10 μm, and more preferably 0.01 to 5 μm, in consideration of problems such as sedimentation and separation.

Among these fillers, AEROSIL, as ultrafine particles, produced by a vapor phase method, or silica-zirconia oxide particles, as ultrafine silica composite particles, produced from the solution of the sol-gel reaction are effective for the dental composition as the tooth substance adhesive primer since they function as a thickener when mixed in the tooth substance adhesive primer. Specific examples of AEROSIL include AEROSIL 200, AEROSIL OX50, AEROSIL R972, AEROSIL R974, AEROSIL R8200, AEROSIL R711, AEROSIL DT4, Aluminum Oxide C, and Titanium Dioxide P25. Also cohesive inorganic fillers obtained by intended cohesion of the ultrafine particles may be used without causing any problems.

It is possible to optionally add components, for example, ultraviolet absorbers such as 2-hydroxy-4-methylbenzophenone; polymerization inhibitors such as hydroquinone, hydroquinone monomethyl ether, and 2,5-di-tertiary butyl-4-methylphenol; discoloration inhibitors; antibacterial agent; coloration pigment; and another conventionally known additive; in the dental composition as the tooth substance adhesive primer.

The using method of the dental composition as the tooth substance adhesive primer is not specifically limited, and the dental composition as the tooth substance adhesive primer may be used not only singly but also in appropriate combination with other composition such as an etching material, a primer, a bonding material, a self-etching primer, a ceramic primer, a metal primer, and a precious metal primer.

The dental composition as the tooth substance adhesive primer has a feature that it is excellent in storage stability according to the constitution of components contained in the composition. Therefore, the dental composition as the tooth substance adhesive primer can be formed into a one-pack packaging form. The dental composition as the tooth substance adhesive primer can also be formed into a two- or higher-pack packaging form depending on the ratio of components to be compounded in the dental composition as the tooth substance adhesive primer, the kind of the polymerization catalyst, the type of the polymerization catalyst, the using method, purpose or the like, which can be appropriately selected.

The dental composition of the present disclosure may be a dental primer for modifying a surface of a dental restoration which is prepared by cutting and machining an inorganic sintered body such as a block and a disk by using CAD/CAM technique. The materials of the inorganic sintered body are not limited particularly but specific examples of the materials of the inorganic sintered body include a composition containing silica, alumina, or zirconia as a main component. In addition, the dental restoration prepared by cutting and machining an inorganic sintered body may include pigment.

The dental composition as the dental primer may be used for a composite resin in which an inorganic filler is exposed to the adhesive surface.

The dental composition may be used for a dental restoration which is prepared by building up. This dental restoration may be prepared by building up and sintering an inorganic filler, and is generally called as porcelain.

As the component (p): organic solvent used in case that the dental composition of the present disclosure is the dental primer, for example, methanol, ethanol, n-propanol, isopropanol and anhydride thereof, and acetone and methyl ethyl ketone can be utilized. Methanol, ethanol, propanol, acetone and anhydride thereof are preferable. Anhydrous ethanol and acetone are more preferable. Anhydrous ethanol is further preferable. The content of the organic solvent is preferably 70 to 90 wt. %, and more preferably 80 to 98 wt. %.

The component (g): silane coupling agent used in case that the dental composition of the present disclosure is the dental primer is not particularly limited, but specifically the same one as the case that the dental composition is the dental composite material composition is preferably used, and particularly preferably, methyltrichlorosilane, dimethyldichlorosilane, γ-methacryloyloxypropyltrimethoxysilane, and hexamethyldisilazane are used. The content of silane coupling agent is preferably 0.1 to 15 wt. %, and more preferably 1 to 8 wt. %.

Among the component (q): acid anhydride and/or weakly acidic compound used in case that the dental composition of the present disclosure is the dental primer, any weakly acidic compound having pH of 2 or more may be used as the weakly acidic compound. Preferable weakly acidic compound is a carboxylic acid based-compound, and more preferable weakly acidic compound consists of a carboxylic acid based-compound. As the carboxylic acid based-compound, tartaric acid, malic acid, citric acid, maleic acid, itaconic acid and aconitic acid are preferable. In particular, citric acid, maleic acid, itaconic acid and anhydride thereof are more preferable. It is preferable that the weakly acidic compound is an acid anhydride.

Among the component (q): acid anhydride and/or weakly acidic compound used in case that the dental composition of the present disclosure is the dental primer, not only the acid anhydride of the organic acid such as carboxylic acid but also the acid anhydride of the inorganic acid such as a sulfuric acid, a nitric acid and a phosphoric acid can be used as the acid anhydride. As the specific examples of the acid anhydride of the inorganic acid, disulfuric acid (pyrosulfuric acid) as an anhydride of the sulfuric acid, trifluoromethanesulfonic acid anhydride as an anhydride of sulfonic acid, dinitrogen pentoxide as a nitrate anhydride, pyrophosphoric acid (diphosphoric acid) and diphosphorus (tetraphosphorus decaoxide) pentoxide as an anhydride of phosphoric acid, and, diphosphorus trioxide as an anhydride of the phosphorous may be used.

Preferable acid anhydride is an acid anhydride having pH of 2 or more, and is a carboxylic acid based-compound, and more preferable acid anhydride consists of a carboxylic acid based-compound. As the carboxylic acid based-compound, tartaric acid, malic acid, citric acid, maleic acid, itaconic acid and aconitic acid are preferable. In particular, citric acid, maleic acid, itaconic acid and anhydride thereof are more preferable. It is preferable that the acid anhydride contains an anhydride of a carboxylic acid, a sulfonic acid, a nitric acid and/or a phosphoric acid.

The content of the component (q): acid anhydride and/or weakly acidic compound is preferably 0.1 to 5 wt. %, and more preferably 0.1 to 2 wt. %.

The dental composition as the dental primer may be compounded with an antioxidant such as hydroquinone, hydroquinone monomethyl ether and butylated hydroxytoluene appropriately. In addition, the dental primer of the present disclosure may be used in gel state by compounding a viscosity control agent such as colloidal silica, glycerin and polyethylene glycol. In addition, it is preferable that the dental composition as the dental primer does not contain the component (l): water. It is preferable that the dental composition as the dental primer does not contain other monomer.

It is preferable that the adhesive material used in a set with a dental composition as a dental primer contains the component (a) and/or the component (c): monomer other than the component (a), and the component (f): polymerization catalyst, and the resin cement used in a set with a dental composition as a dental primer contains the component (a) and/or the component (c): monomer other than the component (a), the component (f): polymerization catalyst and the component (b): filler. The composite resin used in a set with a dental composition as a dental primer and an adhesive material or a resin cement contains the component (a), and/or the component (c): monomer other than the component (a), and the component (f): polymerization catalyst, and the component (b): filler.

The component (c): monomer other than the component (a) is not particularly limited as long as it is a monomer having a polymerizable group. Specifically, known monofunctional and/or polyfunctional monomers generally used for dental materials can be used. Preferable monomers include monomers having an acryloyl and/or methacryloyl group.

Such a monomer can have the same constitution as the case that the dental composition is the dental composite material composition, except for the constitution described below. In this case, monofunctional monomer (non-crosslinkable monomer), aromatic bifunctional monomer (crosslinkable monomer), aliphatic bifunctional monomer (crosslinkable monomer), trifunctional monomer (crosslinkable monomer), tetrafunctional monomer (crosslinkable monomer) and the urethane-based monomer may have the same constitution as the case that the dental composition is the dental composite material composition.

A monomer other than the above described the (meth)acrylate-based monomer, for example, a monomer, an oligomer or a polymer having at least one polymerizable group in the molecule may be used for the component (c): monomer other than the component (a), in accordance with purpose. The monomer other than the (meth)acrylate type monomers may have a substituent such as an acidic group and a fluoro group in one molecule. In case that the dental composition of the present disclosure is the dental primer, the component (c): monomer other than the component (a) may be a single component, or may be a mixture of a plurality of monomers. When the viscosity of the monomer is extremely high at room temperature or the monomer is a solid, the monomer is preferably combined with a monomer low in viscosity and used as a polymerizable monomer mixture. In such a combination, the monomer may be used in combinations of two, or three or more.

The component (c): monomer other than the component (a) may include only monofunctional monomers, and may additionally include polyfunctional monomers. A preferable monomer includes an aromatic compound of a bifunctional monomer and an aliphatic compound of a bifunctional polymerizable monomer. A more preferable monomer includes 2,2-bis(4-(3-methacryloyloxy-2-hydroxypropoxy)phenyl)propane (Bis-GMA) and triethylene glycol dimethacrylate (TEGDMA).

The component (c): monomer other than the component (a) may include a monomer containing an acid group such as a phosphoric acid group, a carboxylic acid group, a phosphonic acid, a sulfonic acid group or the like in the molecule as a part of the polymerizable monomer. The component (c): monomer other than the component (a) may include a component (u): sulfur atom-containing monomer containing a sulfur atom in the molecule.

It is preferable that the content of the monomer containing an acid group such as a phosphoric acid group, a carboxylic acid group, a phosphonic acid, a sulfonic acid group or the like in the molecule or the component (u): sulfur atom-containing monomer containing a sulfur atom in the molecule is preferably 0.5 to 20 wt. % based on 100 wt. % of the component (c): monomer other than the component (a).

Such a monomer can have the same constitution as the case that the dental composition is the dental composite material composition.

The component (b): filler is not specifically limited, and a filler known in the art such as an inorganic filler and/or an organic filler and/or an organic-inorganic composite filler, for example, may be used without any limitation. Other constitution of the component (b): filler can be the same constitution as the case that the dental composition is the dental composite material composition, except for the constitution described below. In this case, the shape and the circularity of the filler, and the inorganic filler can be the same as those in the case that the dental composition is the dental composite material composition.

The average particle diameter of such an inorganic filler is not particularly limited, and is preferably within a range of 0.1 to 10 μm, more preferably within a range of 0.3 to 5 μm.

In this case, the organic filler and the organic-inorganic composite filler can have the same constitution as that in case that the dental composition is the dental composite material composition, except for the constitution described below.

Preferably the average particle diameter of the organic filler and the organic-inorganic composite filler is within a range of 0.1 to 100 μm. More preferably, the average particle diameter thereof is within a range of 1 to 50 μm and, yet more preferably is within a range of 2 to 30 μm. Such inorganic, organic and organic-inorganic composite fillers can be each used singly or in combinations of several types.

The filler such as the inorganic, organic and organic-inorganic composite filler can be used with the particle surface thereof being subjected to a surface treatment by a known method.

The surface treatment agent and the surface treatment method that can be used for the surface treatment can be the same as the case that the dental composition is the dental composite material composition.

The filler surface may be subjected to a surface treatment by a special surface treatment agent and/or a special surface treatment method for the purpose of multi-functionalizing the filler, without any limitation.

The content of the component (b): filler is preferably 0 to 20 parts by weight based on 100 parts by weight of whole monomer.

The component (f): polymerization catalyst in case that the dental composition of the present disclosure is the dental primer is not particular limited, but a known radical generator may be used. The polymerization catalysts are generally classified into chemical polymerization initiators that initiate polymerization by mixing upon use and photopolymerization initiator that initiate polymerization by light irradiation.

Among such polymerization catalysts, examples of chemical polymerization initiators include redox type polymerization initiator systems comprising an organic peroxide/an amine compound or an organic peroxide/an amine compound/a sulfinic acid salt, or an organic peroxide/an amine compound/a borate compound, and organometal type initiator systems that initiate polymerization by reacting with oxygen or water.

In this case, the organic peroxide can be the same as that in the case that the dental composition is the dental composite material composition.

In this case, the amine compound can be the same as that in the case that the dental composition is the dental composite material composition.

In this case, the sulfuric acid salt can be the same as that in the case that the dental composition is the dental composite material composition.

In this case, the borate compound can be the same as that in the case that the dental composition is the dental composite material composition.

In this case, the organometal type polymerization initiator can be the same as that in the case that the dental composition is the dental composite material composition.

Among such polymerization catalysts, the photopolymerization initiator may be a photosensitizer. The photosensitizer may be used alone or in combination with a photopolymerization promotor.

In this case, the photosensitizer can be the same as the photosensitizer in the case that the dental composition is the dental composite material composition.

In this case, photopolymerization promotors can be the same as the photopolymerization promotors in the case that the dental composition is the dental composite material composition.

These polymerization catalysts may be used alone or as a mixture of two or more thereof. In addition, these polymerization catalysts may be used in combination irrespective of the polymerization form and the kind of polymerization catalysts. The content of a polymerization catalysts may be appropriately determined depending upon the use. In general, the content of polymerization catalyst may be selected from a range of 0.1-10 parts by weight based on whole monomers.

The photopolymerization initiator is preferably a combination of an α-diketone and a tertiary amine and more preferably a combination of camphorquinone with an aromatic amine having an amino group directly bound to the benzene ring such as ethyl p-N,N-dimethylaminobenzoate or with an aliphatic amine having a double bond in the molecule such as N,N-dimethylaminoethyl methacrylate.

As the component (c): monomer other than the component (a) used in case that the dental composition of the present disclosure is the dental adhesive composition, any monomer can be used without any limitation, as long as the monomer does not correspond to the component (a). In particular, it is preferable to contain the component (r): hydrophilic monomer and the component (s): hydrophobic monomer. By compounding the component (r): hydrophilic monomer and the component (s): hydrophobic monomer into a dental composition as a dental adhesive composition, since it is well compatible with the primer applied to the tooth substance and familiar with the adhesive body initial adhesion and adhesive durability are improved. The component (r): hydrophilic monomer has the effect of enhancing adhesive property by improving permeability and wettability to an interface to be adhered by compounding in the dental adhesive composition. As the component (r): hydrophilic monomer, a monofunctional or polyfunctional monomer which exhibits hydrophilicity can be used without any limitation, regardless of the kind of a radical polymerizable unsaturated group, as long as the monomer does not correspond the component (a). Other constituent of the hydrophilic monomer can be the same constitution as the case that the dental composition is the dental composite material composition, except for the constitution described below. In this case, a hydrophilic monomer having a (meth)acryloyl group as a radical polymerizable unsaturated group and a preferable hydrophilic monomer can have the same constitution as the case that the dental composition is the dental composite material composition.

The content of the hydrophilic monomer compounded in the dental composition as a dental adhesive composition is preferably 5 to 90 parts by weight, more preferably 5 to 60 parts by weight based on 100 parts by weight of the total weight of the component (r): hydrophilic monomer and the component (s): hydrophobic monomer contained in the dental composition as the dental adhesive composition. When the content deviates from the above range, wettability to the surface of the adherend to be adhered deteriorates and polymerizability is deteriorated, and thus adhesive property deteriorate.

In case that the dental composition of the present disclosure is the dental adhesive composition, as the component (s): hydrophobic monomer, a monofunctional or polyfunctional monomer which exhibits hydrophobicity can be used without any limitation, regardless of the kind of a radical polymerizable unsaturated group, as long as the monomer does not correspond to the component (a). Other constitution of the hydrophobic monomer can be the same constitution as the case that the dental composition is the dental composite material composition, except for the constitution described below. In this case, hydrophobic monomer having monofunctional group, hydrophobic monomer having aromatic bifunctional group, hydrophobic monomer having aliphatic bifunctional group, hydrophobic monomer having aliphatic trifunctional group, hydrophobic monomer having aliphatic tetrafunctional group, and the urethane-based hydrophobic monomer may have the same constitution as the case that the dental composition is the dental composite material composition.

The content of the hydrophobic monomer compounded in a dental composition as a dental adhesive composition is preferably 10 to 95 parts by weight, more preferably 40 to 95 parts by weight based on 100 parts by weight of the total weight of the component (r): hydrophilic monomer and the component (s): hydrophobic monomer contained in the dental composition as the dental adhesive composition. When the content deviates from the above range, wettability to the surface of the adherend to be adhered deteriorates and polymerizability is deteriorated, and thus adhesive property deteriorate.

In case that the dental composition is the dental adhesive composition, the component (c): monomer other than the component (a) is contained in a proportion of 50.0 to 99.8 wt. %, preferably 50.0 to 97.5 wt. %.

The dental adhesive composition of the present disclosure preferably does not contain the component (i): acidic group-containing monomer. When the component (i): acidic group-containing monomer is contained in the dental composition as the dental adhesive composition, deterioration in physical properties may be led.

It is necessary to modify the adhesive surface with a primer before using the dental composition of the present disclosure as the dental adhesive composition. The adhesive component compounded in the primer may contain at least one or more of the component (i): acidic group-containing monomer.

Further, the kind of acidic group contained in the acidic group-containing monomer is not particularly limited, and any acidic group-containing monomer having an acidic group can be used. Other constitution of the acidic group-containing monomer can be the same constitution as the case that the dental composition is the dental resin cement, except for the constitution described below. In this case, an acidic group-containing monomer having a phosphoric acid ester, an acidic group-containing monomer having a pyrophosphoric acid group, a carboxylic acid group-containing monomer, an acidic group-containing monomer having a phosphonic acid group, and an acidic group-containing monomer having sulfonic acid group, and the preferable acidic group-containing monomer may have the same constitution as the case that the dental composition is the dental resin cement.

Examples of the acidic group-containing monomer having a thiophosphoric acid group include, but are not limited to, 10-(meth)acryloyloxydecyl dihydrogen dithiophosphate.

Although examples of the acidic group-containing monomer are shown in the above, the acidic group-containing monomer is not limited thereto and can also be used alone or in combination. In addition, not only a monomer with a short main chain but also be an oligomer, a prepolymer, a polymer or the like with a long main chain may be used as the acidic group-containing monomer without any limitation.

Further, derivatives of the acidic group-containing monomer such as a metallic salt, an ammonium salt, and an acid chloride obtained by partially neutralizing the acidic group of the acidic group-containing monomer may also be used to the extent that the adhesive property to various adherends is not adversely affected.

Among these acidic group-containing monomers, it is preferable to use 10-(meth)acryloyloxydecyl dihydrogenphosphate, 6-(meth)acryloyloxyhexyl-3-phosphonoacetate, 4-methacryloyloxyethyltrimellitate and anhydride thereof, 4-acryloyloxyethyltrimellitate and anhydride thereof or the like. The content of the acidic group-containing monomer in the primer can be appropriately selected according to the application or purpose and usage of the dental composition as the dental adhesive composition, and is preferably within a range of 0.1 to 30.0 wt. %. When the content of the acidic group-containing monomer exceeds 30 wt. %, the polymerization of other monomers is prevented, which may adversely affect the adhesive property. In contrast, when the content of acidic group-containing monomer is less than 0.1 wt. %, the effect is not recognized in adhesion to tooth substance.

It is also effective to use component (u): sulfur atom-containing containing a sulfur atom in the molecule as an adhesive component compounded in the primer so as to impart adhesive property to noble metal to the dental composition as the dental adhesive composition. The monomer containing a sulfur atom in the molecule can be used regardless of the kind and number of unsaturated groups as well as the presence or absence of another functional group.

Specific examples of the component (u): sulfur atom-containing monomer containing a sulfur atom in the molecule and having a (meth)acryloyl group as an saturated group include, but are not limited to, (meth)acrylate having a triazinethiol group, (meth)acrylate having a mercapto group, (meth)acrylate having a polysulfide group, (meth)acrylate having a thiophosphate group, (meth)acrylate having a cyclic disufide group, (meth)acrylate having a mercaptodithiazole group, (meth)acrylate having a thiouracil group, (meth)acrylate having a thiirane group, or the like. The component (u): sulfur atom-containing monomer containing a sulfur atom in the molecule may be used singly or a plural combinations. The content of the component (u): sulfur atom-containing monomer containing a sulfur atom in the molecule can be appropriately selected according to the application or purpose and usage, and is preferably within a range of 0.01 to 10.0 wt. %. When the content of the component (u): sulfur atom-containing monomer containing a sulfur atom in the molecule exceeds 10.0 wt. %, the polymerization of other monomers is prevented, which may adversely affect the adhesive property. In contrast, when the content of this monomer is less than 0.01 wt. %, it is impossible to obtain sufficient adhesion to noble metal.

The component (f): polymerization catalyst used in case that the dental composition of the present disclosure is the dental adhesive composition is not particularly limited and a known radical generator can be used without any limitation.

The component (f): polymerization catalyst can have the same constitution as the case that the dental composition is the tooth substance adhesive primer, except for the constitution described below. In this case, a chemical polymerization catalyst, an organic peroxide, an amine compound, a sulfinate salt, a borate compound, and a barbituric acid may have the same constitution as the case that the dental composition is the tooth substance adhesive primer.

When the dental composition as the dental adhesive composition is used, these chemical polymerization catalysts must be separately contained in at least two packaging-forms. Further, both the dental composition as the dental adhesive composition and primer can contain the chemical polymerization catalyst so as to initiate chemical polymerization by bringing the dental composition as the dental adhesive composition into contact with the primer.

Among chemical polymerization catalysts, sulfinates, barbiturates and organic peroxide-tertiary amine are preferably used alone or in combination, and organic peroxide-tertiary amine, organic peroxide-tertiary amine-barbiturates and organic peroxide-tertiary amine-sulfinates are more preferably used.

The content of chemical polymerization catalyst is preferably within a range of 0.1 to 15.0 wt. % and more preferably 0.1 to 10.0 wt. %.

The photopolymerization catalyst can have the same constitution as the case that the dental composition is the tooth substance adhesive primer, except for the constitution described below. In this case, a photosensitizer, a photopolymerization accelerator, and an oxycarboxylic acid may have the same constitution as the case that the dental composition is the tooth substance adhesive primer.

A packaging form and a preferable combination in case of using the photopolymerization catalyst may have the same constitution as the case that the dental composition is the tooth substance adhesive primer.

The content of the component (w): photopolymerization catalyst is preferably within a range of 0.1 to 15.0 wt. %, more preferably from 0.1 to 10 wt. %, and most preferably from 0.1 to 8 wt. %.

A thermal polymerization catalyst, a sensitizing dye, a photoacid generator, a quaternary ammonium halide, a transition metal compound and the like which may be contained in a dental composition as a dental adhesive composition may have the same constitution as the case that the dental composition is the tooth substance adhesive primer.

AEROSIL which is a ultrafine particle and produced by a gas phase method or a silica-zirconia oxide particle which is a ultrafine particle silica composite particle and produced in a solution of a sol-gel reaction or the like may contained as a thickener in the dental composition as the dental adhesive composition. Specific examples of AEROSIL include AEROSIL 200, AEROSIL OX50, AEROSIL R972, AEROSIL R974, AEROSIL R8200, AEROSIL R711, AEROSIL DT4, Aluminum Oxide C, and Titanium Dioxide P25. It is possible to optionally add components, for example, ultraviolet absorbers such as 2-hydroxy-4-methylbenzophenone; polymerization inhibitors such as hydroquinone, hydroquinone monomethyl ether, and 2,5-ditertiary butyl-4-methylphenol; discoloration inhibitors; antibacterial agents; coloration pigments; and another conventionally known additives in the dental composition as the dental adhesive composition.

As the using method in case of the dental adhesive composition, the dental composition of the present disclosure may be used in appropriate combination with other treating materials such as an etching material, a primer, a self-etching primer, a ceramic primer, a metal primer, and a precious metal primer.

The packaging form in case that the dental composition of the present disclosure is the dental adhesive composition is not particularly limited, and may be appropriately selected according to the application from a single package or in a plurality of packages of two or more depending on the storage stability of the dental composition as a dental adhesive composition, the ratio of components to be compounded in the dental composition as a dental adhesive composition, the type of the polymerization catalyst, the using method, purpose or the like.

When the component (l): water or the component (p) organic solvent is contained in the dental composition as the dental adhesive composition, deterioration in physical properties may be led.

In case of using alone or in combination with other treatment material, the dental composition of the present disclosure in case of the tooth substance adhesive composition contains at least one of the component (i): acidic group-containing monomer in order to further enhance its adhesive property.

The kind of acidic group contained in the acidic group-containing monomer is not particularly limited, and any acidic group-containing monomer having an acidic group can be used as long as the monomer does not correspond to the component (a). Other constitution of acidic group-containing monomer can be the same constitution as the case that the dental composition is the dental adhesive composition, except for the constitution described below. In this case, an acidic group-containing monomer having a phosphoric acid ester, an acidic group-containing monomer having a pyrophosphoric acid group, a carboxylic acid group-containing monomer, an acidic group-containing monomer having a phosphonic acid group, an acidic group-containing monomer having sulfonic acid group and an acidic group-containing monomer having thiophosphate group, and the preferable acidic group-containing monomer may have the same constitution as the case that the dental composition is the dental adhesive composition.

The content of the acidic group-containing monomer can be appropriately selected according to the application or purpose and usage of the dental composition as the tooth substance adhesive composition, and is preferably within a range of 0.1 to 30.0 wt. %. When the content of the acidic group-containing monomer exceeds 30 wt. %, the polymerization of other monomers is prevented, which may adversely affect the adhesive property. In contrast, when the content of acidic group-containing monomer is less than 0.1 wt. %, the effect is not recognized in adhesion to tooth substance.

As the component (t): monomer other than the component (a) and the component (i): acidic group-containing monomer used in case that the dental composition of the present disclosure is the tooth substance adhesive composition, any monomer can be used without any limitation, as long as the monomer does not correspond to the component (a) and the component (i). In particular, it is preferable to contain the component (r): hydrophilic monomer and the component (s): hydrophobic monomer. By compounding the component (r): hydrophilic monomer and the component (s): hydrophobic monomer into a dental composition as a tooth substance adhesive composition, since it is well compatible with the tooth substance, initial adhesion and adhesive durability are improved.

The component (r): hydrophilic monomer has the effect of enhancing adhesive property by improving permeability and wettability to an interface to be adhered by compounding in the dental composition as the tooth substance adhesive composition. As the hydrophilic polymerizable monomer, a monofunctional or polyfunctional monomer which exhibits hydrophilicity can be used without any limitation, regardless of the kind of a radical polymerizable unsaturated group, as long as the monomer does not correspond to the component (a) and the component (i). Other constituent of a hydrophilic monomer can be the same constitution as the case that the dental composition is a dental composite material composition, except for the constitution described below. In this case, a hydrophilic monomer having a (meth)acryloyl group as a radical polymerizable unsaturated group and a preferable hydrophilic monomer can have the same constitution as the case that the dental composition is the dental composite material composition.

The content of the hydrophilic monomer compounded in a dental composition as a tooth substance adhesive composition is preferably 5 to 90 parts by weight, more preferably 20 to 90 parts by weight based on 100 parts by weight of the total weight of component (r): hydrophilic monomer and component (s): hydrophobic monomer contained in the dental composition as the tooth substance adhesive composition. When the content deviates from the above range, wettability to the surface of the adherend to be adhered deteriorates and polymerizability is deteriorated, and thus adhesive property deteriorate.

In case that the dental composition of the present disclosure is a dental tooth substance adhesive composition, as the component (s): hydrophobic monomer, a monofunctional or polyfunctional monomer which exhibits hydrophobicity can be used without any limitation, regardless of the kind of a radical polymerizable unsaturated group, as long as the monomer does not correspond to the component (a) and the component (i). Other constituent of a hydrophobic monomer can be the same constitution as the case that the dental composition is the dental composite material composition, except for the constitution described below. In this case, hydrophobic monomer having monofunctional group, hydrophobic monomer having aromatic bifunctional group, hydrophobic monomer having aliphatic bifunctional group, hydrophobic monomer having aliphatic trifunctional group, hydrophobic monomer having aliphatic tetrafunctional group, and the urethane-based hydrophobic monomer may have the same constitution as the case that the dental composition is the dental composite material composition.

The content of the hydropobic monomer compounded in a dental composition as a tooth substance adhesive composition is preferably 5 to 90 parts by weight, more preferably 10 to 80 parts by weight based on 100 parts by weight of the total weight of component (r): hydrophilic monomer and component (s): hydrophobic monomer contained in the dental composition as the tooth substance adhesive composition. When the content deviates from the above range, there is a case that wettability to the surface of the adherend to be adhered deteriorates and polymerizability is deteriorated, and thus adhesive property deteriorate.

In case that the dental composition of the present disclosure is the tooth substance adhesive composition, the component (t): monomer other than the component (a) and the component (i) is contained in a proportion of 50.0 to 99.5 wt. %, preferably 50.0 to 97.5 wt. %.

It is also effective to use component (u): sulfur atom-containing monomer containing a sulfur atom in the molecule so as to impart adhesive property to noble metal to the dental composition as the tooth substance adhesive composition. The monomer containing a sulfur atom in the molecule can be used regardless of the kind and number of unsaturated groups as well as the presence or absence of another functional group.

The component (u): sulfur atom-containing monomer containing a sulfur atom in the molecule and having a (meth)acryloyl group as a radical polymerizable unsaturated group may have the same constitution as the case that the dental composition is the dental adhesive composition.

The content of the component (u): sulfur atom-containing monomer having a sulfur atom in the molecule can be appropriately selected according to the application or purpose and usage of the dental composition as the tooth substance adhesive composition, and is preferably within a range of 0.01 to 10.0 wt. %. When the content of the component (u): sulfur atom-containing monomer having a sulfur atom in the molecule exceeds 10.0 wt. %, the polymerization of other monomers is prevented, which may adversely affect the adhesive property. In contrast, when the content of this monomer is less than 0.01 wt. %, it is impossible to obtain sufficient adhesion to noble metal.

The component (f): polymerization catalyst used in case that the dental composition of the present disclosure is the tooth substance adhesive composition is not particularly limited and a known radical generator can be used without any limitation.

The component (f): polymerization catalyst used in case that the dental composition of the present disclosure is the tooth substance adhesive composition is not particularly limited and a known radical generator can be used without any limitation.

The component (f): polymerization catalyst can have the same constitution as the case that the dental composition is the tooth substance adhesive primer, except for the constitution described below. In this case, a chemical polymerization catalyst, an organic peroxide, an amine compound, a sulfinate salt, a borate compound, and a barbituric acid may have the same constitution as the case that the dental composition is the tooth substance adhesive primer.

When the dental composition as the tooth substance adhesive composition is used alone, these chemical polymerization catalysts must be separately contained in at least two packaging-forms.

Among these chemical polymerization catalysts, sulfinates, barbiturates and organic peroxide-tertiary amine are preferably used alone or in combination, and organic peroxide-tertiary amine, organic peroxide-tertiary amine-barbiturates and organic peroxide-tertiary amine-sulfinates are more preferably used.

The content of chemical polymerization catalyst is preferably within a range of 0.1 to 15.0 wt. % and more preferably 0.1 to 10.0 wt. %.

The photopolymerization catalyst can have the same constitution as the case that the dental composition is the tooth substance adhesive primer, except for the constitution described below. In this case, the photosensitizer, the photopolymerization accelerator, and the oxycarboxylic acids can have the same constitution as the case that the dental composition is the tooth substance adhesive primer.

A packaging form and a preferable combination in case of using the photopolymerization catalyst may have the same constitution as the case that the dental composition is the dental adhesive composition.

The content of the component (w): photopolymerization catalyst is preferably within a range of 0.1 to 15.0 wt. %, more preferably from 0.1 to 10 wt. %, and most preferably from 0.1 to 8.0 wt. %.

A thermal polymerization catalyst, a sensitizing dye, a photoacid generator, a quaternary ammonium halide, a transition metal compound and the like may have the same constitution as the case that the dental composition is the tooth substance adhesive primer.

The component (l): water used in case that the dental composition of the present disclosure is the tooth substance adhesive composition can improve or enhance the adhesive property by a chelate bonding of an acidic group in the molecule of the acidic group-containing monomer which is ion dissociated and activated by the presence of water, with metal element such as calcium presence in tooth substance or metal element contained in other adherend.

Furthermore, when the component (l): water is compounded with an acid group-containing monomer and an acid reactive filler in a dental composition as a tooth substance adhesive composition, it is possible to improve the curability of the dental composition as the tooth substance adhesive composition with the polymerization catalyst by a chelate bonding (acid-base reaction) to an acid reactive element, which is a metal element, contained in the acid reactive filler in addition to improve or enhance the adhesive property to the above described tooth substance or the adherend by ion dissociation and activation of acidic group in the molecule by the presence of water.

Therefore water can be used without any limitation as long as it does not contain impurities which exert an adverse influence on polymerizability (curability) and adhesive property to the tooth substance or the adherend in the dental composition as the tooth substance adhesive composition. It is preferred to use distilled water or ion-exchange water.

The acidic group-containing monomer described above may be the same as or different from those already described, and there is no particular problem, and can be compounded in a dental composition as a tooth substance adhesive composition. Further, as long as it does not adversely affect the properties of the dental composition as a tooth substance adhesive composition, a polymer of an acidic group-containing monomer can be compounded in place of or as a part of the acidic group-containing monomer.

As the acid-reactive filler described above, any filler can be used without any limitation as long as the filler contains at least one kind or two or more kinds of acid-reactive elements which are metal elements belonging to Group I, Group II and Group III of the periodic table, and the content thereof is not particularly limited. Specific examples of the acid-reactive element contained in the acid-reactive filler include, but are not limited to, sodium, potassium, calcium, strontium, lanthanum, aluminum and the like. Furthermore, there is no particular limitation on the type and content of elements other than the acid-reactive element contained in the acid-reactive filler. That is, as the acid-reactive filler, oxide, hydroxide, sulfate, nitrate, phosphate, carbonate, silicate, fluoride, nitride, mineral, and glass may be used without any limitation as long as it contains the acid-reactive element. Specific examples of the acid reactive filler include aluminum silicate, aluminum oxide, a glass (including a glass by melting method, a glass produced by a vapor phase reaction, synthetic glass by sol-gel method and the like), strontium fluoride, calcium carbonate, mica, aluminum sulfate, calcium sulfate, barium sulfate, calcium phosphate, calcium hydroxide, strontium hydroxide, zeolite, hydroxyapatite, and aluminum nitride, but is not limited thereto.

There is no problem even if these acid-reactive fillers exhibit any of the properties in water such as insolubility, poor solubility, easy solubility and the shape of the acid-reactive filler is not particularly limited and arbitral particle shapes such as spherical, needle-like, plate-like, ground-like, and scaly-shapes may be used without any limitation. Further, the acid-reactive filler can be used alone or in combination of several kinds.

The content of the component (l): water can be appropriately selected according to the application or purpose and usage of the dental composition as the tooth substance adhesive composition, and is preferably within a range of 0.1 to 80.0 parts by weight based on 100 parts by weight of the total of the components of the dental composition as the tooth substance adhesive composition. When the content of water is more than 80.0 parts by weight, it is impossible to maintain the composition at a homogeneous state and separation arises, and thus an adverse influence is exerted on storage stability. In contrast, when the content of water is less than 0.1 parts by weight, it is impossible to obtain sufficient adhesive property to various adherends including tooth substances.

The component (p): organic solvent used in case that the dental composition of the present disclosure is the tooth substance adhesive composition plays a role, which is similar to that of a dissolution accelerator, of compatibilizing various monomers including the acidic group-containing monomer, a polymerization catalyst and another component, which are contained in the dental composition as the tooth substance adhesive composition, in an optional ratio, and also reduce the liquid viscosity of a dental composition as a tooth substance adhesive composition, and improve the operability such as dropping from a container or applying to a site to be adhered. Specific examples of the organic solvent compounded in the dental composition as the tooth substance adhesive composition include, but are not limited to, alcohols such as methanol, ethanol, 1-propanol, 2-propanol, and 1-butanol; ether compounds such as triethylene glycol monomethyl ether, triethylene glycol monomethyl ether, dipropylene glycol monomethyl ether, tetrahydrofuran, and dimethoxyethane; and ketone compounds such as acetone and methyl ethyl ketone. These organic solvents can also be used alone or in combination.

Among these organic solvents, methanol, ethanol, 1-propanol, 2-propanol and acetone which are water-soluble organic solvent are preferred, and acetone and ethanol are more preferred.

The content of the organic solvent can be appropriately selected according to the application or purpose and usage of the dental composition as the tooth substance adhesive composition, and is preferably within a range of 0.1 to 80.0 parts by weight based on 100 parts by weight of the total of the components of the dental composition as the tooth substance adhesive composition. When the content of the organic solvent is more than 80.0 parts by weight, adhesive property to tooth substances deteriorates. In contrast, when the content of the organic solvent is less than 0.1 parts by weight, it is impossible to maintain the composition at a homogeneous state and separation arises, and thus an adverse influence is exerted on storage stability.

It is possible to compound AEROSIL which is an ultrafine particle and produced by a gas phase method or a silica-zirconia oxide particle which is an ultrafine particle silica composite particle and produced in a solution of a sol-gel reaction or the like. Specific examples of AEROSIL include AEROSIL 200, AEROSIL OX50, AEROSIL R972, AERO- SIL R974, AEROSIL R8200, AEROSIL R711, AEROSIL DT4, Aluminum Oxide C, and Titanium Dioxide P25.

Also cohesive inorganic fillers obtained by intended cohesion of the filler containing the ultrafine particles may be used without causing any problems.

It is possible to optionally add components, for example, ultraviolet absorbers such as 2-hydroxy-4-methylbenzophenone; polymerization inhibitors such as hydroquinone, hydroquinone monomethyl ether, and 2,5-ditertiary butyl-4-methylphenol; discoloration inhibitors; antibacterial agent; coloration pigment; and another conventionally known additive; in the dental composition as the tooth substance adhesive composition.

The using method in case that the dental composition of the present disclosure is the tooth substance adhesive composition is not particularly limited, but it is preferable to be used singly to the tooth substance and it may be used in appropriate combination with other treating materials such as an etching material, a primer, a bonding material, a self-etching primer, a ceramic primer, a metal primer, and a precious metal primer to other adherends.

The packaging form in the case that the dental composition of the present disclosure is the tooth substance adhesive composition is not particularly limited, and may be appropriately selected according to the application from a single package or in a plurality of packages of two or more depending on the storage stability of tooth substance adhesive composition, the ratio of components to be compounded in the dental composition as a tooth substance adhesive composition, the type of the polymerization catalyst, the using method, purpose or the like.

In the component (i): acidic group-containing monomer used in case that the dental composition of the present disclosure is the tooth substance adhesive composition, the kind of acidic group contained in the acidic group-containing monomer is not particularly limited, and any acidic group-containing monomer having an acidic group can be used as long as the monomer does not correspond to the component (a). Other constitution of acidic group-containing monomer can be the same constitution as the case that the dental composition is the dental adhesive composition, except for the constitution described below. In this case, an acidic group-containing monomer having a phosphoric acid ester, an acidic group-containing monomer having a pyrophosphoric acid group, a carboxylic acid group-containing monomer, an acidic group-containing monomer having a phosphonic acid group, an acidic group-containing monomer having sulfonic acid group and an acidic group-containing monomer having thiophosphate group, and the preferable acidic group-containing monomer may have the same constitution as the case that the dental composition is the dental adhesive composition.

The compounding ratio of the acidic group-containing monomer may be appropriately changed depending on the purpose of use of the dental composition as the dental adhesive resin cement, but is prepared within a range of 1.0 to 50 parts by weight, preferably 2 to 30 parts by weight based on 100 parts by weight of the component (g): silane coupling agent.

As the component (u): sulfur atom-containing monomer used in case that the dental composition of the present disclosure is the dental adhesive resin cement, any monomers that are conventionally used as a dental sulfur atom-containing monomer can be used as long as the monomer does not correspond to the component (a) and the component (i). By containing the component (u): sulfur atom-containing monomer, it is possible to impart adhesive property to noble metals to the dental composition as the dental adhesive resin cement. Any monomer containing a sulfur atom in the molecule can be used regardless of the type and number of unsaturated groups and the presence or absence of other functional groups.

Specific examples of the sulfur atom-containing monomer having a sulfur atom having a (meth)acryloyl group as an saturated group include, but are not limited to, (meth)acrylate having a triazinethiol group, (meth)acrylate having a mercapto group, (meth)acrylate having a polysulfide group, (meth)acrylate having a thiophosphate group, (meth)acrylate having a cyclic disufide group, (meth)acrylate having a mercaptodithiazole group, (meth)acrylate having a thiouracil group, (meth)acrylate having a thiirane group, or the like. The monomer having a sulfur atom in the molecule may be used singly or a plural combinations. A particularly preferred compound is 10-methacryloxydecyl-6,8-dithioctanoate or 6-methacryloxyhexyl-6,8-dithioctanoate. The content of the component (u): sulfur atom-containing monomer having a sulfur atom in the molecule can be appropriately selected according to the application or purpose and usage of the dental composition as the dental adhesive resin cement, and is preferably within a range of 0.01 to 10.0 wt. %. When the content of the component (u): sulfur atom-containing monomer exceeds 10.0 wt. %, the polymerization of other monomers is prevented, which may adversely affect the adhesive property. In contrast, when the content of component (u): sulfur atom-containing monomer is less than 0.01 wt. %, it is impossible to obtain sufficient adhesive property to noble metal.

The component (g): silane coupling agent used in case that the dental composition of the present disclosure is the dental adhesive resin cement is not particularly limited, but it is preferable to use a silane coupling agent having a functional group capable of copolymerizing or forming a chemical bond with the monomer component in the dental composition as the dental adhesive resin cement and the adherend material, in order to obtain good adhesion to a ceramic material. Specifically, 3-methacryloxypropylmethyldimethoxysilane, 3-methacryloxypropylmethyldiethoxysilane, 3-methacryloxypropyltriethoxysilane, 3-acryloxypropyltrimethoxysilane, p-styryltrimethoxysilane, 3-mercaptopropyltrimethoxysilane, 3-mercaptopropylmethyldimethoxysilane, 3-glycidoxypropyltriethoxysilane, methyltrimethoxysilane, methyltriethoxysilane, methyltrichlorosilane, dimethyldichlorosilane, trimethylchlorosilane, hexamethyldisilazane, vinyltrimethoxysilane, vinyltriethoxysilane, vinyltrichlorosilane, vinyltriacetoxysilane, vinyltris(β-methoxyethoxy)silane, γ-methacryloyloxypropyltrimethoxysilane, γ-methacryloyloxypropyltris(β-methoxyethoxy)silane, γ-chloropropyltrimethoxysilane, γ-chloropropylmethyldimethoxysilane, γ-glycidoxypropyltrimethoxysilane, γ-glycidoxypropylmethyldiethoxysilane, β-(3,4-epoxycyclohexyl)ethyltrimethoxysilane, N-phenyl-γ-aminopropyltrimethoxysilane, hexamethyldisilazane, and the like are preferably used, and particularly preferably 3-methacryloxypropylmethyldimethoxysilane, 3-methacryloxypropyltrimethoxysilane, 3-methacryloxypropylmethyldiethoxysilane, 3-methacryloxypropyltriethoxysilane, and 3-acryloxypropyltrimethoxysilane are used. The mixing ratio of the (g): silane coupling agent may be appropriately used depending on the purpose of use of the dental composition, but is prepared within a range of 0.5 to 20 parts by weight, preferably 1 to 10 parts by weight based on 100 parts by weight of whole composition.

As the component (v): monomer other than the component (a), the component (i) and the component (u) used in case that the dental composition of the present disclosure is the dental adhesive resin cement, any monomer can be used without any limitation, as long as the monomer does not correspond to the component (a), the component (i) and the component (u).

In the present disclosure, the component (v): monomer other than the component (a), the component (i) and the component (u) is contained in a proportion of preferably within a range of 5 to 99.0 wt. %, preferably 10 to 90 wt. %.

Specific examples of the component (v): monomer other than the component (a), the component (i) and the component (u) include the hydrophilic monomer having a (meth) acryloyl group as the radical-polymerizable unsaturated group in case that the dental composition is the dental composite material composition and the hydrophobic monomer having monofunctional group, the hydrophobic monomer having aromatic bifunctional group, the hydrophobic monomer having aliphatic bifunctional group, the hydrophobic monomer having aliphatic trifunctional group, the hydrophobic monomer having aliphatic tetrafunctional group, and the urethane-based hydrophobic monomer in the case that the dental composition is the dental composite material composition. As long as it has a (meth)acrylate group, not only a monomer having a short main chain, but also an oligomer, a prepolymer and a polymer, each having a long main chain, can be used without any limitation.

The component (v): monomer other than the component (a), the component (i) and the component (u) is not limited thereto and can also be used alone or in combination.

Examples of the component (b): filler used in case that the dental composition of the present disclosure is the dental adhesive resin cement include a known dental filler such as an inorganic filler and/or an organic filler and/or an organic-inorganic composite filler, and these fillers can be used alone or in combination. The shape of these fillers may be any shape such as a spherical shape, needle shape, tabular shape, ground shape or scaly shape and is not particularly limited.

Specific examples of the inorganic filler include quartz, amorphous silica, aluminum silicate, aluminum oxide, various glasses which do not contain element having an X-ray blocking ability (including a glass by a melting method, a synthetic glass by a sol-gel method, and a glass produced by a gas phase reaction), calcium carbonate, talc, kaolin, clay, mica, aluminum sulfate, calcium sulfate, calcium phosphate, hydroxyapatite, silicon nitride, aluminum nitride, silicon carbide, boron carbide, calcium hydroxide. The average particle diameter of such an inorganic filler is not particularly limited, and is preferably within a range of 0.001 to 10 μm, more preferably within a range of 0.01 to 5 μm. Among the above described inorganic fillers, AEROSIL, as ultrafine particles, produced by a vapor phase method, or silica-zirconia oxide particles, as ultrafine silica composite particles, produced from the solution of the sol-gel reaction are effective for the present disclosure since they function as a thickener when mixed in the dental adhesive resin cement. Specific examples of AEROSIL include AEROSIL 200, AEROSIL OX50, AEROSIL R972, AEROSIL R974, AEROSIL R8200, AEROSIL R711, AEROSIL DT4, Aluminum oxide C, and Titanium dioxide P25.

Also cohesive inorganic fillers obtained by intended cohesion a filler containing the ultrafine particles may be used without causing any problems.

In this case, the organic filler can have the same constitution as that in case that the dental composition is the dental composite material composition. Preferably the average particle diameter of the organic filler is within a range of 1 to 100 μm. More preferably the average particle diameter is within a range of 3 to 50 μm and, further preferably within a range of 5 to 10 μm.

In this case, the organic-inorganic composite filler can have the same constitution as that in case that the dental composition is the dental composite material composition. The average particle diameter of the organic-inorganic composite filler is preferably within a range of 0.1 to 100 μm. More preferably, the average particle diameter is within a range of 0.1 to 50 μm and further preferably within a range of 2 to 30 μm.

For the purpose of improving the wettability with various monomers and water or other purposes, the surface of each filler such as an inorganic filler, an organic filler and an organic-inorganic composite filler is treated with a surface treatment agent and/or a surface treatment method and the surface treated filler can be used for a dental composition as an a dental adhesive resin cement.

The surface treatment agent and the surface treatment method that can be used for the surface treatment can be the same as the case that the dental composition is the dental composite material composition.

The filler surface may be subjected to a surface treatment by a special surface treatment agent and/or a special surface treatment method for the purpose of multi-functionalizing the filler, without any limitation.

A proportion of these filler in the dental composition as the dental adhesive resin cement may be optionally selected depending upon a material property required for a dental composition as the dental adhesive resin cement. In a dental composition as a dental adhesive resin cement, component (b): filler is preferably contained in a proportion of 1.0 to 90.0 wt. %, more preferably 2.5 to 70 wt. %.

As the component (d): polymerization initiator used in the present disclosure, a known compound generally used in a dental composition is used without any limitation. The polymerization initiator is generally classified into a thermal polymerization initiator and a photopolymerization initiator.

As the photopolymerization initiator, a photosensitizer that generates radicals by irradiating light can be used. Examples of the photosensitizer which initiates polymerization with ultraviolet ray include benzoin compounds such as benzoin, benzoin methyl ether, and benzoin ethyl ether, benzophenone compounds such as acetoin benzophenone, p-chlorobenzophenone, p-methoxybenzophenone, thioxanthone compounds such as thioxanthone, 2-chlorothioxanthone, 2-methylthioxanthone, 2-isopropylthioxanthone, 2-methoxythioxanthone, 2-hydroxythioxanthone, 2,4-diethylthioxanthone, 2,4-diisopropylthioxanthone. A photosensitizer which initiates polymerization with visible light is preferably used because it does not require ultraviolet light harmful to the human body. Examples of these include α-diketones such as benzyl, camphorquinone, α-naphthyl, acetonaphthene, p,p'-dimethoxybenzyl, p,p'-dichlorobenzylacetyl, pentanedione, 1,2-phenanthrenequinone, 1,4-phenanthrenequinone 3,4-phenanthrenequinone, 9,10-phenanthrenequinone, and naphthoquinone. Camphorquinone is preferably used.

Further, it is also preferable to use a combination of the photosensitizer and a photopolymerization accelerator. Particularly, when a tertiary amine is used as a photopolymerization accelerator, it is more preferable to use a compound in which a nitrogen atom is directly substituted in the aromatic group. As the photopolymerization accelerator, thertiary amines such as N,N-dimethylaniline, N,N-diethylaniline, N,N-di-n-butylaniline, N,N-dibenzylaniline, N,N-dimethyl-p-toluidine, N,N-dimethyl-m-toluidine, N,N-diethyl-p-toluidine, p-bromo-N,N-dimethylaniline, m-chloro-N,N-dimethylaniline, p-dimethylamino benzaldehyde, p-dimethylamino acetophenone, p-dimethylamino benzoic acid, p-dimethylamino benzoic acid ethyl ester, p-dimethylamino benzoic acid amino ester, N,N-dimethylanthranilic acid methyl ester, N,N-dihydroxyethyl aniline, N,N-dihydroxyethyl-p-toluidine, p-dimethylamino phenyl alcohol, p-dimethylaminostyrene, N,N-dimethyl-3,5-xylidine, 4-dimethylamino pyridine, N,N-dimethyl-α-naphthylamine, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethylmethacrylate, N,N-diethylaminoethylmethacrylate, and 2,2'-(n-butylimino) diethanol, barbituric acids such as 5-butylbarbituric acid and 1-benzyl-5-phenylbarbituric acid, and metal salts such as sodium salts and calcium salts thereof, tin compounds such as dibutyl-tin-diacetate, dibutyl-tin-dimaleate, dioctyl-tin-dimaleate, dioctyl-tin-dilaurate, dibutyl-tin-dilaurate, dioctyl-tin-diversate, dioctyl-tin-S,S'-bis-isooctyl mercaptoacetate and tetramethyl-1,3-diacetoxydistannoxane, and the like may be used. At least one kind of these photopolymerization accelerators can be selected and used, and two or more kinds can also be mixed and used. The addition amount of the above-mentioned initiator and accelerator can be appropriately determined.

In order to enhance photopolymerization promotion performances, it is effective to add, in addition to a tertiary amine, oxycarboxylic acids such as citric acid, malic acid, tartaric acid, glycolic acid, gluconic acid, α-oxyisobutyric acid, 2-hydroxypropanoic acid, 3-hydroxypropanoic acid, 3-hydroxybutanoic acid, 4-hydroxybutanoic acid and dimethylolpropionic acid.

Specific examples of the thermal polymerization initiator include an organic peroxide such as benzoyl peroxide, p-chlorobenzoyl peroxide, 2,4-dichlorobenzoyl peroxide, acetyl peroxide, lauroyl peroxide, tertiary butyl peroxide, cumene hydroperoxide, 2,5-dimethyl hexane-2,5-dihydroperoxide, methyl ethyl ketone peroxide and tertiary butyl peroxybenzoate, azo compounds such as azobisisobutyronitrile, azobisisobutyric acid methyl, azobiscyanovaleric and the like.

Further, the polymerization can be carried out at room temperature by using the combination of the organic peroxide and the amine compound. As such an amine compound, a secondary or tertiary amine having an amine group bonded to an aryl group is preferably used from the viewpoint of curing acceleration. For example, N,N-dimethyl-p-toluidine, N,N-dimethylaniline, N,N-β-hydroxyethyl-aniline, N,N-di(β-hydroxyethyl)-aniline, N,N-di(β-hydroxyethyl)-p-toluidine, N-methyl-aniline and N-methyl-p-toluidine are preferred.

It is also suitable to further combine a sulfinic acid salt or a borate with the combination of the organic peroxide and the amine compound. Examples of such sulfinic acid salts include sodium benzenesulfinate, lithium benzenesulfinate, and sodium p-toluenesulfinate. Examples of borates include sodium salts, lithium salts, potassium salts, magnesium salts, tetrabutylammonium salt and tetramethylammonium salt of trialkylphenylboron, and trialkyl(p-fluorophenyl)boron (wherein the alkyl group is n-butyl group, n-octyl group, n-dodecyl group, etc.). In addition, organoboron compounds such as tributylborane and tributylborane partial oxide, which generate radicals by reaction with oxygen or water, can also be used as an organometallic polymerization initiator.

Other components can be appropriately selected and added to the dental composition as the dental adhesive resin cement, and an additive component, that is, a polymerization inhibitor, a pigment, or the like may be appropriately compounded depending on the application.

Further, in the dental composition as a dental adhesive resin cement, various known additives may be optionally added as needed. Examples of such additives include a polymerization inhibitor, a colorant, a discoloration preventing agent, a fluorescent agent, an ultraviolet absorber and an antibacterial agent.

Examples of the polymerization inhibitor include hydroquinone, hydroquinone monomethyl ether, butylated hydroxytoluene and the like, which are suitable for stabilizing shelf life of the composition.

In the component (i): acidic group-containing monomer used in case that the dental composition of the present disclosure is the self-adhesive dental composite resin, the kind of acidic group contained in the acidic group-containing monomer is not particularly limited, and any acidic group-containing monomer having an acidic group can be used as long as the monomer does not correspond to the component (a). Other constitution of acidic group-containing monomer can be the same constitution as the case that the dental composition is the dental adhesive composition, except for the constitution described below. In this case, an acidic group-containing monomer having a phosphoric acid ester, an acidic group-containing monomer having a pyrophosphoric acid group, a carboxylic acid group-containing monomer, an acidic group-containing monomer having a phosphonic acid group, an acidic group-containing monomer having sulfonic acid group and an acidic group-containing monomer having thiophosphate group, and the preferable acidic group-containing monomer may have the same constitution as the case that the dental composition is the dental adhesive composition.

The content of the acidic group-containing monomer can be appropriately selected according to the application or purpose and usage of the dental composition as the self-adhesive dental composite resin, and is preferably within a range of 0.1 to 20.0 wt. %. When the content of the acidic group-containing monomer exceeds 20.0 wt. %, the polymerization of other monomers is prevented, which may adversely affect the adhesive property. In contrast, when the content of acidic group-containing monomer is less than 0.1 wt. %, the effect is not recognized in adhesion to tooth substance.

The dental composition of the present disclosure as the self-adhesive dental composite resin may contain the component (r): hydrophilic monomer. The component (r): hydrophilic monomer has the effect of enhancing adhesive property by improving permeability and wettability to an interface to be adhered by compounding in the dental composition as the self-adhesive composition. As the hydrophilic monomer, a monofunctional or polyfunctional monomer which exhibits hydrophilicity can be used without any limitation, regardless of the kind of a radical polymerizable unsaturated group, as long as the monomer does not correspond to the component (a) and the component (i). Such a hydrophilic monomer can have the same constitution as the case that the dental composition is a dental composite material composition, except for the constitution described below. In this case, a hydrophilic monomer having a (meth) acryloyl group as a radical polymerizable unsaturated group and a preferable hydrophilic monomer can have the same constitution as the case that the dental composition is the dental composite material composition.

The content of the hydrophilic monomer compounded in a dental composition as a self-adhesive dental composite resin is preferably 5 to 90 parts by weight, more preferably 10 to 60 parts by weight based on 100 parts by weight of the total weight of component (r): hydrophilic monomer and component (s): hydrophobic monomer contained in the dental composition as the self-adhesive dental composite resin. When the content deviates from the above range, wettability to the surface of the adherend to be adhered deteriorates and polymerizability is deteriorated, and thus adhesive property deteriorate.

The dental composition of the present disclosure as the self-adhesive dental composite resin may contain the component (s): hydrophobic monomer. As the component (s): hydrophobic monomer, a monofunctional or polyfunctional monomer which exhibits hydrophobicity can be used without any limitation, regardless of the kind of a radical polymerizable unsaturated group, as long as the monomer does not correspond to the component (a) and the component (i). Such a hydrophobic monomer can have the same constitution as the case that the dental composition is the dental composite material composition, except for the constitution described below. In this case, hydrophobic monomer having monofunctional group, hydrophobic monomer having aromatic bifunctional group, hydrophobic monomer having aliphatic bifunctional group, hydrophobic monomer having aliphatic trifunctional group, hydrophobic monomer having aliphatic tetrafunctional group, and the urethane-based hydrophobic monomer may have the same constitution as the case that the dental composition is the dental composite material composition.

The content of the hydrophobic monomer compounded in a dental composition as a self-adhesive dental composite resin is preferably 5 to 90 parts by weight, more preferably 40 to 90 parts by weight based on 100 parts by weight of the total weight of component (r): hydrophilic monomer and component (s): hydrophobic monomer contained in the dental composition as the self-adhesive dental composite resin. When the content deviates from the above range, wettability to the surface of the adherend to be adhered deteriorates and polymerizability is deteriorated, and thus adhesive property deteriorate.

It is also effective to use the component (u): sulfur atom-containing monomer containing a sulfur atom in the molecule so as to impart adhesive property to noble metal to the dental composition as the self-adhesive dental composite resin. The monomer containing a sulfur atom in the molecule can be used regardless of the kind and number of unsaturated groups as well as the presence or absence of another functional group.

The sulfur atom-containing monomer containing a sulfur atom in the molecule and having (meth) acryloyl group as unsaturated group may have the same constitution as the case that the dental composition is the dental adhesive resin cement, except for the constitution described below. The content of the component (u): sulfur atom-containing monomer can be appropriately selected according to the application or purpose and usage of the dental composition as the self-adhesive dental composite resin, and is preferably within a range of 0.01 to 10.0 wt. %. When the content of the sulfur atom-containing monomer containing a sulfur atom in the molecule exceeds 10.0 wt. %, the polymerization of other monomers is prevented, which may adversely affect the adhesive property. In contrast, when the content of this monomer is less than 0.01 wt. %, it is impossible to obtain sufficient adhesive property to noble metal.

The component (w): photopolymerization catalyst used in case that the dental composition of the present disclosure is the self-adhesive dental composite resin is not particularly limited and a known photopolymerization catalyst can be used without any limitation.

The photopolymerization catalyst can have the same constitution as the case that the dental composition is the tooth substance adhesive primer, except for the constitution described below. In this case, a photosensitizer, a photopolymerization accelerator, and an oxycarboxylic acid may have the same constitution as the case that the dental composition is the tooth substance adhesive primer.

A packaging form and a preferable combination in case of using the photopolymerization catalyst may have the same constitution as the case that the dental composition is the dental adhesive composition.

The content of the component (w): photopolymerization catalyst is preferably within a range of 0.1 to 15.0 wt. %, more preferably 0.1 to 10 wt. %, and most preferably 0.1 to 8 wt. %.

The constitution of the component (b): filler in case that the dental composition of the present disclosure is the self-adhesive dental composite resin can be the same constitution as the component (b): filler in case that the dental composition is the dental adhesive resin cement.

The constitution of the inorganic filler in this case can be the same constitution as the inorganic filler in case that the dental composition is the dental adhesive resin cement.

The average particle diameter of the organic filler in this case is preferably within a range of 1 to 1000 μm, more preferably 1 to 500 μm, further preferably 2 to 200 μm. Other constitution of the organic filler in this case can be the same constitution as the organic filler in case that the dental composition is the dental adhesive resin cement.

The average particle diameter of the organic-inorganic composite filler in this case is preferably within a range of 0.1 to 100 μm, more preferably 1 to 50 μm, further preferably 2 to 30 μm. The constitution of the organic-inorganic composite filler in this case can be the same constitution as the organic-inorganic composite filler in case that the dental composition is the dental adhesive resin cement.

For the purpose of improving the wettability with various monomers and water or other purposes, the surface of each filler such as an inorganic filler, an organic filler and an organic-inorganic composite filler is treated with a surface treatment agent and/or a surface treatment method and the surface treated filler can be used for a dental composition as a self-adhesive dental composite resin.

The surface treatment agent and the surface treatment method that can be used for the surface treatment can be the same as the case that the dental composition is the dental composite material composition.

The filler surface may be subjected to a surface treatment by a special surface treatment agent and/or a special surface treatment method for the purpose of multi-functionalizing the filler, without any limitation.

The content of these filler in the dental composition as the self-adhesive dental composite resin may be optionally selected depending upon a material property required for a dental composition as the self-adhesive dental composite resin, and may be, for example, 5 to 80 wt. %, preferably 50 to 80 wt. %.

In case that the dental composition of the present disclosure is the self-adhesive dental composite resin, it is preferable that the component (l): water and/or the component (p): organic solvent is not contained. When the component (l): water and/or the component (p): organic solvent is present in a dental composition as a self-adhesive dental composite resin, it inhibits the polymerization of the polymerizable component contained in the self-adhesive dental composite resin, resulting in a decrease in adhesive property and mechanical properties.

Further, in the dental composition as a self-adhesive dental composite resin, components such as additives in case that the dental composition is the dental composite material composition can be optionally added as needed.

The method of using the dental composition as the self-adhesive dental composite resin is not specifically limited, and the dental composition of the present disclosure may be used not only singly but also in appropriate combination with other treating materials such as an etching agent, a primer, a bonding material, a self-etching primer, a ceramic primer, a metal primer, and a precious metal primer, and bonding materials.

The packaging form in the case that the dental composition is the self-adhesive dental composite resin is not particularly limited, and may be appropriately selected according to the application from a single package or in a plurality of packages of two or more depending on the storage stability of the dental composition as a self-adhesive dental composite resin, the ratio of components to be compounded in the dental composition as a self-adhesive dental composite resin, the type of the polymerization catalyst, the using method, purpose or the like.

The dental composition as the self-adhesive dental composite resin may contain an X-ray contrasting glass filler. Specific examples of the element having an X-ray blocking ability that can be contained in the X-ray contrasting glass filler include chromium, iron and zinc in the fourth period of the periodic table, strontium, yttrium, zirconium, tin and tellurium in the fifth period of the periodic table, and barium, lanthanum, ytterbium, tantalum, tungsten, and bismuth in the sixth period of the periodic table but not limited to. Among these, examples of preferable the element having a preferable X-ray blocking ability contained in the X-ray contrast glass filler include strontium, barium, lanthanum, zirconium, titanium and the like.

The component (r): hydrophilic monomer used in case that the dental composition of the present disclosure is the adhesive composition has the effect of enhancing adhesive property by improving permeability and wettability to an interface to be adhered by compounding in the adhesive composition. As the hydrophilic monomer, a monofunctional or polyfunctional monomer which exhibits hydrophilicity can be used without any limitation, regardless of the kind of a radical polymerizable unsaturated group, as long as the monomer does not correspond to the component (a). Such a hydrophilic monomer can have the same constitution as the case that the dental composition is the dental composite material composition, except for the constitution described below. In this case, a hydrophilic monomer having a (meth)acryloyl group as a radical polymerizable unsaturated group and a preferable hydrophilic monomer can have the same constitution as the case that the dental composition is the dental composite material composition.

The content of the hydrophilic monomer compounded in a dental composition as an adhesive composition is preferably 5 to 90 parts by weight, more preferably 10 to 60 parts by weight based on 100 parts by weight of the total weight of component (r): hydrophilic monomer and the component (s): hydrophobic monomer contained in the dental composition as the adhesive composition. When the content deviates from the above range, wettability to the surface of the adherend to be adhered deteriorates and polymerizability is deteriorated, and thus adhesive property deteriorate.

In case that the dental composition of the present disclosure is the adhesive composition, as the component (s): hydrophobic monomer, a monofunctional or polyfunctional monomer which exhibits hydrophobicity can be used without any limitation, regardless of the kind of a radical polymerizable unsaturated group, as long as the monomer does not correspond to the component (a). Such a hydrophobic monomer can have the same constitution as the case that the dental composition is the dental composite material composition, except for the constitution described below. In this case, hydrophobic monomer having monofunctional group, hydrophobic monomer having aromatic bifunctional group, hydrophobic monomer having aliphatic bifunctional group, hydrophobic monomer having aliphatic trifunctional group, hydrophobic monomer having aliphatic tetrafunctional group, and the urethane-based hydrophobic monomer may have the same constitution as the case that the dental composition is the dental composite material composition.

The content of the hydrophobic monomer compounded in a dental composition as an adhesive composition is preferably 10 to 95 parts by weight, more preferably 40 to 90 parts by weight based on 100 parts by weight of the total weight of component (r): hydrophilic monomer and component (s): hydrophobic monomer contained in the dental composition as the adhesive composition. When the content deviates from the above range, wettability to the surface of the adherend to be adhered deteriorates and polymerizability is deteriorated, and thus adhesive property deteriorate.

In case that the dental composition of the present disclosure is the adhesive composition, the total amount of the component (r): hydrophilic monomer and the component (s): hydrophobic monomer is in a proportion of 30.0 to 99.5 wt. %, preferably 50.0 to 97.5 wt. %.

The component (f): polymerization catalyst used in case that the dental composition of the present disclosure is the adhesive composition is not particularly limited and a known radical generator can be used without any limitation. The component (f): polymerization catalyst may have the same constitution as the case that the dental composition is the dental adhesive composition, except for the constitution described below. In this case, a chemical polymerization catalyst, an organic peroxide, an amine compound, a sulfinate salt, a borate compound, and a barbituric acid may have the same constitution as the case that the dental composition is the dental adhesive composition.

When the dental composition as the adhesive composition is used alone, these chemical polymerization catalysts must be separately contained in at least two packaging-forms. When the dental composition as the adhesive composition is used together with another treatment material, both the dental composition as the adhesive composition and another treatment material can contain the chemical polymerization catalyst so as to initiate chemical polymerization by bringing the dental composition as the treatment material into contact with another treatment material.

Among chemical polymerization catalysts, sulfinates, barbiturates and organic peroxide-tertiary amine are preferably used alone or in combination, and organic peroxide-tertiary amine, organic peroxide-tertiary amine-barbiturates and organic peroxide-tertiary amine-sulfinates are more preferably used.

The content of chemical polymerization catalyst is preferably within a range of 0.1 to 15.0 wt. % and more preferably 0.1 to 10.0 wt. %.

The photopolymerization catalyst may have the same constitution as the case that the dental composition is the dental adhesive composition. In this case, a photosensitizer, a photopolymerization accelerator, and an oxycarboxylic acid may have the same constitution as the case that the dental composition is the dental adhesive composition.

A packaging form, preferable combination and the content in case of using the photopolymerization catalyst may have the same constitution as the case that the dental composition is the dental adhesive composition.

As the thermal polymerization catalyst capable of initiating polymerization by heating or warming other than the above organic peroxide, azo compounds such as azobisisobutyronitrile, methyl azobisisobutyrate and azobiscyanovaleric acid are preferably used, but are not limited to. These thermal polymerization catalysts can also be used alone or in combination.

According to the application, coumarin-based, cyanine-based and thiazine-based sensitizing dyes; photo acid generators which are irradiated with light to generate Brønsted acid or Lewis acids, such as a halomethyl group substituted-s-triazine derivative, diphenyliodonium salt compound, etc.; quaternary ammonium halides; and transition metal compounds can be appropriately used.

The component (g): silane coupling agent used in case that the dental composition of the present disclosure is the adhesive composition is not particularly limited, but may have the same constitution as the silane coupling agent in the case that the dental composition is the resin cement. The content of silane coupling agent is preferably 0.1 to 15 wt. %, and more preferably 1 to 8 wt. %.

Among the component (q): acid anhydride and/or weakly acidic compound used in case that the dental composition of the present disclosure is the adhesive composition, the weakly acidic compound may have the same constitution as the weakly acidic compound in the case that the dental composition is the dental primer.

Among the component (q): acid anhydride and/or weakly acidic compound used in case that the dental composition of the present disclosure is the adhesive composition, the acid anhydride may have the same constitution as the acid anhydride in the case that the dental composition is the dental primer.

Preferable acid anhydride is an acid anhydride having pH of 2 or more, and is a carboxylic acid based-compound, and more preferable acid anhydride consists of a carboxylic acid based-compound. As the carboxylic acid based-compound, compounds of tartaric acid, malic acid, citric acid, maleic acid, itaconic acid and aconitic acid are preferable. In particular, citric acid, maleic acid, itaconic acid and anhydride thereof are more preferable. It is preferable that the acid anhydride contains an anhydride of a carboxylic acid, a sulfonic acid, a nitric acid and/or a phosphoric acid.

The content of the component (q): acid anhydride and/or weakly acidic compound is preferably 0.1 to 5 wt. %, and more preferably 0.1 to 2 wt. %.

When the component (l): water and/or the component (p): organic solvent is present in a dental composition as an adhesive composition, it inhibits the polymerization of the polymerizable component contained in the adhesive composition, resulting in a decrease in adhesive property and mechanical properties. Therefore, in case that the dental composition of the present disclosure is the adhesive composition, particularly when an acidic group-containing monomer is not contained, it is preferable that the component (l): water and/or the component (p): organic solvent are not contained. When the dental composition as the adhesive composition contains the component (l): water and/or the component (p): organic solvent, it is necessary to sufficiently dry with a gun or the like to volatilize water and organic solvent before polymerization and/or in polymerization process, after applying the dental composition as the adhesive composition to the site to be restored.

The dental composition of the present disclosure as the adhesive composition may contain the component (b): filler. In this case, the constitution of the component (f): filler can be the same constitution as the component (b): filler in case that the dental composition is the dental adhesive resin cement, except for the constitution described below.

The constitution of the inorganic filler in this case can be the same constitution as the inorganic filler in case that the dental composition is the dental adhesive resin cement.

The average particle diameter of the organic filler in this case is preferably within a range of 0.1 to 200 μm, more preferably 0.5 to 150 μm, further preferably 1 to 100 μm. Other constitution of the organic filler in this case can be the same constitution as the organic filler in case that the dental composition is the dental adhesive resin cement.

The average particle diameter of the organic-inorganic composite filler in this case is preferably within a range of 0.1 to 100 μm, more preferably 1 to 50 μm, further preferably 0.2 to 30 μm. Other constitution of the organic-inorganic composite filler in this case can be the same constitution as the organic-inorganic composite filler in case that the dental composition is the dental adhesive resin cement.

For the purpose of improving the wettability with various monomers and water or other purposes, the surface of each filler such as an inorganic filler, an organic filler and an organic-inorganic composite filler is treated with a surface treatment agent and/or a surface treatment method and the surface treated filler can be used for a dental composition as an adhesive composition.

The surface treatment agent and the surface treatment method that can be used for the surface treatment can be the same as the case that the dental composition is the dental composite material composition.

The filler surface may be subjected to a surface treatment by a special surface treatment agent and/or a special surface treatment method for the purpose of multi-functionalizing the filler, without any limitation.

A proportion of these filler in the dental composition as the adhesive composition may be optionally selected depending upon a material property required for a dental composition as the adhesive composition.

Further, in the dental composition as an adhesive composition, components such as additives in case that the dental composition is the dental composite material composition can be optionally added as needed.

The method of using the dental composition as the dental adhesive composition is not specifically limited, and the dental composition of the present disclosure may be used not only singly but also in appropriate combination with other treating materials such as an etching material, a primer, a bonding material, a self-etching primer, a ceramic primer, a metal primer, and a precious metal primer, bonding materials.

The packaging form in case that the dental composition of the present disclosure is an adhesive composition is not particularly limited, and may be appropriately selected according to the application from a single package or in a plurality of packages of two or more depending on the storage stability of the dental composition as the adhesive composition, the ratio of components to be compounded in the dental composition as the adhesive composition, the type of the polymerization catalyst, the using method, purpose or the like.

The dental composition as the adhesive composition may include an X-ray contrasting glass filler. The X-ray contrasting glass filler contained in the dental composition as the adhesive composition may have the same constitution as the X-ray contrasting glass filler in the case that the dental composition is the self-adhesive dental composite resin.

EXAMPLES

The present disclosure is described in more detail and specifically with reference to Examples. However, the present disclosure is not limited to Examples.

[1. Dental Composite Material Composition]

A characteristic confirmation test method in case that the dental composition is the dental composite material composition is described below.

(Curability Test)

A dental composite material composition was filled in a plaster mold with a hole having a thickness of 2 mm and diameter of 15 mm and was immersed in water. The dental composite material composition was polymerized and cured by irradiating a surface of the filled dental composite material composition with light for 180 seconds using a dental light irradiator (SOLIDILIGHT II, manufactured by SHOFU INC.). The Vickers hardness (kgf/mm$^2$) of the cured products was measured by the following measuring method.

The pressed glass plate was removed. The Vickers hardness on the surface of the cured product (composite material), which was pressed into contact with the glass plate, was measured using a micro hardness tester (made by Akashi Seisakusyo K.K., merchandise code:"MVK-E") in 200 g load for 10 seconds. Measurement was performed 3 times in different positions and the average value of the 3 measurement times was defined as the Vickers hardness of the cured products.

(Adhesion Test Method)

After slaughter, a narrow piece of a cow tooth was prepared by extracting a permanent mandibular central incisor, freezing the incisor within 24 hours and unfreezing the incisor, and removing the root portion and cutting away the crown portion. The narrow piece of the cow tooth was embedded in an epoxy resin. The embedded cow tooth was sanded using #600 waterproof abrasive paper while pouring water to expose an enamel or a dentin, and then washed with water.

A double-sided tape with a hole having a diameter of 4 mm was affixed to the exposed enamel or dentin to prescribe an adhesion surface. Shofu Beauty Bond Universal was sufficiently applied to the entire prescribed adhesion surface to create an adhesive material surface. Then, after leaving it for 10 seconds, air-drying with low pressure was performed for about 3 seconds, and then the air was strengthened to be sufficiently dried. Then, the wet condition in the oral cavity was reproduced by immersing in water at 37° C. for 15 minutes. A plastic mold (inside diameter: 4 mm, height: 4 mm) was fixed to the prescribed adhesive material surface, and the dental composite material composition was injected into the inside of a mold, and irradiated with light for 30 seconds using a photo polymerization irradiator (Grip Light II manufactured by SHOFU INC.) to be cured. After curing, the mold was removed to prepare an adhesion test specimen.

The adhesion test specimen was immersed in distilled water at 37° C. for 24 hours. After that, a tooth substance adhesion test was performed for shear bond strength, using an Instron universal testing machine (Instron 5567 manufactured by Instron) at a crosshead speed of 1 mm/min. The number of samples was 6, and the average value was calculated.

[Component and Abbreviation]

The abbreviations of the components used in the examples are described below.

<Other Polymerizable Monomer>
Bis-GMA: 2,2-bis(4-(3-(meth)acryloyloxy-2-hydroxypropoxy)phenyl)propane
UDMA: di(methacryloxyethyl)trimethylhexamethylenediurethan
TEGDM: triethyleneglycol-dimethacrylate
HEMA: 2-hydroxyethyl methacrylate
<Polymerizable Monomer Having Phosphate Ester Group>
2-MEP: 2-(methacryloxy)ethyl phosphate
Bis-MEP: bis[2-(methacryloyloxy)-ethyl]phosphate
6-MHPA: 6-(methacryloxy)hexyl phosphonoacetate
<Polymerizable Monomer Having Dibasic Acid Carboxyl Group>
4-AET: 4-Acryloxyethyltrimellitic acid
4-MET: 4-Methacryloxyethyltrimellitic acid
<Monomer Containing Acrylamide Group>
FAM-401 (manufactured by FUJIFILM Corporation)
FAM-201 (manufactured by FUJIFILM Corporation)
<Filler>
ASG filler: Aluminosilicate glass filler (average particle diameter of 5 μm)
<Ultrafine Particle Filler>
R-972
<Polymerization Accelerator>
BBA.Na: a sodium salt of 5-n-butylbarbituric acid
EB: p-N,N-Ethyl-dimethylaminobenzoate
OT: Dioctyltin dilaurate
<Polymerization Initiator>
CQ: Camphorquinone
<Polymerization Inhibitor>
BHT: Butylated hydroxytoluene The preparation of the composite material is as follows.

(Preparing Mixed Polymerizable Monomer)

The polymerizable monomer and the polymerization initiator shown in Table 2 were mixed by mixer (Aikosha Inc.: BM) which uses a blade for mixing or a tumbler mixer (Seiwa Giken Inc.: TM).

(Silane Treatment Method)

Silane Treatment Conditioning Products

Silane treatment liquid a: 3% of γ-methacryloyloxypropyltrimethoxysilane as silane coupling agent, 77% of ethyl alcohol, and 20% of water.

Silane treatment liquid b: 30% of γ-methacryloyloxypropyltrimethoxysilane as silane coupling agent, 69% of ethyl alcohol, and 1% of water.

The above silane treatment liquid was prepared and the filler was treated with the silane treatment liquid a or the silane treatment liquid b, which were sprayed and mixed in a treatment container by stirring. After mixing, the silane-treated filler was aged in a hot air drier, moored, and then cooled to obtain a silane-treated filler aggregate. The obtained heat-treated product was charged into a Henschel mixer and crushed to prepare silane-treated fillers a and b of which surfaces were coated with poly(organo)siloxane.

(Preparing Composite Material)

The mixed polymerizable monomer, the filler, and the ultrafine particle filler were mixed with a kneader (ND, manufactured by Inoue Seisakusho) or a planetary mixer (PM, manufactured by Inoue Seisakusho) in the predetermined amount shown in Table 3.

(Evaluating Composite Material)

A hardening test and an adhesive bending strength test were performed with respect to the composite material.

TABLE 2

|  |  |  | Sample 1-1 | Sample 1-2 | Sample 1-3 | Sample 1-4 | Sample 1-5 | Sample 1-6 | Sample 1-7 | Sample 1-8 | Sample 1-9 |
|---|---|---|---|---|---|---|---|---|---|---|---|
| Mixed polymerizable monomer | Polymerizable monomer | Bis-GMA (pts. wt) | 30 | 37 | 34.9 | 35.8 | 34 | 24.5 | 34.7 | 31 | 34.5 |
|  |  | UDMA (pts. wt) | 27 | 20 | 28 | 26 | 26 | 25 | 20 | 16.5 | 25 |
|  |  | TEGDM (pts. wt) | 10 | 10 | 10 | 10 | 10 | 10 | 7.8 | 8.5 | 10 |
|  |  | HEMA (pts. wt) | 26 | 26 | 26 | 26 | 25 | 25.5 | 25.5 | 25 | 25.5 |
|  | Phosphate ester-based polymerizable monomer | 2-MEP (pts. wt) | 3 | 0 |  |  |  |  |  |  |  |
|  |  | Bis-MEP (pts. wt) | 0 | 2 |  |  |  |  |  |  |  |
|  |  | 6-MHPA (pts. wt) | 1 | 2 |  |  |  |  |  |  |  |
|  | Carboxyl group-based polymerizable monomer | 4AET (pts. wt) | 3 | 0 |  |  |  |  |  |  |  |
|  |  | 4-MET (pts. wt) | 0 | 3 |  |  |  |  |  |  |  |
|  | Acrylamide group-containing monomer | FAM-401 (pts. wt) |  |  | 1.1 | 2.2 | 5 | 15 | 10 | 19 |  |
|  |  | FAM-201 (pts. wt) |  |  |  |  |  |  | 2 |  | 5 |
|  | Polymerization accelerator | BBA·Na (pts. wt) | 1 | 0 | 1 | 1 | 0 | 0 | 0 | 0 | 0 |
|  |  | EB (pts. wt) | 0 | 1 | 0 | 0 | 1 | 1 | 1 | 1 | 1 |
|  |  | OT (pts. wt) | 1 | 1 | 1 | 1 | 1 | 1 | 1 | 1 | 1 |
|  | Polymerization initiator | CQ (pts. wt) | 0.3 | 0.3 | 0.3 | 0.3 | 0.3 | 0.3 | 0.3 | 0.3 | 0.3 |
|  | Polymerization Initiator | BHT (pts. wt) | 0.1 | 0.1 | 0.1 | 0.1 | 0.1 | 0.1 | 0.1 | 0.1 | 0.1 |

TABLE 3

Composition of composite materials and evaluation results

|  |  |  | Example 1-1 | Example 1-2 | Example 1-3 | Example 1-4 | Example 1-5 | Example 1-6 | Comparative Example 1-1 | Comparative Example 1-2 | Comparative Example 1-3 |
|---|---|---|---|---|---|---|---|---|---|---|---|
| Composite material | Polymerizable monomer | Sample type | 1-3 | 1-4 | 1-5 | 1-6 | 1-7 | 1-8 | 1-1 | 1-2 | 1-9 |
|  |  | (g) | 2000 | 2000 | 2000 | 2000 | 2000 | 2000 | 2000 | 2000 | 2000 |
|  | Filler | ASG filler (g) | 1400 | 1400 | 1400 | 1400 | 1400 | 1400 | 1400 | 1400 | 1400 |
|  |  | Silane treatment liquid | a | b | a | b | a | b | a | b | b |
|  | Ultrafine particle filler | R-972 (g) | 60 | 60 | 60 | 60 | 60 | 60 | 60 | 60 | 60 |
| Test result | Hardening test | (kgf/m²) | 46.3 | 53.4 | 54.4 | 46.1 | 52.9 | 45.9 | 22.4 | 21.3 | 26.5 |
|  | Adhesive test | Enamel (MPa) | 13.2 | 16.2 | 16.9 | 13.5 | 16.9 | 10.8 | 10.2 | 10.5 | 7.5 |
|  |  | Dentin (MPa) | 13.5 | 17.3 | 17.8 | 14 | 17.5 | 11.2 | 8.8 | 8.3 | 8.2 |

As shown in Table 3, in Examples 1-1 to 1-6, excellent results were obtained in both the curability test and the adhesion test, and it was confirmed that sufficient curability was exhibited even in an excessive moisture condition such as in the oral cavity and it can be used clinically. On the other hand, in Comparative Examples 1-1 to 1-3, sufficient results were not obtained in both the curability test and the adhesion test, and practicability was not recognized in the state of excessive moisture such as in the oral cavity.

[2. Dental Resin Cement]

A characteristic confirmation test method in case that the dental composition is the dental resin cement is described below.

(i) Measurement of Adhesive Strength for Enamel and Dentin

A freshly removed bovine anterior tooth was used instead of a human tooth, and it was embedded in an epoxy resin after removing a part of dental root. A labial surface of the tooth was polished with a water-resistant sandpaper under flushing water to expose an enamel and a dentin. The tooth was polished with SiC No. 600, washed with water and preserved in water for 1 week. On the other hand, an adhesive surface of a stainless rod (diameter of 4.15 mm), which is a jig for an adhesive test, was sandblast-treated with alumina having a particle diameter of about 50 μm, washed with water. A primer for metal materials "METAL LINK" (SHOFU INC.) was applied to the surface of the stainless rod and it was allowed to dry for 10 seconds. First and second pastes of the resin cement which had been separately filled in double syringes (SULZUR MIXPAC) at an equal amount were kneaded and extruded by passing through an accompanied static mixer. An extruded paste was inserted between the tooth and the stainless rod and they were adhered by applying a 200 g load. An excess paste was removed with a microbrush, light was irradiated along a cement line for 10 seconds. For light irradiation, "Grip Light II" (SHOFU INC.) was used. Ten minutes after light irradiation was finished, the load was removed. The same adhesive test samples (n=6) were immersed in distilled water at 37° C. for 24 hours and then a shear bond strength thereof for the tooth was measured with an Instron type universal tester (Instron 5567, Instron) at 1 mm/min. of a cross head speed.

(ii) Measurement of Adhesive Strength for Porcelain

One side plane of a fired product of dental porcelain "Vintage Hallow" (SHOFU INC.)(φ 11 mm×8.5 mm) was polished with SiC No. 600, washed with water and preserved in water for 1 week. Then the plane was sandblast-treated with alumina having a particle diameter of about 50 μm (0.1-0.2 MPa), washed with water and air-dried. On the other hand, an adhesive surface of a stainless rod (diameter of 4.15 mm), which is a jig for an adhesive test, was sandblast-treated with alumina having a particle diameter of about 50 µm, washed with water. A primer for metal materials "METAL LINK" (SHOFU INC.) was applied to the surface of the stainless rod and it was allowed to dry for 10 seconds and used for measurement. The stainless rod, the apparatus for an adhesive test (diameter of 4.55 mm), was used to measure a tensile bond strength for porcelain according to a similar method as that used in (i).

(iii) Measurement of Adhesive Strength for Zirconia

One side plane of flat zirconia (15 mm×15 mm×1.8 mm)(Japan Fine Ceramics Co., Ltd.) was polished with SiC No. 600, washed with water and preserved in water for 1 week. Then the plane was sandblast-treated with alumina having a particle diameter of about 50 µm (0.2-0.3 MPa), washed with water. A tensile bond strength for zirconia was measured according to the same method as that used in (ii).

(iv) Measurement of Adhesive Strength for Composite Resin

A metal frame having an inner diameter of 15 mm and a height of 2 mm was placed on a cover glass and a paste of a composite resin "Ceramage" (SHOFU INC.) was filled therein. The paste of a composite resin was pressed and adhered from both of upper and lower planes through the cover glass, and then either of cover glass planes was upturned and light was irradiated thereto with "Twin Cure" (SHOFU INC.) for 3 minutes. A bottom plane was sandblast-treated (0.1-0.2 MPa), washed with water and preserved in water for 1 week. A tensile bond strength for the composite resin was measured according to the same method as that used in (ii).

(v) Measurement of Adhesive Strength for Gold Alloys

One side plane of a flat gold alloy "Super Gold 4" (15 mm×15 mm×2.1 mm)(SHOFU INC.) was polished with SiC No. 600, washed with water. Then the plane was sandblast-treated with alumina having a particle diameter of about 50 µm (0.4 to 0.5 MPa), washed with water and preserved in water for 1 week. A tensile bond strength for the gold alloy was measured according to a similar method as that used in (ii).

[Components and Abbreviations]

The abbreviations of the components used in the Examples are as follows.
[Radical Polymerizable Monomer]
UDMA: Di-2-methacryloyloxyethyl-2,2,4-trimethylhexamethylene dicarbamate
3G: Triethyleneglycol dimethacrylate
Bis-GMA: 2,2'-Bis[4-(3-(meth)acryloyloxy-2-hydroxypropoxy)phenyl]propane
2-HEMA: 2-hydroxyethyl methacrylate
[Acidic Group-Containing Monomer]
2-MEP: 2-(Methacryloxy)ethyl phosphate
4-AET: 4-Acryloxyethyltrimellitic acid
4-MET: 4-Methacryloxyethyltrimellitic acid
[Filler]
FASG filler: Fluoroaluminosilicate glass filler, average particle diameter of 1.8 µm, filler silanated with 8% of γ-methacryloyloxypropyltrimethoxy silane
R-711: Ultrafine particle silicafiller
[Silane Coupling Agent]
γ-methacryloyloxypropyl trimethoxysilane
[Polymerization Accelerator]
BBA.Na: Sodium 5-n-butylbarbiturate
DEPT: N,N-di(2hydroxyethyl)-p-toluidine
[Polymerization Initiator]
BPO: Benzoyl peroxide
CQ: Camphorquinone
[Shelf Life Stabilizer]
BHT: Butylated hydroxytoluene
[Monomer Containing (Meth)Acrylamide Group]
FAM-401 (manufactured by FUJIFILM Corporation)
FAM-201 (manufactured by FUJIFILM Corporation)

(1) Preparation of Resin Cement

Two-paste type resin cements of Examples 2-1 to 2-5 and Comparative Examples 2-1 to 2-3 consisting of first and second pastes were prepared on a basis of a composition of Table 4.

TABLE 4

| Paste | Component | Example 2-1 | Example 2-2 | Example 2-3 | Example 2-4 | Example 2-5 | Comparative Example 2-1 | Comparative Example 2-2 | Comparative Example 2-3 |
|---|---|---|---|---|---|---|---|---|---|
| First paste | UDMA | 10.2 | 10.2 | 10.2 | 10.2 | 10.2 | 10.2 | 10.2 | 10.2 |
| | 3G | 4.6 | 4.6 | 4.6 | 4.6 | 4.6 | 4.6 | 4.6 | 4.6 |
| | FAM-401 | 0.3 | 0.6 | 2.9 | 4.4 | 5.6 | | | |
| | FAM-201 | | | | | | | | 5 |
| | γ-methacryloyloxypropyl trimethoxysilane | 2 | 2 | 2 | 2 | 2 | 2 | 2 | 2 |
| | FASG filler | 31.8 | 31.8 | 31.8 | 31.8 | 31.8 | 31.8 | 31.8 | 31.8 |
| | R-711 | 1.1 | 1.1 | 1.1 | 1.1 | 1.1 | 1.1 | 1.1 | 1.1 |
| | BBA · Na | 0.2 | 0.2 | 0.2 | 0.2 | 0.2 | 0.2 | 0.2 | 0.2 |
| | DEPT | 0.1 | 0.1 | 0.1 | 0.1 | 0.1 | 0.1 | 0.1 | 0.1 |
| | BHT | 0.01 | 0.01 | 0.01 | 0.01 | 0.01 | 0.01 | 0.01 | 0.01 |
| Second paste | Bis-GMA | 8.8 | 8.8 | 8.8 | 8.8 | 8.8 | 8.8 | 8.8 | 8.8 |
| | 3G | 3.7 | 3.7 | 3.7 | 3.7 | 3.7 | 3.7 | 3.7 | 3.7 |
| | 2-HEMA | 2.4 | 2.4 | 2.4 | 2.4 | 2.4 | 2.4 | 2.4 | 2.4 |
| | 2-MEP | 1.2 | 1.2 | 1.2 | 1.2 | 1.2 | 1.2 | 1.2 | 1.2 |
| | 4-AET | 1.2 | 1.2 | 1.2 | 1.2 | 1.2 | 1.2 | | |
| | 4-MET | | | | | | | 1.2 | 1.2 |
| | FASG filler | 31 | 31 | 31 | 31 | 31 | 31 | 31 | 31 |
| | R-711 | 1.5 | 1.5 | 1.5 | 1.5 | 1.5 | 1.5 | 1.5 | 1.5 |
| | BPO | 0.1 | 0.1 | 0.1 | 0.1 | 0.1 | 0.1 | 0.1 | 0.1 |
| | CQ | 0.1 | 0.1 | 0.1 | 0.1 | 0.1 | 0.1 | 0.1 | 0.1 |
| | BHT | 0.03 | 0.03 | 0.03 | 0.03 | 0.03 | 0.03 | 0.03 | 0.03 |

TABLE 4-continued

| Paste | Component | Example 2-1 | Example 2-2 | Example 2-3 | Example 2-4 | Example 2-5 | Comparative Example 2-1 | Comparative Example 2-2 | Comparative Example 2-3 |
|---|---|---|---|---|---|---|---|---|---|
| shear bond strength (Mpa) | Enamel | 20.8 | 24.7 | 23.8 | 20.9 | 18.6 | 7.2 | 7.4 | 8.5 |
| | Dentin | 18.8 | 22.1 | 20.5 | 18.7 | 16.8 | 6.3 | 6.6 | 7.9 |
| Tensile bond strength (MPpa) | Zirconia | 16.8 | 23.5 | 24.7 | 16.5 | 11.1 | 6.1 | 6.3 | 7.8 |
| | Porcelain | 19.4 | 22.2 | 21.5 | 21.7 | 13.4 | 6.8 | 6.2 | 7.6 |
| | Composite resin | 18.2 | 21.5 | 22.2 | 18.8 | 11.1 | 6.9 | 6.2 | 7.6 |
| | Gold alloy | 16.9 | 20.1 | 20.9 | 17.4 | 16.3 | 7.2 | 7.5 | 7.7 |

(2) Evaluation of Properties of Resin Cements
[Adhesive Strength]

The resin cement was measured for a shear bond strength to the tooth test specimen which was not air-dried (an enamel and a dentin) and a tensile bond strength to each test specimen of zirconia, porcelain, a composite resin and a gold alloy. The measurement results are shown in Table 4.

As shown in Table 4, in Examples 2-1 to 2-5, excellent results were obtained in both of all shear bond test and tensile bond strength test, and it was confirmed that sufficient curability was exhibited even in an excessive moisture condition such as in the oral cavity or on an adherend that has absorbed water and it can be used clinically. On the other hand, in Comparative Examples 2-1 to 2-3, sufficient results were not obtained in any test, practicability was not recognized in the state of excessive moisture such as in the oral cavity and on an adherend that has absorbed water.

[3. Denture Restorative Material]

A characteristic confirmation test method in case that the dental composition is the denture restorative material is described below.

(Adhesion Bending Strength Test Method)
[Object of Evaluation]

To evaluate adhesion bending strength to general-purpose dental acrylic resin.

[Evaluation Method]

A test piece (10×2×2 mm: cuboid) was prepared from a general-purpose dental acrylic resin (PROVINICE: manufactured by SHOFU INC.) in a plaster mold in the presence of water, and immersed in water at 37° C. for 7 days. Such test specimens were secured with a clearance of 5 mm disposed there between. Next, a powder material and a liquid material prepared according to compounding table were kneaded in a predetermined ratio to prepare a kneaded product of a denture restorative material. The clearance of 5 mm disposed between the test pieces was filled using a brush. After filling, the resultant was left to stand for 1 hour, and burr and the like were removed to provide a test specimen (25×2×2 mm: cuboid type). The test specimen was immersed in water at 37° C. for 24 hours, and thereafter subjected to the adhesion bending strength test.

The adhesion bending strength test was conducted at a distance between supporting points of 20 mm and at a crosshead speed of 1 mm/min using an Instron universal testing machine (Instron 5567 manufactured by Instron). Herein, the test was conducted for ten test specimens, and evaluation was made by the average value for the ten test specimens.

(Filling Test Method)
Object of evaluation: To evaluate wettability with and fillability to wet general-purpose dental acrylic resin.
Evaluation method: The filling test was conducted at the same time as the timing where "the clearance of 5 mm disposed between the test pieces was filled therewith" in the adhesion bending strength test method. The rating criteria are as follows.

A: The clearance between the test pieces could be filled with the kneaded product without any space, and the brush was favorably released.
B: While bubbles were slightly generated at the corner of the clearance between the test pieces, the brush was favorably released.
C: Bubbles were generated at the corner of the clearance between the test pieces, and also the brush was not favorably released.

(Curability Test Method)
Object of evaluation: To evaluate operation time of kneaded product of denture restorative material.
Evaluation method: A powder material and a liquid material prepared according to compounding table (Table 5) were kneaded in a specified kneading ratio for 30 seconds, and thereafter 0.5 ml of a rice cake-like kneaded product was taken and placed on about 20 g of a glass plate, and left to still stand for 30 seconds. One more glass plate having the same size as above was placed on the kneaded product, and furthermore 100 g of a weight was quietly placed thereon. After the weight was placed, the weight was removed at 30 seconds after initiation, and expansion of the circularity was calculated as the average value of the maximum and minimum diameters and was defined as the flow value. A larger flow value was determined as better fluidity. Such a procedure was performed and the change in fluidity was confirmed at standing times of 30 seconds, 60 seconds, 120 seconds and 180 seconds. The rating criteria of the amount of the change were defined based on the flow value at a standing time of 30 seconds and as follows. A case that the flow value at a standing time of 120 seconds was 90% or more and the flow value at a standing time of 150 seconds was 50% or less was rated as (A) because suitable operation time and curing time were achieved, a case that the flow value at a standing time of 120 seconds was less than 90% was rated as (B) because the operation time was too short, and a case that the flow value at a standing time of 150 seconds was more than 50% was rated as (C) because the curing time was too long.

(Discolorability Test)
[Object of Evaluation]

To evaluate degree of discoloration of cured article of denture restorative material.

[Evaluation Method]

A powder material and a liquid material prepared according to compounding table (Table 5) were kneaded in a specified kneading ratio for 30 seconds, the resulting kneaded product was filled in a 3 mm thick polyacetal mold having a through hole of a diameter of 8 mm, and both ends of the through hole were pressure-contacted by a polypropylene film and the resultant was left to stand for 5 hours to produce 6 test pieces. The surface of the resulting test pieces were subjected to buffing, and the samples after storage in water for 24 hours were defined as the initial immersed articles. Thereafter, 5 articles of the initial immersed articles were immersed in water at 80° C. for 7 days. After immersion, the articles were treated by washing with water and drying, and defined as treated test pieces, and the treated test pieces were relatively rated to the initial immersed article with respect to the degree of discoloration. The rating criteria are as follows. Five of the treated test pieces were prepared and rated by three persons, and the rating most frequently given from the three persons was defined as the test result.

A: The degrees of discoloration of the treated test pieces were the same as the degrees of discoloration of the initial immersed article.

Monomer containing (meth)acrylamide group (manufactured by FUJIFILM Corporation): FAM-201
Halogen ion-forming compound: trioctylmethylammonium chloride: TOMAC
Organic solvent: ethanol [Et]
Organic peroxide: benzoyl peroxide [BPO]
<Powder Material Components>
(Meth) acrylic acid (co) polymer: PMMA-PEMA copolymer [PMMA-PEMA]
Organometal compound: copper(II) acetylacetonate [CAA]
Barbituric acid derivative: 1-Cyclohexyl-5-propylbarbituric acid [CPBA]
Amine compound: N, N dimethylaniline [DMA]

The amounts of compounds in the each of the Examples and Comparative Examples, and the test results are shown in Table 5 below.

TABLE 5

| Liquid or Powder | Component | Abbreviation | Comparative Example 3-1 | Comparative Example 3-2 | Example 3-1 | Example 3-2 | Example 3-3 | Example 3-4 | Example 3-5 | Example 3-6 | Comparative Example 3-3 |
|---|---|---|---|---|---|---|---|---|---|---|---|
| Liquid | Monomer | MMA | 70 | | 70 | | 70 | 80 | 75 | 70 | 70 |
| | | 2EEMA | | 70 | | 70 | | | | | |
| | | HDDMA | 20 | | 20 | | 20 | 5 | 5 | 20 | 20 |
| | | HAPM | | 20 | | 20 | | | | | |
| | Hydrophilic monomer | HEMA | 10 | 10 | 10 | 10 | 10 | 15 | 20 | 10 | 10 |
| | Organic solvent | Et | 2.5 | 2.5 | 2.5 | 2.5 | 2.5 | 2.5 | 2.5 | 2.5 | 1 |
| | Organic peroxide | BPO | | | | | | | | 0.2 | |
| | Halogen ion-forming compound | TOMAC | 2 | 2 | 2 | 2 | 0.2 | 2 | 2 | | 2 |
| Powder | (Meth) acrylic acid (co) polymer | PMMA-PEMA | 100 | 100 | 100 | 100 | 100 | 100 | 100 | 100 | 100 |
| | Barbituric acid derivative | CPBA | 2 | 2 | 2 | 2 | 0.3 | 2 | 1.2 | 0.3 | 0.3 |
| | Organometal compound | CAA | 0.1 | 0.1 | 0.1 | 0.1 | 0.01 | 0.2 | 0.1 | | 0.1 |
| | Amine compound | DNA | | | | | | | | 0.01 | |
| | Monomer containing (meth)acrylamide group | FAM-401 FAM-201 | | | 1.1 | 2.2 | 11 | 16.5 | 22 | 11 | 2.2 |
| | Mixing ratio (Liquid:Powder) | | 1:1.5 | 1:1.6 | 1:1 | 1:1 | 1:1 | 1:1 | 1:1 | 1:1 | 1:2 |
| Test result | Adhesion bending strength test (MPpa) | | 45.4 | 42.1 | 67.4 | 72.6 | 71.6 | 68.3 | 64.2 | 69.4 | 51.5 |
| | Filling test | | A | A | A | A | A | A | A | A | A |
| | Curability test | | B | B | A | A | A | A | A | A | B |
| | Discolorability test | | B | B | A | A | A | A | A | A | A |

(pts.wt)

B: The degrees of discoloration of the treated test pieces were slightly different from the degrees of discoloration of the initial immersed article.
C: The degrees of discoloration of the treated test pieces were clearly different from the degrees of discoloration of the initial immersed article.

[Components and Abbreviations]
The abbreviations of the components used in the Examples are as follows.
<Liquid Material Components>
(Meth)acrylic acid group-containing monomer: methyl methacrylate [MMA]
(Meth)acrylic acid group-containing monomer: 2-ethoxyethyl methacrylate [2EEMA]
(Meth)acrylic acid group-containing monomer (crosslinkable): 1,6-hexanediol di(meth)acrylate[HDDMA]
(Meth)acrylic acid group-containing monomer (crosslinkable): 2-hydroxy-3-acryloyloxypropyl methacrylate [HAPM]
Hydrophilic monomer: 2-hydroxyethyl methacrylate [HEMA]
Monomer containing (meth)acrylamide group (manufactured by FUJIFILM Corporation): FAM-401

As shown in Table 5, Examples 3-1 to 3-6 exhibited higher strength in the adhesive bending strength test without impairing other physical properties, as compared with Comparative Examples 3-1 to 3-3.

[4. Tooth Substance Adhesive Primer]
A characteristic confirmation test method in case that the dental composition is the tooth substance adhesive primer is described below.
(1) Tooth Substance Adhesion Test
[Evaluation Purpose]
Evaluation of tooth substance adhesive property to an enamel and a dentin using various tooth substance adhesive primer.
[Evaluation Method]
After slaughter, a narrow piece of a cow tooth was prepared by extracting a permanent mandibular central incisor, freezing the incisor within 24 hours and unfreezing the incisor, and removing the root portion and cutting away the crown portion. The narrow piece of the cow tooth was embedded in an epoxy resin. The embedded cow tooth was sanded using #600 waterproof abrasive paper while pouring water to expose an enamel or a dentin, and then washed with water and dried for 5 seconds. A double-sided tape with a hole having a diameter of 4 mm was affixed to the exposed enamel or dentin to prescribe an adhesion surface. The prescribed adhesion area was subjected to a bonding treatment by a bonding technique specified in Examples or Comparative Examples. A plastic mold (inner diameter of 4 mm, height of 2 mm) was fixed on the prescribed surface subjected to the bonding treatment and the mold was filled with a photopolymerizable composite resin (BEAUTIFIL, manufactured by SHOFU INC.). The photopolymerizable composite resin was cured by irradiating with light for 30 seconds using a photopolymerization irradiation machine (Griplight II, manufactured by SHOFU INC.). After curing, the mold was removed and the resultant product was used as an adhesion test specimen. This adhesion test specimen was immersed in distilled water at 37° C. for 24 hours. After that, a tooth substance adhesion test was performed for shear bond strength, using an Instron universal testing machine (Instron 5567 manufactured by Instron) at a crosshead speed of 1 mm/min to measure an initial adhesive strength.

(2) Tooth Substance Adhesive Durability Test
[Evaluation Purpose]
Evaluation of tooth substance adhesive durability to an enamel and a dentin using various tooth substance adhesive primer.
[Evaluation Method]
After preparing an adhesion test specimen in the same manner as in the tooth substance adhesion test, the resultant adhesion test specimen was immersed in distilled water at 37° C. for 24 hours. A thermal cycle test of alternately immersing the test specimen in a constant temperature water tank maintained at 4° C. and a constant temperature water tank maintained at 60° C. for 1 minute is performed (2,000 cycles). After completion of the thermal cycle test, by using the adhesion test specimen, the tooth substance adhesion test was performed for shear bond strength at a crosshead speed of 1 mm/min, using an Instron universal testing machine (Instron 5567, manufactured by Instron Ltd.).

(3) Storage Stability Test
[Evaluation Purpose]
Evaluation of tooth substance adhesive property to an enamel and a dentin using each of composition after storing various dental adhesive primer compositions prepared under an atmosphere at 50° C. for 2 weeks.
[Evaluation Method]
In the same manner as in the tooth substance adhesion test, the tooth substance adhesion test was performed for shear bond strength.

[Components and Abbreviations]
The abbreviations of the components used in the Examples are as follows.
Bis-GMA: 2,2-bis(4-(3-methacryloyloxy-2-hydroxypropoxy)phenyl)propane
UDMA: Di(methacryloyloxy)-2,2,4-trimethylhexamethylenediurethane
TEGDMA: Triethylene glycoldimethacrylate
HEMA: 2-hydroxyethylmethacrylate
CQ: Camphorquinone
BPO: Benzoyl peroxide
DEPT: N, N-di(β-hydroxyethyl)-p-toluidine
DMB: Dimethylaminobenzoic acid
MHPA: 6-methacryloyloxyhexylphosphono acetate
MHPP: 6-methacryloyloxyhexyl-3-phosphonopropionate
META: 4-methacryloyloxyethyltrimellitic anhydride
MET: 4-methacryloyloxyethyltrimellitic acid
AETA: 4-acryloyloxyethyltrimellitic anhydride
AET: 4-acryloyloxyethyltrimellitic acid
FAM-401 (manufactured by FUJIFILM Corporation): Monomer containing (meth)acrylamide group
FAM-201 (manufactured by FUJIFILM Corporation): Monomer containing (meth)acrylamide group A. Preparation of Primer Composition
[Preparation of One-Pack Type Primer Composition (Compositions 4-1 to 4-7)]
According to the formulations shown in Table 6, one-pack type primer compositions (compositions 4-1 to 4-7) were prepared and used in Examples and Comparative Examples.

TABLE 6

| Composition No. | MHPA | MHPP | MET | AET | META | AETA | Bis-GMA | UDMA | Water | Aceton | Ethanol | CQ | DMB | FAM-401 | FAM-201 |
|---|---|---|---|---|---|---|---|---|---|---|---|---|---|---|---|
| Composition 4-1 | 2 | | | | 18 | | 1 | | 39 | 40 | | | 1 | 1 | |
| Composition 4-2 | | 3 | 30 | | | | 1 | | 29 | | 37 | 0.5 | 1 | 2 | |
| Composition 4-3 | 1 | | | 11 | | | 1 | | 49 | | 38 | 0.3 | 1 | 10 | |
| Composition 4-4 | 2 | | 19 | | | | | 20 | 20 | | 39 | 0.5 | 1 | 15 | |
| Composition 4-5 | 2 | | | | 18 | | 1 | | 39 | 40 | | | 1 | 20 | |
| Composition 4-6 | 2 | | | | 18 | | 1 | | 39 | 40 | | | 1 | | 1 |
| Composition 4-7 | | 5 | | | | 11 | | 14 | 30 | | 40 | 0.5 | 1 | | |

(pts.wt)

B. Preparation of Bonding Material Composition
[Preparation of Photopolymerizable One-Pack Type Bonding Material Composition (Compositions 4-A and 4-B)]
According to the formulations shown in Table 7, photopolymerizable one-pack type bonding material compositions (compositions 4-A and 4-B) were prepared and used in Examples and Comparative Examples.

TABLE 7

| Composition | Polymerizable monomer | | | | Photopolymerization catalyst | |
|---|---|---|---|---|---|---|
| No. | Bis-GMA | UDMA | TEGDMA | HEMA | CQ | DMB |
| Composition 4-A | | 50 | 30 | 20 | 0.5 | 1 |
| Composition 4-B | 50 | | 10 | 40 | 0.5 | 1 |

(pts.wt)

[Dual-Polymerizable Two-Pack Type Bonding Material Composition (Compositions 4-C and 4-D)]

According to the formulations shown in Table 8, dual-polymerizable two-pack type bonding material compositions (compositions 4-C and 4-D) were prepared and used in Examples and Comparative Examples.

TABLE 8

| Composition | | Polymerizable monomer | | | | Photo polymerization catalyst | | Chemical polymerization catalyst | |
|---|---|---|---|---|---|---|---|---|---|
| No. | | Bis-GMA | UDMA | TEGDMA | HEMA | CQ | DMB | DEPT | BPO |
| Composition 4-C | Bond I | | 50 | 30 | 20 | 0.5 | 1 | 1 | |
| | Bond II | | 50 | 30 | 20 | 0.5 | 1 | | 1 |
| Composition 4D | Bond I | 50 | | 10 | 40 | 0.5 | 1 | 1 | |
| | Bond II | 50 | | 10 | 40 | 0.5 | 1 | | 1 |

(pts.wt)

C. Evaluation of Tooth Substance Adhesive Property

Examples 4-1 to 4-5

A bonding treatment was performed by a two-step type adhesion system comprising a combination of one-pack type primer compositions 4-1 to 4-5 and a photopolymerizable one-pack type bonding material composition 4-A or 4-B (application of primer/standing for 10 seconds/drying/application of bonding material/light irradiation for 10 seconds).

After passing through a filling operation of a photopolymerizable composite resin (BEAUTIFIL, manufactured by SHOFU INC.), a tooth substance adhesion test, a tooth substance adhesive durabilit and a storage stability test were performed. The results are shown in Table 9.

As shown in Table 9, it was confirmed that the adhesion system comprising one-pack type primer compositions 4-1 to 4-5 have excellent tooth substance adhesive property (after immersing in water at 37° C. for 24 hours) to an enamel and a dentin. It was also found that the adhesion system comprising one-pack type primer compositions 4-1 to 4-5 have excellent adhesive durability since an adhesive strength did not decrease with respect to adhesive durability after 2,000 thermal cycles in both an enamel and a dentin when compared with tooth substance adhesive property after immersing in water at 37° C. for 24 hours. Furthermore, the one-pack type primer compositions 4-1 to 4-5 did not cause deterioration or change in quality as a result of hydrolysis even when stored at 50° C. for 2 weeks and maintained initial tooth substance adhesive property (after immersing in water at 37° C. for 24 hours) and were excellent in storage stability.

Comparative Examples 1 to 2

A bonding treatment was performed by a two-step type adhesion system comprising a combination of one-pack type primer compositions 4-6 to 4-7 and a photopolymerizable one-pack type bonding material composition 4-A or 4-B (application of primer/standing for 10 seconds/drying/application of bonding material/light irradiation for 10 seconds), and the same tests as those in Examples 4-1 to 4-5 were performed. The results are shown in Table 9.

As shown in Table 9, it was confirmed that in the adhesive systems using the one-pack type primer compositions 4-6 to 4-7, the bond strength to a dentin and an enamel in the tooth substance adhesive property, the adhesive durability and the storage stability were low compared to the adhesive system using the one-pack type primer compositions 4-1 to 4-5.

Examples 4-6 to 4-7

A bonding treatment was performed by a two-step type adhesion system comprising a combination of a dual-polymerizable two-pack type bonding material composition 4-C or 4-D and one-pack type primer composition 4-2 (application of primer/standing for 10 seconds/drying/mixing of bonding materials in the same amount and application).

After passing through a filling operation of a photopolymerizable composite resin (BEAUTIFIL, manufactured by SHOFU INC.), a tooth substance adhesive property test, a tooth substance adhesive durability test and a storage stability test were performed. The results are shown in Table 9.

As shown in Table 9, it was confirmed that one-pack type primer composition 4-2 has excellent tooth substance adhesive property (after immersing in water at 37° C. for 24 hours) to an enamel and a dentin even in an adhesion system comprising a dual-polymerizable bonding material. It was also found that the adhesion system comprising one-pack type primer composition 4-2 has excellent adhesive durability since an adhesive strength did not decrease with respect to adhesive durability after 2,000 thermal cycles in both an enamel and a dentin when compared with tooth substance adhesive property after immersing in water at 37° C. for 24 hours. Furthermore, the one-pack type primer composition 4-2 did not cause deterioration or change in quality as a result of hydrolysis even when stored at 50° C. for 2 weeks and maintained initial tooth substance adhesive property (after immersing in water at 37° C. for 24 hours) and were excellent in storage stability.

TABLE 9

| Example No. | Primer Composition No. | Bonding material Composition No. | Tooth substance adhesion (Mpa) Enamel | Tooth substance adhesion (Mpa) Dentin | Adhesive durability (Mpa) Enamel | Adhesive durability (Mpa) Dentin | Storage stability (Mpa) Enamel | Storage stability (Mpa) Dentin |
|---|---|---|---|---|---|---|---|---|
| Example 4-1 | Composition 4-1 | One-pack type composition 4-A | 18.2 | 18.1 | 16.5 | 17.9 | 16.9 | 17.2 |
| Example 4-2 | Composition 4-2 | One-pack type composition 4-B | 21.1 | 20.2 | 19.1 | 20.9 | 17.8 | 19.5 |
| Example 4-3 | Composition 4-3 | One-pack type composition 4-A | 20.6 | 21.4 | 19.8 | 21.7 | 18.5 | 20.6 |
| Example 4-4 | Composition 4-4 | One-pack type composition 4-A | 18.5 | 17.5 | 18.7 | 17.4 | 16.6 | 18.1 |
| Example 4-5 | Composition 4-5 | One-pack type composition 4-A | 17 | 16.8 | 17.7 | 18 | 15.5 | 18.1 |
| Comparative Example 4-1 | Composition 4-6 | One-pack type composition 4-A | 14.5 | 13.6 | 14.7 | 13.8 | 13.8 | 12.8 |
| Comparative Example 4-2 | Composition 4-7 | One-pack type composition 4-A | 13.1 | 13.5 | 14 | 14.8 | 12.7 | 14.1 |
| Example 4-6 | Composition 4-2 | Two pack mixing type composition 4-C | 20.6 | 20.5 | 19.7 | 20.5 | 17.3 | 19.2 |
| Example 4-7 | Composition 4-2 | Two pack mixing type composition 4-D | 20.7 | 21.3 | 19.4 | 20.7 | 17.4 | 20.1 |

[5. Dental Primer]

A characteristic confirmation test method in case that the dental composition is the dental primer is described below.

[Adhesion Test Method]

(Initial Adhesion Test)

Adhesion test specimen was immersed in 37° C. of water for 24 hours. Thereafter, adhesion test was performed.

(Durability Adhesion Test)

Adhesion test specimen was immersed in 37° C. of water for 24 hours. After immersion, 10000 times of thermal cycle (5° C.<-->50° C., immersion in each temperature for 1 minute) was applied. Thereafter, adhesion test was performed.

(Shelf Life Test)

After preparing the dental primer, 5 cc of the dental primer was collected into an airtight container. The airtight container was preserved for 1 year at a dark cold place of 23° C., and thereafter the Initial adhesion test and Durability adhesion test were performed.

[Preparation of Sample]

Dental primer: P5-1 to P5-7, Adhesive material: 5-B, and a Resin cement: 5-RC were prepared in accordance with an ordinary method by using following component at the formulation ratio shown in Tables 10 and 11.

(Dental Primer: P5-1 to P5-7)

<Organic Solvent>
Anhydrous ethanol
Aceton
<Silane Coupling Agent>
γ-methacryloyloxypropyl triethoxysilane
γ-methacryloyloxypropyl trimethoxysilane
<Acid Anhydride and/or Weakly Acidic Compound>
Citric anhydride
Maleic anhydride
Pyrophosphoric acid
<Strongly Acidic Compound>
Phosphoric acid
<Monomer Containing (Meth)Acrylamide Group>
FAM-401 (manufactured by FUJIFILM Corporation)
FAM-201 (manufactured by FUJIFILM Corporation)

(Adhesive Material: 5-B)
<Polymerizable Monomer>
2-hydroxyethyl (meth)acrylate (2HEMA)
2-hydroxy-3-acryloyloxypropyl methacrylate (2HPA)
2,2-bis(4-(3-methacryloyloxy-2-hydroxypropoxy)phenyl) propane (Bis-GMA)
4-(meth)acryroyloxybuthyl trimellic anhydride (4MABT)
<Polymerization Catalyst (Photo Polymerization Initiator)>
Camphor quinone
Ethyl p-N,N-dimethylaminobenzoate (Resin Cement: 5-RC)
<Polymerizable Monomer>
2-hydroxyethyl (meth)acrylate (2HEMA)
2-hydroxy-3-acryloyloxypropyl methacrylate (2HPA)
2,2-bis(4-(3-methacryloyloxy-2-hydroxypropoxy)phenyl) propane (Bis-GMA)
4-(meth)acryroyloxybuthyl trimellic anhydride (4MABT)
<Polymerization Catalyst (Chemical Polymerization Initiator)>
Benzoylperoxide (BPO) and ethyl p-N,N-dimethylaminobenzoate
<Filler>
Silane-treated glass (average particle diameter: 3 μm)
Aerosil (R972)

[Lithium Disilicate Glass Ceramics]
(Preparation of Adherend and Adhesive Body)

Lithium disilicate glass ceramics adherend and Lithium disilicate glass ceramics adhesive body were prepared by molding lithium disilicate glass ceramics (manufactured by SHOFU INC.) using CAD/CAM system or press system, then firing in accordance with the instruction, washing and storing in water for 1 week. The Lithium disilicate glass ceramics adherend (Large) was in a columnar shape formed to have a dimension of 2 cm (diameter) by 1 cm (thickness). The Lithium disilicate glass ceramics adherend (Small) was in a columnar shape formed to have a dimension of 0.5 cm (diameter) by 1 cm (thickness).

(Preparation of Adhesion Test Specimen)

The Lithium disilicate glass ceramics adherend (Large) and the Lithium disilicate glass ceramics adherend (Small) were sandblasted with alumina having an average particle size of about 50 μm (with 0.2 MPa, for 1 second), and the Lithium disilicate glass ceramics adherend (Small) was applied with one of the Adhesive material: 5-B. Thereafter, Lithium disilicate glass ceramics adherend (Small) was pressure contacted to the Lithium disilicate glass ceramics adherend (Large). The excess adhesive material was removed. Subsequently, the pressure contacted Lithium disilicate glass ceramics (Large) and the Lithium disilicate glass ceramics (Small) were left for 15 minutes for curing to prepare adhesion test specimen (the number of test specimen N=5).

[Porcelain]
(Preparation of Adherend and Adhesive Body)

Porcelain adherend and Porcelain adhesive body were prepared by building-up and firing "VINTAGE LD" (manufactured by SHOFU INC.) in accordance with the instruction, and washing and storing in water for 1 week. The Porcelain adherend (Large) was in a columnar shape formed to have a dimension of 2 cm (diameter) by 1 cm (thickness). The Porcelain adherend (Small) was in a columnar shape formed to have a dimension of 0.5 cm (diameter) by 1 cm (thickness).

(Preparation of Adhesion Test Specimen)

The Porcelain adherend (Large) and the Porcelain adherend (Small) were sandblasted with alumina having an average particle size of about 50 μm (with 0.2 MPa, for 1 second), and were applied with one of the dental primer: P5-1 to 5-7 and dried. Thereafter, Porcelain adherend (Small) were applied with mixed resin cement (5-RC), and were pressure contacted to the Porcelain adherend (Large). The excess cement was removed. Subsequently, the pressure contacted Porcelain adherend (Large) and the Porcelain adherend (Small) were left for 15 minutes for curing to prepare adhesion test specimen (the number of test specimen N=5).

[Composite]
(Preparation of Adherend)

Composite resin adherend was prepared by cutting and machining the resin disk material "SHOFU DISK HC" (manufactured by SHOFU INC.) using CAD/CAM system, and washing and storing in water for 1 week. The composite resin adherend was in a columnar shape formed to have a dimension of 2 cm (diameter) by 1 cm (thickness).

(Preparation of Adhesion Test Specimen)

The composite resin adherend was applied with one of the dental primer: P5-1 to P5-7 and dried. Thereafter, adhesive material (5-B) was applied, and light irradiation was performed for 30 seconds by Griplight 2 (manufactured by SHOFU INC.). The adhesion surface was defined by using jig having a diameter of 0.5 mm, then was filled with composite resin (LITE FIL 2: manufactured by SHOFU INC.). The composite resin was cured by irradiating light for 30 seconds by Griplight 2 (manufactured by SHOFU INC.) to prepare adhesion test specimen (the number of test specimen N=5).

TABLE 10

| Dental primer (g %) | | P5-1 | P5-2 | P5-3 | P5-4 | P5-5 | P5-6 | P5-7 |
|---|---|---|---|---|---|---|---|---|
| Organic solvent | Anhydrous ethanol | 85.0 | 93.0 | 81.0 | 77.0 | 47.0 | 85.0 | 90.0 |
| | Aceton | | | | | 47.0 | | |
| Silane coupling agent | γ-methacryloyloxypropyl triethoxysilane | | 4.0 | | | | | |
| | γ-methacryloyloxypropyl trimethoxysilane | 4.0 | | 4.0 | 4.0 | 4.0 | 4.0 | 4.0 |
| Acid anhydride and/or weakly acidic compound | Citric anhydride | | | | 1.0 | | | |
| | Maleic anhydride | 1.0 | 1.0 | 1.0 | | 1.0 | | 1.0 |
| | Pyrophosphoric acid | | | | | | 1.0 | |
| Strongly acidic compound | Phosphoric acid | | | | | | | |
| Monomer containing (meth)acrylamide group | FAM-401 | 10.0 | 2.0 | 14.0 | 18.0 | 1.0 | 10.0 | |
| | FAM-402 | | | | | | | 5.0 |
| Total | | 100.0 | 100.0 | 100.0 | 100.0 | 100.0 | 100.0 | 100.0 |

TABLE 11

| | | Adhesive material: 5-B (g %) | Resin cement: 5-RC (g %) | |
|---|---|---|---|---|
| | | | First paste | Second paste |
| Polymerizable monomer | 2HEMA | 10 | 5 | 5 |
| | 2HPA | 80 | 40 | 40 |
| | Bis-GMA | 2 | 1 | 1 |
| | 4MABT | 5 | 2.5 | 2.5 |
| Filler | Silane-treated glass (average particle diameter: 3 μm) | | 1 | 1 |
| | Aerosil (R972) | | 0.1 | 0.1 |
| Photo polymerization | Camphor quinone | 2 | | |
| | Ethyl p-N,N-dimethylaminobenzoate | 1 | | |

TABLE 11-continued

|  | Adhesive material: 5-B (g %) | Resin cement: 5-RC (g %) | |
|---|---|---|---|
|  |  | First paste | Second paste |
| Chemical polymer-ization | Benzoylperoxide (BPO) | 0.3 |  |
|  | Ethyl p-N,N-dimethylaminobenzoate |  | 0.5 |
| Composite resin (5-CR) | LITE FIL 2 (manufactured by SHOFU INC.) | | |

In examples 5-1 to 5-6 (adhesion between Lithium disilicate glass ceramics and Lithium disilicate glass ceramics using resin cement (5-RC)), examples 5-7 to 5-12 (adhesion of composite resin (5-CR) to composite resin adherend using adhesive material (5-B)) and examples 5-13 to 5-18 (adhesion between porcelain and porcelain using resin cement (5-RC)) which use the dental primer of the present disclosure, although the materials and method of adhesive are different in these examples, it was confirmed that adhesive strength was stable in both of Initial adhesion test and Durability adhesion test regardless of "Shelf life test".

On the other hand, in the Comparative Examples 5-1 to 5-3, although the materials and method of adhesive are

TABLE 12

| Sample preparation | | | Example 5-1 | Example 5-2 | Example 5-3 | Example 5-4 | Example 5-5 | Example 5-6 | Comparative Example 5-1 |
|---|---|---|---|---|---|---|---|---|---|
| Dental primer | | | P5-1 | P5-2 | P5-3 | P5-4 | P5-5 | P5-6 | P5-7 |
| Adhesive material: 5-B, Resin cement: 5-RC | | | 5-RC | 5-RC | 5-RC | 5-RC | 5-RC | 5-RC | 5-RC |
| Adherend | Lithium disilicate glass ceramics adherend (Large) Composite resin adherend Porcelain adherend (Large) | | ○ | ○ | ○ | ○ | ○ | ○ | ○ |
| Adhesive body | Lithium disilicate glass ceramics adherend (Small) Composite resin Porcelain adherend (Small) | | ○ | ○ | ○ | ○ | ○ | ○ | ○ |

| Test result | | Example 5-1 | Example 5-2 | Example 5-3 | Example 5-4 | Example 5-5 | Example 5-6 | Comparative Example 5-1 |
|---|---|---|---|---|---|---|---|---|
| Without shelf life test | Initial adhesion (MP) | 15.2 | 15.5 | 14.7 | 12.5 | 14.1 | 15.1 | 7.7 |
|  | Thermal (MP) | 15.0 | 15.3 | 14.4 | 11.1 | 13.4 | 15.2 | 8.3 |
| With shelf life test | Initial adhesion (MP) | 15.1 | 15.4 | 14.5 | 11.7 | 13.7 | 15.1 | Fallen off |
|  | Thermal (MP) | 14.8 | 15.3 | 14.3 | 11.4 | 13.1 | 15.0 | — |

| Sample preparation | | | Example 5-7 | Example 5-8 | Example 5-9 | Example 5-10 | Example 5-11 | Example 5-12 | Comparative Example 5-2 |
|---|---|---|---|---|---|---|---|---|---|
| Dental primer | | | P5-1 | P5-2 | P5-3 | P5-4 | P5-5 | P5-6 | P5-7 |
| Adhesive material: 5-B, Resin cement: 5-RC | | | 5-B | 5-B | 5-B | 5-B | 5-B | 5-B | 5-B |
| Adherend | Lithium disilicate glass Composite resin adherend Porcelain adherend (Large) | | ○ | ○ | ○ | ○ | ○ | ○ | ○ |
| Adhesive body | Lithium disilicate glass Composite resin Porcelain adherend (Small) | | ○ | ○ | ○ | ○ | ○ | ○ | ○ |

| Test result | | Example 5-7 | Example 5-8 | Example 5-9 | Example 5-10 | Example 5-11 | Example 5-12 | Comparative Example 5-2 |
|---|---|---|---|---|---|---|---|---|
| Without shelf life test | Initial adhesion (MP) | 14.1 | 14.5 | 13.5 | 11.6 | 13.0 | 14.4 | 7.5 |
|  | Thermal (MP) | 14.0 | 13.8 | 13.2 | 11.8 | 13.9 | 14.0 | 7.9 |
| With shelf life test | Initial adhesion (MP) | 14.3 | 13.8 | 13.3 | 11.3 | 13.8 | 14.0 | Fallen off |
|  | Thermal (MP) | 14.2 | 13.7 | 12.9 | 10.9 | 14.0 | 13.9 | — |

| Sample preparation | | | Example 5-13 | Example 5-14 | Example 5-15 | Example 5-16 | Example 5-17 | Example 5-18 | Comparative Example 5-3 |
|---|---|---|---|---|---|---|---|---|---|
| Dental primer | | | P5-1 | P5-2 | P5-3 | P5-4 | P5-5 | P5-6 | P5-7 |
| Adhesive material: 5-B, Resin cement: 5-RC | | | 5-RC | 5-RC | 5-RC | 5-RC | 5-RC | 5-RC | 5-RC |
| Adherend | Lithium disilicate glass Composite resin adherend Porcelain adherend (Large) | | ○ | ○ | ○ | ○ | ○ | ○ | ○ |
| Adhesive body | Lithium disilicate glass Composite resin Porcelain adherend (Small) | | ○ | ○ | ○ | ○ | ○ | ○ | ○ |

| Test result | | Example 5-13 | Example 5-14 | Example 5-15 | Example 5-16 | Example 5-17 | Example 5-18 | Comparative Example 5-3 |
|---|---|---|---|---|---|---|---|---|
| Without shelf life test | Initial adhesion (MP) | 13.5 | 13.8 | 12.8 | 11.1 | 12.5 | 13.7 | 7.0 |
|  | Thermal (MP) | 13.8 | 13.5 | 13.0 | 10.3 | 12.0 | 13.6 | 7.2 |
| With shelf life test | Initial adhesion (MP) | 13.3 | 13.2 | 12.7 | 10.7 | 12.2 | 13.3 | Fallen off |
|  | Thermal (MP) | 13.7 | 13.0 | 12.2 | 10.1 | 12.5 | 13.5 | — | different in these comparative examples, certain adhesive strength was confirmed in both of Initial adhesion test and Durability adhesion test of "Without shelf life test". However, in "With shelf life test", although it was possible to prepare the adhesion test specimen, it was confirmed that adhesive body had already fallen off at the stage of the Initial adhesion test.

[6. Dental Adhesive Composition]

A characteristic confirmation test method in case that the dental composition is the dental adhesive composition is described below.

(1) Tooth Substance Adhesion Test

[Evaluation Purpose]

Evaluation of tooth substance adhesive property in the composition.

[Evaluation Method]

After slaughter, a narrow piece of a cow tooth was prepared by extracting a permanent mandibular central incisor, freezing the incisor within 24 hours and unfreezing the incisor, and removing the root portion and cutting away the crown portion. The narrow piece of the cow tooth was embedded in an epoxy resin. The embedded cow tooth was sanded using #600 waterproof abrasive paper while pouring water to expose an enamel or a dentin, and then washed with water.

A double-sided tape with a hole having a diameter of 4 mm was affixed to the exposed enamel or dentin to prescribe an adhesion surface. Fluorobond II primer was sufficiently applied to the entire inner wall of the prescribed adhesive surface, and the primer was left to stand for 10 seconds and then air-dried. Thereafter, the material described in Example or comparative examples was prepared and applied sufficiently to the entire prescribed adhesive surface and left for 10 seconds. A plastic mold (inside diameter: 4 mm, height: 2 mm) was fixed to the adhesive treated surface, and the photopolymerizable composite resin "Beautifil II" (manufactured by SHOFU INC.) was filled in the mold, and irradiated with light for 30 seconds using a photo polymerization irradiator (Grip Light II manufactured by SHOFU INC.) to be cured. After curing, the mold was removed to prepare an adhesion test specimen.

The adhesion test specimen was immersed in distilled water at 37° C. for 24 hours. After that, a tooth substance adhesion test was performed for shear bond strength, using an Instron universal testing machine (Instron 5567 manufactured by Instron) at a crosshead speed of 1 mm/min. The number of samples was 6, and the average value was calculated.

[Components and Abbreviations]

The abbreviations of the components used in the Examples are as follows.

Bis-GMA: 2,2-bis[4-(3-methacryloyloxy-2-hydroxypropoxy)phenyl]propane
UDMA: 2,2-bis(4methacryloyloxyethoxyphenyl)propane
TEGDMA: Triethylene glycol di(meth)acrylate
HEMA: 2-hydroxyethyl methacrylate
CQ: Camphor quinone
Tin: Dibutyltin dilaurate
R-972: Aerosil R-972
FAM-401 (manufactured by FUJIFILM Corporation): Monomer containing (meth)acrylamide group
FAM-201 (manufactured by FUJIFILM Corporation): Monomer containing (meth)acrylamide group

[Preparation of One-Liquid Type Composition (Compositions 6-1 to 6-9)]

One-liquid type compositions (Compositions 6-1 to 6-9) were prepared according to the formulation shown in Table 13 and used in Examples and Comparative Examples.

TABLE 13

| Composition No. | Example No. | Bis-GMA | UDMA | TEGDMA | HEMA | FAM-401 | FAM-201 | R-972 | CQ | Tin | Tooth substance Enamel | Dentin |
|---|---|---|---|---|---|---|---|---|---|---|---|---|
| 6-1 | Example 6-1 | | 46.9 | 19.6 | 24.4 | 2.1 | | 7.0 | 0.7 | 1.4 | 21.1 | 18.5 |
| 6-2 | Example 6-2 | | 40.0 | 17.2 | 25.8 | 10.0 | | 7.0 | 0.5 | 1.0 | 20.3 | 16.2 |
| 6-3 | Example 6-3 | 23.5 | | 31.5 | 23.0 | 15.0 | | 7.0 | 0.5 | 1.0 | 19.2 | 18.8 |
| 6-4 | Example 6-4 | | 53.5 | 21.8 | 17.5 | 0.2 | | 7.0 | 0.5 | 1.0 | 14.8 | 14.5 |
| 6-5 | Example 6-5 | 25.0 | | 41.3 | 6.7 | 20.0 | | 7.0 | 0.6 | 1.2 | 14.3 | 14.1 |
| 6-6 | Example 6-6 | | 49.7 | 14.3 | 30.0 | 6.0 | | | 0.7 | 1.4 | 20.8 | 15.6 |
| 6-7 | Example 6-7 | 30.6 | | 42.2 | 26.0 | 1.2 | | | 0.5 | 1.0 | 18.7 | 13.2 |
| 6-8 | Comparative Example 6-1 | | 40.0 | 28.0 | 25.0 | | | 7.0 | 0.5 | 1.0 | 12.9 | 11.5 |
| 6-9 | Comparative Example 6-2 | 43.0 | | 36.0 | 12.0 | | 2.0 | 7.0 | 0.6 | 1.2 | 15.1 | 10.7 |

Examples 6-1 to 6-7

As shown in Table 13, it was confirmed that the compositions 6-1 to 6-7 have excellent tooth substance adhesive property to both an enamel and a dentin.

Comparative Examples 6-1 to 6-2

Respective tests were performed individually using the prepared one-pack type compositions 6-8 to 6-9 (Comparative Examples 6-1 to 6-2) in the same manner as in Examples 6-1 to 6-7, and the results were shown in Table 13. As shown in Table 13, it was confirmed that the compositions 6-8 to 6-9 could not obtain sufficient tooth substance adhesive property to both an ename and a dentin.

[7. Tooth Substance Adhesive Composition]

A characteristic confirmation test method in case that the dental composition is the tooth substance adhesive composition is described below.

(1) Tooth Substance Adhesion Test

[Evaluation Purpose]

Evaluation of tooth substance adhesive property in the composition.

[Evaluation Method]

After slaughter, a narrow piece of a cow tooth was prepared by extracting a permanent mandibular central incisor, freezing the incisor within 24 hours and unfreezing the incisor, and removing the root portion and cutting away the crown portion. The narrow piece of the cow tooth was embedded in an epoxy resin. The embedded cow tooth was sanded using #600 waterproof abrasive paper while pouring water to expose an enamel or a dentin, and then washed with water.

A double-sided tape with a hole having a diameter of 4 mm was affixed to the exposed enamel or dentin to prescribe an adhesion surface. The material described in Example or Comparative examples was prepared and applied suffi-ciently to the entire prescribed adhesive surface and left for 10 seconds. A plastic mold (inside diameter: 4 mm, height: 2 mm) was fixed to the adhesive treated surface, and the photopolymerizable composite resin "Beautifil II" (manufactured by SHOFU INC.) was filled in the mold, and irradiated with light for 30 seconds using a photo polymerization irradiator (Grip Light II manufactured by SHOFU INC.) to be cured. After curing, the mold was removed to prepare an adhesion test specimen.

The adhesion test specimen was immersed in distilled water at 37° C. for 24 hours. After that, a tooth substance adhesion test was performed for shear bond strength, using an Instron universal testing machine (Instron 5567 manufactured by Instron) at a crosshead speed of 1 mm/min. The number of samples was 6, and the average value was calculated.

[Components and Abbreviations]

The abbreviations of the components used in the Examples are as follows.
UDMA: Di(methacryloyloxy)-2,2,4-trimethyl hexamethylene diurethane
2.6E: Bis-methacryloyl ethoxyphenyl propane
HEMA: 2-hydroxyethyl methacrylate
CQ: Camphor quinone
DMA: N, N dimethylaniline
p-TSNa: p-toluene sulfinate sodium
R-972: Aerosil R-972
MHPA: (6-methacryloxy) hexylphosphonoacetate
META: 4-methacryloyloxyethyl trimellitic anhydride
MET: 4-methacryloyloxyethyl trimellitic acid
EtOH: Ethanol
FAM-401: Monomer containing (meth)acrylamide group (manufactured by FUJIFILM Corporation)
FAM-201: Monomer containing (meth)acrylamide group (manufactured by FUJIFILM Corporation)

[Preparation of One-Pack Type Composition (Compositions 7-1 to 7-7)]

One-pack type compositions were prepared according to the formulation shown in Table 14 and used in Examples and Comparative Examples.

TABLE 14

| Composition No. | Example No. | UDMA | 2.6E | HEMA | MET | META | MHPA | FAM-401 | FAM-201 | R-972 | EtOH | Water | CQ | DMA | p-TSNa | Tooth substance adhesion (Mpa) Enamel | Dentin |
|---|---|---|---|---|---|---|---|---|---|---|---|---|---|---|---|---|---|
| 7-1 | Example 7-1 | | 2.0 | 10.5 | | 5.5 | 4.7 | 2.1 | | 4.3 | 48.7 | 22.2 | 0.7 | 0.7 | 1.2 | 15.5 | 16.1 |
| 7-2 | Example 7-2 | 7.5 | | 8.7 | | 6.4 | 4.3 | 9.1 | | 3.3 | 39.7 | 21.0 | 0.7 | 0.7 | 1.2 | 16.7 | 17.2 |
| 7-3 | Example 7-3 | 8.0 | | 8.5 | | 5.4 | 2.1 | 13.0 | | 3.0 | 37.0 | 23.0 | 0.7 | 0.7 | 1.2 | 12.2 | 13.4 |
| 7-4 | Example 7-4 | | 4.8 | 13.8 | 7.0 | | 7.0 | 1.2 | | 3.3 | 39.9 | 23.0 | 0.7 | 0.7 | 1.2 | 11.9 | 11.5 |
| 7-5 | Example 7-5 | | 2.0 | 6.0 | 6.5 | | 3.5 | 17.0 | | 3.0 | 39.0 | 23.0 | 0.7 | 0.7 | 1.2 | 10.2 | 11.7 |
| 7-6 | Comparative Example 7-1 | 16.0 | | 20.0 | 11.5 | | 10.5 | | 2.0 | 0.9 | 18.1 | 21.0 | 0.7 | 0.7 | 1.2 | 5.6 | 6.1 |
| 7-7 | Comparative Example 7-2 | | 2.8 | 10.8 | | 5.4 | 5.5 | | | 4.3 | 48.7 | 22.5 | 0.7 | 0.7 | 1.2 | 5.9 | 4.5 |

Examples 7-1 to 7-5

The tooth substance adhesiveness test was performed individually using the prepared one-pack type compositions 7-1 to 7-5 (Examples 7-1 to 7-5) without using any other treating material. The results are shown in Table 14. As shown in Table 14, it was confirmed that the compositions 7-1 to 7-5 have excellent tooth substance adhesive property to both an enamel and a dentin.

Comparative Examples 7-1 to 7-2

Respective tests were performed individually using the prepared one-pack type compositions 7-6 to 7-7 (Comparative Examples 7-1 to 7-2) in the same manner as in Examples 7-1 to 7-5, and the results were shown in Table 14. As shown in Table 14, it was confirmed that the compositions 7-6 to 7-7 could not obtain sufficient tooth substance adhesive property to both an enamel and a dentin.

[8. Dental Adhesive Resin Cement]

A characteristic confirmation test method in case that the dental composition is the dental adhesive resin cement is described below.

As an example of a dental ceramics material consisting of aluminum oxide or a zirconium oxide, an aluminum oxide plate (about 15×15×2 mm [manufactured by Japan Fine Ceramics Co., Ltd.]) and a zirconium oxide plate (about 15×15×2 mm [manufactured by Japan Fine Ceramics Co., Ltd.]) were used and a tensile adhesion strength test was performed. A dental adhesive resin cement was prepared by mixing at a weight ratio shown in Table 15.

A flat surface of an aluminum oxide or zirconium oxide plate of about 15×15×2 mm was polished with a No. 240, then, No. 600 silicon carbide paper [manufactured by Sankyo Rigaku Co., Ltd.] under running water to obtain a smooth surface, the smooth surface was subjected to air ablation (50 μm alumina beads, 2.5 kgf/cm² pressure), and was washed with water to obtain an adherend. Separately, an adhesive surface of a cylindrical stainless bar of diameter 5 mm×height 10 mm was subjected to air ablation (50 μm alumina beads, 5 kgf/cm² pressure) and, thereafter, the surface was ultrasound-washed and air-dried to obtain a jig for measuring an adhesion strength. The adhesive surface of the adherend and the adhesive surface of a stainless bar were adhered by intervening the resin cement prepared in Example or Comparative Example therebetween. Thereupon, an extra cement was removed with a mini-brush, and photopolymerization was performed for 10 seconds using "Shofu Grip Light II" in a cement margin.

All six test pieces were immersed in water at 37° C. and, after immersion in water 37° C. for 24 hours, a tensile adhesion strength was measured. For measuring an adhesion strength, a tensile adhesion strength was measured using a universal tester (manufactured by Instron) under the condition of a cross-head speed of 1 mm/min. All adhesion tests were performed at room temperature of 23° C.±1° C.

Herein, a tensile adhesion strength when a dental adhesive resin cement was prepared by blending and mixing at a weight ratio shown in Table 15, and this was brought into the sealed state, and was used under storage environment at 23° C. within 24 hours was adopted as an "initial" tensile adhesion strength. In addition, a tensile adhesion strength when a dental adhesive resin cement was prepared by blending and mixing at a weight ratio shown in Table 15, and this was brought into the sealed state, and was used after storage for 2 months under storage environment at 50° C. was adopted as tensile strength "after 50° C. 2 months storage".

As an example of a dental ceramics material containing silicon dioxide as a main component, a dental metal baking porcelain [trade name "Vintage Hello" (manufactured by SHOFU INC.)] was used, and a disk-like (diameter 15.0×5.0 mm) fired product was prepared using a vacuum electric furnace for firing a porcelain [trade name "Twin Mat" (manufactured by SHOFU INC.)], and a tensile adhesion strength test was performed. A dental adhesive resin cement was prepared by mixing at a weight ratio shown in Table 15.

A flat surface of a disk-like (diameter 15.0×5.0 mm) fired product was polished under running water using a No. 240, then, No. 600 silicon carbide paper [manufactured by Sankyo Rigaku Co., Ltd.] to obtain a smooth surface, and this was washed with water to obtain an adherend.

Separately, an adhesive surface of a cylindrical Cobaltan (cobalt chromium alloy: manufactured by SHOFU INC.) bar of diameter 5 mm×height 10 mm was subjected to air ablation (50 μm alumina beads, 5 kgf/cm² pressure) and, thereafter, was ultrasound-washed and air-dried to obtain a jig for measuring an adhesion strength. The adhesive surface of the adherend and then adhesive surface of a stainless bar were adhered by intervening the resin cement prepared in Example or Comparative Example therebetween. Thereupon, an excess cement was removed with a mini-brush, and photopolymerization was performed for 10 seconds using "Shofu Grip Light II" in a cement margin.

All six test pieces were immersed in water at 37° C. and, after immersion in water 37° C. for 24 hours, a tensile adhesion strength was measured. For measuring an adhesion strength, a tensile adhesion strength was measured using a universal tester (manufactured by Instron) under the condition of a cross-head speed of 1 mm/min. All adhesion tests were performed at room temperature of 23° C.±1° C.

Herein, a tensile adhesion strength when a dental adhesive resin cement was prepared by blending and mixing at a weight ratio shown in Table 15, and this was brought into the sealed state, and was used under storage environment at 23° C. within 24 hours was adopted as an "initial" tensile adhesion strength. In addition, a tensile adhesion strength when a dental adhesive resin cement was used after storage for 2 months under storage environment at 50° C. was adopted as tensile strength "after 50° C. 2 months storage".

As an example of a dental precious metal material, a gold alloy flat plate (approximately 15×15×2 mm [SUPER GOLD Type 4 (manufactured by SHOFU INC.)]) was used to perform a tensile adhesive strength test. The resin cements were prepared by mixing in the weight ratios in Examples or Comparative Examples shown in Table 15.

A flat surface of a gold alloy flat plate of about 15×15×2 mm was polished under running water using a No. 600 silicon carbide paper [manufactured by Sankyo Rigaku Co., Ltd.] to obtain a smooth surface, and the smooth surface was subjected to air ablation (50 μm alumina beads, 5.0 kgf/cm² pressure), and washed with water to obtain an adherend.

Separately, an adhesive surface of a cylindrical stainless bar of diameter 5 mm×height 10 mm was subjected to air ablation (50 μm alumina beads, 5 kgf/cm² pressure) and, thereafter, the surface was ultrasound-washed and air-dried to obtain a jig for measuring an adhesion strength. The adhesive surface of the adherend and the adhesive surface of a stainless bar were adhered by intervening the resin cement prepared in Example or Comparative Example therebetween. Thereupon, an excess cement was removed with a mini-brush, and photopolymerization was performed for 10 seconds using "Shofu Grip Light II" in a cement margin.

All six test pieces were immersed in water at 37° C. and, after immersion in water 37° C. for 24 hours, a tensile adhesion strength was measured. For measuring an adhesion strength, a tensile adhesion strength was measured using a universal tester (manufactured by Instron) under the condition of a cross-head speed of 1 mm/min. All adhesion tests were performed at room temperature of 23° C.±1° C.

Herein, a tensile adhesion strength when an dental adhesive resin cement was prepared by blending and mixing at a weight ratio shown in Tables 15, and this was brought into the sealed state, and was used under storage environment at 23° C. within 24 hours was adopted as an "initial" tensile adhesion strength. In addition, a tensile adhesion strength when an dental adhesive resin cement was prepared by blending and mixing at a weight ratio shown in Tables 15, and this was brought into the sealed state, and was used after storage for 2 months under storage environment at 50° C. was adopted as tensile strength "after 50° C. 2 months storage".

[Components and Abbreviations]

The abbreviations of the components used in the Examples are as follows.
3-MPTES: 3-Methacryloxypropyltriethoxysilane
6-MHPA: 6-Methacryloxyhexyl-phosphonoacetate
Bis-GMA: Bisphenol A diglycidyl methacrylate
3G: Triethylene glycol dimethacrylate
CQ: Camphor quinone
DMBE: ethyl p-dimethylaminobenzoate
Aluminum silicate glass: average particle size 5 μm, silane treated product R-972: Fine particle silicic acid [manufactured by Japan Aerosil Co., Ltd.]
FAM-401 (manufactured by FUJIFILM Corporation)
FAM-201 (manufactured by FUJIFILM Corporation)

(Materials and Apparatuses Used in Experiments)
Aluminum oxide plate: about 15×15×2 mm [manufactured by Japan Fine Ceramics Co., Ltd.]
Zirconium oxide plate: about 15×15×2 mm [manufactured by Japan Fine Ceramics Co., Ltd.]
Porcelain disk-like plate: diameter 15.0×5.0 mm [dental metal baking porcelain [trade name "Vintage Hello" (manufactured by SHOFU INC.)]]
Gold alloy flat plate: approximately 15×15×2 mm [trade name "SUPER GOLD Type 4" (manufactured by SHOFU INC.)]
Thermal cycle tester: [manufactured by Tokyo Giken Inc.]
Instron universal tester [manufactured by Instron]

composite resin. Subsequently, the dental composite resin was cured by subjecting the resin to 30 second light irradiation through the release film using a photo polymerization irradiator (Grip Light II manufactured by SHOFU INC.) to prepare an adhesion test specimen.

The adhesion test specimen was allowed to stand at room temperature for 30 minutes, after which the sample was immersed in distilled water. A total of 5 adhesion test specimens were prepared these samples were allowed to stand for 24 hours in a thermostat set at 37° C.

The tensile bond strength of the above adhesion test specimens was measured using a universal testing machine (manufactured by Shimadzu Corporation) with a crosshead

TABLE 15

| Component | | Example 8-1 | Example 8-2 | Example 8-3 | Example 8-4 | Example 8-5 | Comparative Example 8-1 | Comparative Example 8-2 | Comparative Example 8-3 |
|---|---|---|---|---|---|---|---|---|---|
| 3MPTES | | 7 | 7 | 7 | 7 | 7 | 7 | 7 | 7 |
| 6-MHPA | | 2 | 2 | 2 | 2 | 2 | 2 | 2 | 2 |
| 10-MDDT | | 1 | 1 | 1 | 1 | 1 | 1 | 1 | 1 |
| Bis-GMA | | 40 | 50 | 37.5 | 50 | 32.5 | 52.5 | 27.5 | 42.5 |
| 3G | | 32.5 | 30 | 30 | 31.5 | 30 | 30 | 30 | 30 |
| CQ | | 0.25 | 0.25 | 0.25 | 0.25 | 0.25 | 0.25 | 0.25 | 0.25 |
| DMBE | | 0.25 | 0.75 | 0.25 | 0.25 | 0.25 | 0.25 | 0.25 | 0.25 |
| R-972 | | 7 | 7 | 7 | 7 | 7 | 7 | 7 | 7 |
| FAM-401 | | 10 | 2 | 15 | 1 | 20 | 0 | 25 | 0 |
| FAM-201 | | 0 | 0 | 0 | 0 | 0 | 0 | 0 | 10 |
| Total component amount | | 100 | 100 | 100 | 100 | 100 | 100 | 100 | 100 |
| Porcelain | initial | 25.9 | 28.2 | 20.2 | 17.9 | 16.5 | 4.8 | 9.3 | 6.2 |
| | after 50° C. 2 months storage | 24.1 | 23.1 | 18.7 | 16.1 | 17.8 | 5.8 | 8.6 | 6.6 |
| Aluminum oxide | initial | 12.8 | 11.7 | 12.8 | 15.8 | 14.5 | 7.5 | 9.9 | 7.2 |
| | after 50° C. 2 months storage | 12.2 | 14.8 | 12.3 | 17.8 | 13.8 | 6.5 | 9.3 | 8.5 |
| Zirconium oxide | initial | 11.8 | 14.8 | 11.5 | 15.5 | 14.2 | 7.2 | 6.4 | 7.4 |
| | after 50° C. 2 months storage | 11.5 | 11.5 | 11.5 | 16.5 | 15.6 | 5.5 | 6.6 | 6.1 |
| Gold alloy | initial | 26.4 | 26.5 | 19.9 | 18.5 | 16.3 | 9.7 | 10.1 | 11.5 |
| | after 50° C. 2 months storage | 26.7 | 27.6 | 20.1 | 18.3 | 16.6 | 10.5 | 11 | 10.5 |

[9. Self-Adhesive Dental Composite Resin]

A characteristic confirmation test method in case that the dental composition is the self-adhesive dental composite resin is described below.

(9-1) Tooth Substance Adhesive Property Test
[Evaluation Purpose]
Evaluation of tooth substance adhesive property in the composition.
[Evaluation Method]
(Tooth Substance Adhesive Property Test 1)

The labial surfaces of bovine mandibular incisors were each polished with #80 silicon carbide paper (manufactured by Nihon Kenshi Co., Ltd.) under running water to obtain samples with an exposed flat dentin surface. Each of the obtained samples was further polished with #1000 silicon carbide paper (manufactured by Nihon Kenshi Co., Ltd.) under running water. After the completion of polishing, each sample was washed with water and an adhesive tape having a thickness of about 150 μm having a round hole with a diameter of 3 mm was attached to the smooth surface to define the adhesion area.

The dental composite resins prepared in Examples and Comparative Examples were filled within the round hole and the resin was covered with a release film (made of polyester). Next, a glass slide was placed on and pressed against the release film to flatten the surface of the applied dental speed set at 2 mm/min. The average of the measured values of these specimens was used as the value of tensile bond strength.

(Tooth Substance Adhesive Property Test 2)

The labial surfaces of bovine mandibular incisors were each polished with #80 silicon carbide paper (manufactured by Nihon Kenshi Co., Ltd.) under running water to obtain samples with an exposed flat dentin surface. Each of the obtained samples was further polished with #1000 silicon carbide paper (manufactured by Nihon Kenshi Co., Ltd.) under running water. After the completion of polishing, a commercially available dental etching material (manufactured by Kuraray Noritake Dental Inc. under the trade name K-Etchant Syringe) was applied to dentin. The sample was then allowed to stand for 10 seconds, and washed with water. After washing with water, an adhesive tape having a thickness of about 150 μm having a round hole with a diameter of 3 mm was attached to the smooth surface to define the adhesion area. Then, in the same manner as the tooth substance adhesive property test 1, the tensile adhesive strength to the dentin treated by the phosphoric acid etching treatment was measured.

[Components and Abbreviations]

The abbreviations of the materials used to prepare each composition are as follows.
FAM-401: Tetrafunctional (meth)acrylamide monomer (manufactured by FUJIFILM Corporation)
FAM-201: Bifunctional acrylamide monomer (manufactured by FUJIFILM Corporation)
MAEA: N-Methacryloyloxyethylacrylamide
MDP: 10-Methacryloyloxydecyl dihydrogen phosphate
Bis-GMA: 2,2-Bis[4-(3-methacryloyloxy-2-hydroxypropoxy)phenyl]propane
TEGDMA: Triethylene glycol dimethacrylate
HEMA: 2-Hydroxyethylmethacrylate
CQ: Camphor quinone
DABE: 4-(N,N-dimethylamino)ethyl benzoate
Inorganic filler: Silane treated filler
BHT: 2,6-Di-t-butyl-4-methylphenol (stabilizer (polymerization inhibitor))

Examples 9-1 to 9-6 and Comparative Examples 9-1 to 9-3

By using the above materials, self-adhesive dental composite resins of Examples 9-1 to 9-6 and dental composite resins of Comparative Examples 9-1 to 9-3 were prepared by mixing the components other than the filler among the components shown in Table 16 at room temperature to form a uniform liquid component, and then kneading the obtained liquid component and the filler (powder). Then, by using these dental composite resin, according to the above method, the tensile adhesive strength to dentin not subjected to phosphoric acid etching treatment, and the tensile adhesive strength to dentin subjected to phosphoric acid etching treatment was measured. Table 16 shows the compounding ratio (parts by weight) of these dental composite resins and the test results.

[Adhesion Test Method]
(Initial Adhesion Test)
Adhesion test specimen was immersed in 37° C. of water for 24 hours. Thereafter, adhesion test was performed.
(Durability Adhesion Test)
Adhesion test specimen was immersed in 37° C. of water for 24 hours. After immersion, 10000 times of thermal cycle (5° C.<-->50° C., immersion in each temperature for 1 minute) was applied. Thereafter, adhesion test was performed.
(Shelf Life Test)
After preparing the dental primer, 5 cc of the dental primer was collected into an airtight container. The airtight container was preserved for 1 year at a dark cold place of 23° C. and thereafter the Initial adhesion test and Durability adhesion test were performed.

Adhesion test was performed at 23° C. under the atmospheric pressure.
[Preparation of Sample]
Adhesive materials: 10-B1 to 10-B7 were prepared in accordance with an ordinary method by using following component at the formulation ratio shown in Table 17.
(Adhesive Materials: 10-B1 to 10-B7)
<Silane Coupling Agent>
Methyltrichlorosilane
γ-methacryloyloxypropyltrimethoxysilane
<Acid Anhydride and/or Weakly Acidic Compound>
Citric anhydride
Maleic anhydride
Pyrophosphoric acid
<Monomer Containing (Meth)Acrylamide Group>
FAM-401 (manufactured by FUJIFILM Corporation)
FAM-201 (manufactured by FUJIFILM Corporation)

TABLE 16

| Name/Abbreviation | Comparative Example 9-1 | Comparative Example 9-2 | Comparative Example 9-3 | Example 9-1 | Example 9-2 | Example 9-3 | Example 9-4 | Example 9-5 | Example 9-6 |
| --- | --- | --- | --- | --- | --- | --- | --- | --- | --- |
| FAM-401 | 0 | 0 | 0 | 10 | 2.5 | 1.2 | 15 | 0.2 | 20 |
| FAM-201 | 1.5 | 0.9 | 8.08 | 0 | 0 | 0 | 0 | 0 | 2.88 |
| MAEA | 2.99 | 8.08 | 0.9 | 0 | 0 | 0 | 0 | 0 | 0 |
| MDP | 2.99 | 2.99 | 2.99 | 2 | 3.1 | 3.28 | 3.12 | 2.97 | 2.88 |
| Bis-GMA | 8.97 | 8.97 | 8.97 | 7.7 | 9.05 | 8.8 | 9.37 | 8.91 | 5 |
| TEGDMA | 8.97 | 5.98 | 5.98 | 7.7 | 9.05 | 6.56 | 6.24 | 7.56 | 5 |
| HEMA | 4.49 | 2.99 | 2.99 | 5.21 | 4.65 | 3.28 | 3.12 | 10 | 2.88 |
| CQ | 0.12 | 0.12 | 0.12 | 0.12 | 0.12 | 0.13 | 0.12 | 0.12 | 0.12 |
| DABE | 0.24 | 0.24 | 0.24 | 0.24 | 0.25 | 0.26 | 0.25 | 0.24 | 0.23 |
| Silane treated filler | 69.7 | 69.7 | 69.7 | 67 | 71.25 | 76.46 | 62.75 | 69.97 | 60.98 |
| BHT | 0.03 | 0.03 | 0.03 | 0.03 | 0.03 | 0.03 | 0.03 | 0.03 | 0.03 |
| Tensile adhesive strength without phosphoric acid etchine (Mpa) | 3.5 | 3.1 | 3.0 | 13.2 | 13.5 | 13.8 | 13.5 | 10.8 | 11.0 |
| Tensile adhesive strength with phosphoric acid etching (Mpa) | 3.3 | 3.0 | 3.2 | 13.1 | 13.8 | 13.3 | 13.0 | 10.5 | 10.7 |

As shown in Table 16, in Examples 9-1 to 9-6, it was confirmed that excellent self-adhesiveness was obtained in both cases with and without phosphoric acid etching without excessive drying. On the other hand, in Comparative Examples 9-1 to 9-3, clinically necessary self-adhesiveness was not obtained and practicality was not recognized in both cases with and without phosphoric acid etching.

[10. Adhesive Composition]

A characteristic confirmation test method in case that the dental composition is the adhesive composition is described below.

<Polymerizable Monomer>

2-hydroxyethyl (meth)acrylate (2HEMA)

2,2-bis(4-(3-methacryloyloxy-2-hydroxypropoxy)phenyl) propane (Bis-GMA)

Di(methacryloyloxy)-2,2,4-trimethylhexamethylene diurethane (UDMA)

Triethylene glycol dimethacrylate (TEGDMA)

<Polymerization Catalyst (Photo Polymerization Initiator)>

Camphor quinone

Ethyl p-N,N-dimethylaminobenzoate

[Lithium Disilicate Glass Ceramics]
(Preparation of Adherend and Adhesive Body)

Lithium disilicate glass ceramics adherend and Lithium disilicate glass ceramics adhesive body were prepared by molding lithium disilicate glass ceramics (manufactured by SHOFU INC.) using CAD/CAM system or press system, then sintering in accordance with the instruction, washing and storing in water for 1 week. The Lithium disilicate glass ceramics adherend (Large) was in a columnar shape formed to have a dimension of 2 cm (diameter) by 1 cm (thickness). The Lithium disilicate glass ceramics adherend (Small) was in a columnar shape formed to have a dimension of 0.5 cm (diameter) by 1 cm (thickness).

(Preparation of Adhesive Test Specimen)

The Lithium disilicate glass ceramics adherend (Large) and the Lithium disilicate glass ceramics adherend (Small) were sandblasted with alumina having an average particle size of about 50 μm (with 0.2 MPa, for 1 second), and the Lithium disilicate glass ceramics adherend (Small) was applied with one of the Adhesive material: 10-B1 to 10-B7. Thereafter, Zirconia adherend (Small) were pressure contacted to the Lithium disilicate glass ceramics adherend (Large). The excess Adhesive material was removed. Subsequently, the pressure contacted Lithium disilicate glass ceramics (Large) and the Lithium disilicate glass ceramics (Small) were left for 15 minutes for curing to prepare adhesion test specimen (the number of test specimen N=5).

[Porcelain]
(Preparation of Adherend and Adhesive Body)

Porcelain adherend and Porcelain adhesive body were prepared by building-up and firing "VINTAGE LD" (manufactured by SHOFU INC.) in accordance with the instruction, and washing and storing in water for 1 week. The Porcelain adherend (Large) was in a columnar shape formed to have a dimension of 2 cm (diameter) by 1 cm (thickness). The Porcelain adherend (Small) was in a columnar shape formed to have a dimension of 0.5 cm (diameter) by 1 cm (thickness).

(Preparation of Adhesion Test Specimen)

The Porcelain adherend (Large) and the Porcelain adherend (Small) were sandblasted with alumina having an average particle size of about 50 μm (with 0.2 MPa, for 1 second), then the Porcelain adherend (Small) was applied with one of the Adhesive material: 10-B1 to 10-B7. Thereafter, Porcelain adherend (Small) were pressure contacted to the Porcelain adherend (Large). The excess Adhesive material was removed. Subsequently, the pressure contacted Porcelain adherend (Large) and the Porcelain adherend (Small) were left for 15 minutes for curing to prepare adhesion test specimen (the number of test specimen N=5).

[Composite]
(Preparation of Adherend)

Composite resin adherend was prepared by cutting and machining the resin disk material "SHOFU DISK HC" (manufactured by SHOFU INC.) using CAD/CAM system, and washing and storing in water for 1 week. The Composite resin adherend was in a columnar shape formed to have a dimension of 2 cm (diameter) by 1 cm (thickness).

(Preparation of Adhesion Test Specimen)

The Composite resin adherend was applied with one of the Adhesive material: 10-B1 to 10-B7. Thereafter, light irradiation was performed for 30 seconds by Griplight 2 (manufactured by SHOFU INC.). The adhesion surface was defined by using jig having a diameter of 0.5 mm, then was filled with composite resin (LITE FIL 2: manufactured by SHOFU INC.). The composite resin was cured by irradiating light for 30 seconds by Griplight 2 (manufactured by SHOFU INC.) to prepare adhesion test specimen (the number of test specimen N=5).

TABLE 17

| Adhesive material: B (g %) | | B10-1 | B10-2 | B10-3 | B10-4 | B10-5 | B10-6 | B10-7 |
|---|---|---|---|---|---|---|---|---|
| Hydrophobic monomer | Bis-GMA | | | 23.0 | 50.0 | | 50.0 | 66.2 |
| | UDMA | 43.4 | 45.6 | | | 42.6 | | |
| | TEGDMA | 14.6 | 13.1 | 35.4 | 7.0 | 16.6 | 7.0 | 9.6 |
| Hydrophilic monomer | HEMA | 30.7 | 34.0 | 25.3 | 21.7 | 34.4 | 21.7 | 15.9 |
| Photo polymerization initiator | Camphor quinone | 0.3 | 0.3 | 0.3 | 0.3 | 0.3 | 0.3 | 0.3 |
| | Ethyl p-N,N-dimethylaminobenzoate | 1 | 1 | 1 | 1 | 1 | 1 | 1 |
| Silane coupling agent | Methyltrichlorosilane | | 4.0 | | | | | |
| | γ-methacryloyloxypropyl trimethoxysilane | 4.0 | | 4.0 | 4.0 | 4.0 | 4.0 | 4.0 |
| Acid anhydride and/or weakly acidic compound | Citric anhydride | 1.0 | | | | 1.0 | | |
| | Maleic anhydride | | 1.0 | 1.0 | 1.0 | | | 1.0 |
| | Pyrophosphoric acid | | | | | | 1.0 | |
| Monomer containing (meth)acrylamide group | FAM-401 | 5.0 | 1.0 | 10.0 | 15.0 | 0.1 | 15.0 | |
| | FAM-201 | | | | | | | 2.0 |
| Total | | 100.0 | 100.0 | 100.0 | 100.0 | 100.0 | 100.0 | 100.0 |

TABLE 18

| Sample preparation | | Example 10-1 | Example 10-2 | Example 10-3 | Example 10-4 | Example 10-5 | Example 10-6 | Comparative Example 10-1 |
|---|---|---|---|---|---|---|---|---|
| Adherend | Adhesive material: B | B10-1 | B10-2 | B10-3 | B10-4 | B10-5 | B10-6 | B10-7 |
| | Lithium disilicate glass ceramics adherend (Large) | ○ | ○ | ○ | ○ | ○ | ○ | ○ |
| | Composite resin adherend | | | | | | | |
| | Porcelain adherend (Large) | | | | | | | |
| Adhesive body | Lithium disilicate glass ceramics adherend (Small) | ○ | ○ | ○ | ○ | ○ | ○ | ○ |
| | Composite resin | | | | | | | |
| | Porcelain adherend (Small) | | | | | | | |

| Test result | | Example 10-1 | Example 10-2 | Example 10-3 | Example 10-4 | Example 10-5 | Example 10-6 | Comparative Example 10-1 |
|---|---|---|---|---|---|---|---|---|
| Without shelf life test | Initial adhesion (MP) | 13.3 | 13.1 | 12.6 | 11.3 | 12.7 | 11.0 | 7.2 |
| | Thermal (MP) | 13.1 | 13.3 | 12.4 | 10.2 | 12.4 | 10.5 | 7.9 |
| With shelf life test | Initial adhesion (MP) | 13.0 | 13.5 | 12.1 | 10.5 | 12.1 | 10.5 | Fallen off |
| | Thermal (MP) | 12.6 | 13.0 | 11.9 | 10.6 | 12.1 | 10.7 | — |

| Sample preparation | | Example 10-7 | Example 10-8 | Example 10-9 | Example 10-10 | Example 10-11 | Example 10-12 | Comparative Example 10-2 |
|---|---|---|---|---|---|---|---|---|
| Adherend | Adhesive material: B | B10-1 | B10-2 | B10-3 | B10-4 | B10-5 | B10-6 | B10-7 |
| | Lithium disilicate glass ceramics adherend (Large) | | | | | | | |
| | Composite resin adherend (Large) | ○ | ○ | ○ | ○ | ○ | ○ | ○ |
| | Porcelain adherend (Large) | | | | | | | |
| Adhesive body | Lithium disilicate glass ceramics adherend (Small) | | | | | | | |
| | Composite resin | ○ | ○ | ○ | ○ | ○ | ○ | ○ |
| | Porcelain adherend (Small) | | | | | | | |

| Test result | | Example 10-7 | Example 10-8 | Example 10-9 | Example 10-10 | Example 10-11 | Example 10-12 | Comparative Example 10-2 |
|---|---|---|---|---|---|---|---|---|
| Without shelf life test | Initial adhesion (MP) | 13.7 | 14.1 | 12.2 | 11.1 | 12.5 | 11.1 | 7.0 |
| | Thermal (MP) | 13.3 | 13.7 | 12.0 | 11.2 | 13.3 | 11.3 | 7.1 |
| With shelf life test | Initial adhesion (MP) | 14.1 | 13.5 | 12.7 | 10.6 | 13.5 | 11.0 | Fallen off |
| | Thermal (MP) | 13.8 | 13.3 | 12.5 | 10.5 | 13.3 | 10.8 | — |

| Sample preparation | | Example 10-13 | Example 10-14 | Example 10-15 | Example 10-16 | Example 10-17 | Example 10-18 | Comparative Example 10-3 |
|---|---|---|---|---|---|---|---|---|
| Adherend | Adhesive material: B | B10-1 | B10-2 | B10-3 | B10-4 | B10-5 | B10-6 | B10-7 |
| | Lithium disilicate glass ceramics adherend (Large) | | | | | | | |
| | Composite resin adherend | | | | | | | |
| | Porcelain adherend (Large) | ○ | ○ | ○ | ○ | ○ | ○ | ○ |
| Adhesive body | Lithium disilicate glass ceramics adherend (Small) | | | | | | | |
| | Composite resin | | | | | | | |
| | Porcelain adherend (Small) | ○ | ○ | ○ | ○ | ○ | ○ | ○ |

| Test result | | Example 10-13 | Example 10-14 | Example 10-15 | Example 10-16 | Example 10-17 | Example 10-18 | Comparative Example 10-3 |
|---|---|---|---|---|---|---|---|---|
| Without shelf life test | Initial adhesion (MP) | 12.7 | 12.7 | 11.6 | 10.2 | 11.3 | 10.5 | 6.5 |
| | Thermal (MP) | 12.5 | 12.1 | 12.2 | 10.0 | 11.0 | 10.1 | 6.3 |
| With shelf life test | Initial adhesion (MP) | 12.7 | 12.2 | 11.9 | 10.4 | 10.6 | 10.5 | Fallen off |
| | Thermal (MP) | 12.7 | 12.6 | 11.5 | 9.5 | 10.3 | 9.6 | — |

In examples 10-1 to 10-6 (adhesion between lithium disilicate glass ceramics and lithium disilicate glass ceramics), 10-7 to 10-12 (adhesion of composite resin to composite resin adherend) and examples 10-13 to 10-18 (adhesion between porcelain and porcelain), although the materials and method of adhesive are different in these examples, it was confirmed that adhesive strength was stable in both of Initial adhesion test and Durability adhesion test regardless of "Shelf life test".

On the other hand, in the Comparative Examples 10-1 to 10-3, although the materials and method of adhesive are different in these comparative examples, certain adhesive strength was confirmed in both of Initial adhesion test and Durability adhesion test of "Without shelf life test". However, in "With shelf life test", although it was possible to prepare the adhesion test specimen, it was confirmed that adhesive body had already fallen off at the stage of the Initial adhesion test.

With respect to the use of substantially any plural and/or singular terms herein, those having skill in the art can translate from the plural to the singular and/or from the singular to the plural as is appropriate to the context.

Although the description herein has been given with reference to the drawings and embodiments, it should be noted that those skilled in the art may make various changes and modifications on the basis of this disclosure without difficulty. Accordingly, any such changes and modifications are intended to be included in the scope of the embodiments.

What is claimed is:

1. A dental composition containing component (a): monomer containing (meth)acrylamide group represented by formula (1):

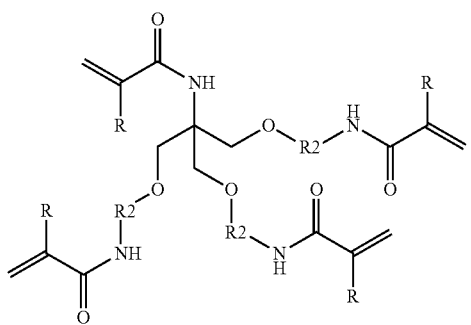

(1)

wherein R represents a hydrogen atom or a methyl group and Rs may be the same or different from each other, R2 is an alkyl group having 2 to 6 carbon atoms and R2s may be the same or different from each other, wherein the dental composition does not contain (i): acidic group-containing monomer.

2. The dental composition of claim 1, wherein the component (a): monomer containing (meth)acrylamide group represented by formula (1) is a monomer represented by formula (2):

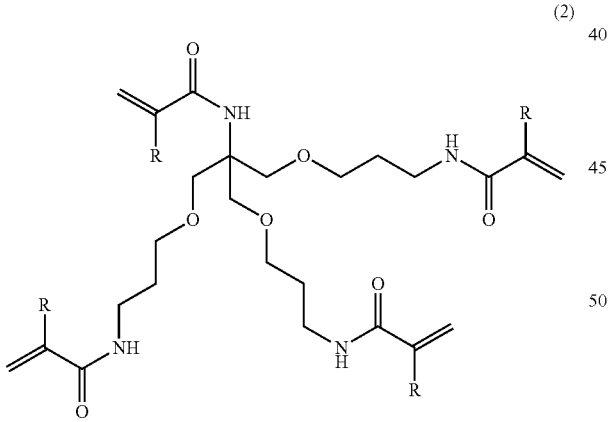

(2)

wherein R represents a hydrogen atom or a methyl group and Rs may be the same or different from each other.

3. The dental composition of claim 1, wherein all Rs in the formula (2) are hydrogen atom.

4. The dental composition of claim 2, wherein the component (a): monomer containing (meth)acrylamide group represented by formula (1) is the only monomer containing (meth)acrylamide in the dental composition.

5. A dental composite material containing component (a): monomer containing (meth)acrylamide group represented by formula (1):

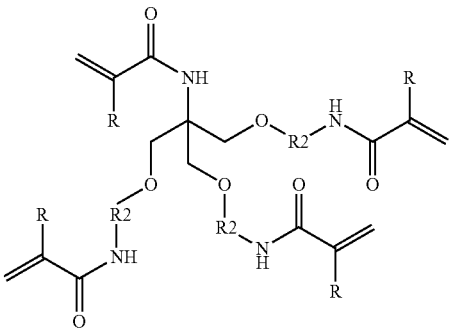

(1)

wherein R represents a hydrogen atom or a methyl group and Rs may be the same or different from each other, R2 is an alkyl group having 2 to 6 carbon atoms and R2s may be the same or different from each other, component (b): filler, component (c): monomer other than the component (a), and component (d): polymerization initiator, and wherein a ratio of the component (a) in the total amount of the component (a) and the component (c) is within a range of 0.1 to 20 wt. %, and wherein the dental composite material does not contain (i): acidic group-containing monomer.

6. A resin cement containing component (a): monomer containing (meth)acrylamide group represented by formula (1):

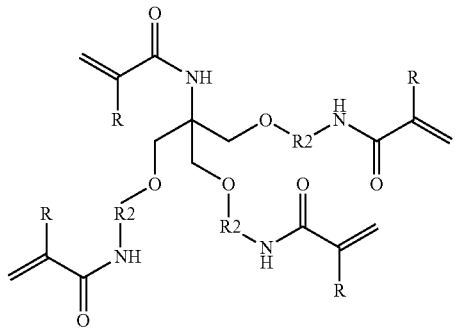

(1)

wherein R represents a hydrogen atom or a methyl group and Rs may be the same or different from each other, R2 is an alkyl group having 2 to 6 carbon atoms and R2s may be the same or different from each other, component (b): filler, component (f): polymerization catalyst, component (g): silane coupling agent, component (h): radical polymerizable monomer, and component (i): acidic group-containing monomer, and wherein 0.1 to 20 parts by weight of the component (a) is contained with respect to 100 parts by weight of the component (h).

7. A denture restorative material containing
component (a): monomer containing (meth)acrylamide group represented by formula (1):

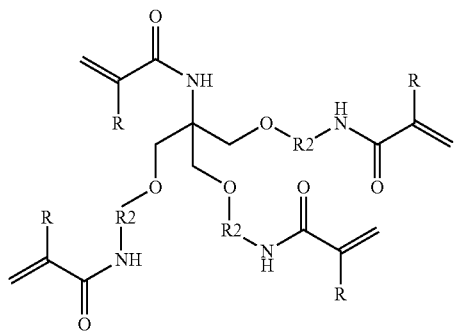

(1)

wherein R represents a hydrogen atom or a methyl group and Rs may be the same or different from each other, R2 is an alkyl group having 2 to 6 carbon atoms and R2s may be the same or different from each other,
  component (c): monomer other than the component (a),
  component (j): (meth) acrylic acid (co) polymer, and
  component (f): polymerization catalyst, and
  wherein a ratio of the component (a) in the total amount of the component (a) and the component (c) is within a range of 0.1 to 20 wt. %, and
  wherein the component (f) contains at least one of a combination of a barbituric acid derivative and a halogen ion-forming compound or a combination of an organic peroxide and an amine compound.

8. A tooth substance adhesive primer containing
component (a): monomer containing (meth)acrylamide group represented by formula (1):

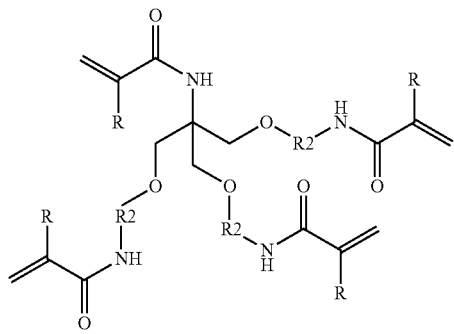

(1)

wherein R represents a hydrogen atom or a methyl group and Rs may be the same or different from each other, R2 is an alkyl group having 2 to 6 carbon atoms and R2s may be the same or different from each other,
  component (k): acid group-containing monomer,
  component (l): water,
  component (m): water-soluble organic solvent, and
  component (f): polymerization catalyst, and
  wherein 0.1 to 20 parts by weight of the component (a) is contained with respect to 100 parts by weight of the total of the components of the tooth substance adhesive primer other than the component (a) and the component (f).

9. A dental primer for modifying a surface of a tooth restoration containing
component (a): monomer containing (meth)acrylamide group represented by formula (1):

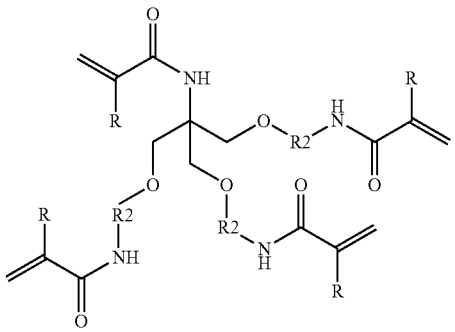

(1)

wherein R represents a hydrogen atom or a methyl group and Rs may be the same or different from each other, R2 is an alkyl group having 2 to 6 carbon atoms and R2s may be the same or different from each other,
  component (p): organic solvent,
  component (g): silane coupling agent, and
  component (q): acid anhydride and/or weakly acidic compound, and
  wherein the component (g) is contained within a range of 0.1 to 15 wt. %.

10. A dental adhesive composition containing
component (a): monomer containing (meth)acrylamide group represented by formula (1):

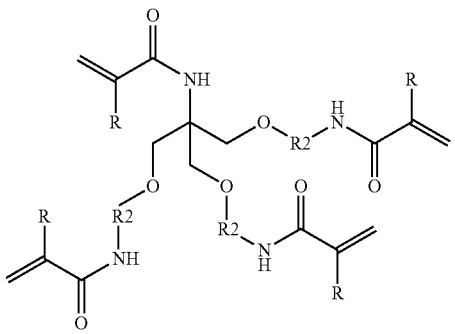

(1)

wherein R represents a hydrogen atom or a methyl group and Rs may be the same or different from each other, R2 is an alkyl group having 2 to 6 carbon atoms and R2s may be the same or different from each other,
  component (c): monomer other than the component (a), and
  component (f): polymerization catalyst, and
  wherein the component (a) is contained within a range of 0.1 to 20 wt. %, and
  wherein the dental adhesive composition does not contain (i): acidic group-containing monomer.

11. A tooth substance adhesive composition containing
component (a): monomer containing (meth)acrylamide group represented by formula (1):

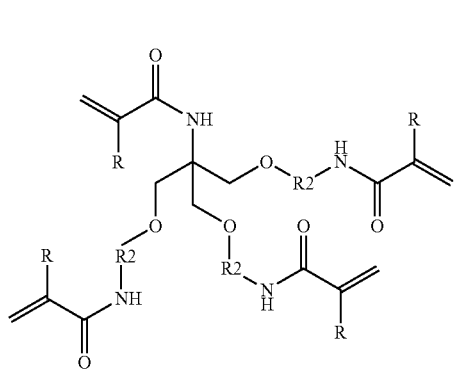

(1)

wherein R represents a hydrogen atom or a methyl group and Rs may be the same or different from each other, R2 is an alkyl group having 2 to 6 carbon atoms and R2s may be the same or different from each other,
component (i): acidic group-containing monomer,
component (t): monomer other than the component (a) and the component (i),
component (l): water and/or component (p): organic solvent,
component (f): polymerization catalyst, and
component (u): sulfur atom-containing monomer, and
wherein the component (a) is contained within a range of 0.1 to 20 wt. %.

12. A dental adhesive resin cement containing
component (a): monomer containing (meth)acrylamide group represented by formula (1):

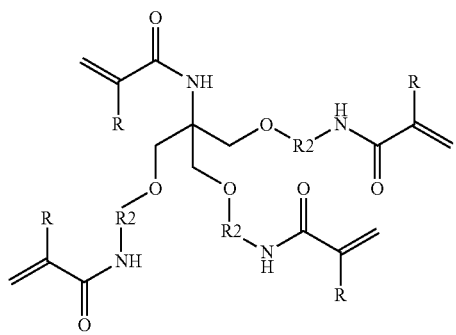

(1)

wherein R represents a hydrogen atom or a methyl group and Rs may be the same or different from each other, R2 is an alkyl group having 2 to 6 carbon atoms and R2s may be the same or different from each other,
component (b): filler,
component (i): acidic group-containing monomer,
component (u): sulfur atom-containing monomer,
component (g): silane coupling agent,
component (d): polymerization initiator, and
component (v): monomer other than the component (a), the component (i) and the component (u), and
wherein the component (a) is contained within a range of 0.1 to 20 wt. %.

13. A self-adhesive dental composite resin containing
component (a): monomer containing (meth)acrylamide group represented by formula (1):

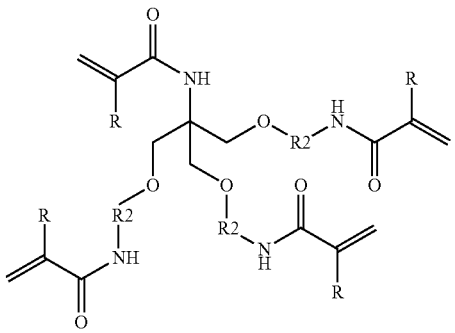

(1)

wherein R represents a hydrogen atom or a methyl group and Rs may be the same or different from each other, R2 is an alkyl group having 2 to 6 carbon atoms and R2s may be the same or different from each other,
component (i): acidic group-containing monomer,
component (w): photopolymerization catalyst,
component (b): filler, and
component (u): sulfur atom-containing monomer, and
wherein the component (a) is contained within a range of 0.1 to 20 wt. %.

14. An adhesive composition containing
component (a): monomer containing (meth)acrylamide group represented by formula (1):

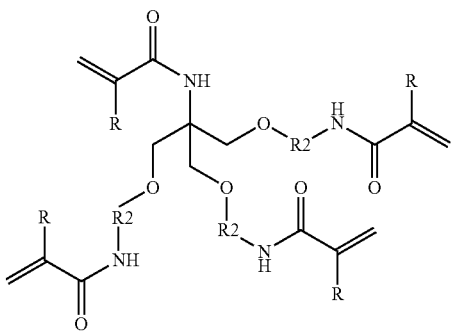

(1)

wherein R represents a hydrogen atom or a methyl group and Rs may be the same or different from each other, R2 is an alkyl group having 2 to 6 carbon atoms and R2s may be the same or different from each other,
component (r): hydrophilic monomer,
component (s): hydrophobic monomer,
component (f): polymerization catalyst,
component (q): acid anhydride and/or weakly acidic compound, and
component (g): silane coupling agent, and
wherein the component (a) is contained within a range of 0.1 to 20 wt. %; and
the adhesive composition does not contain (i): acidic group-containing monomer.

* * * * *